(12) United States Patent
Gatter et al.

(10) Patent No.: US 10,640,796 B2
(45) Date of Patent: *May 5, 2020

(54) YEAST STRAINS WITH REDUCED FATTY ALCOHOL OXIDASE ACTIVITY AND METHOD FOR THE PRODUCTION OF OMEGA-HYDROXY FATTY ACIDS AND DICARBOXYLIC ACIDS

(71) Applicant: Provivi, Inc., Santa Monica, CA (US)

(72) Inventors: Michael Gatter, Dresden (DE); Falk Matthaus, Dresden (DE); Gerold Barth, Dresden (DE)

(73) Assignee: Provivi, Inc., Santa Monica, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/102,213

(22) Filed: Aug. 13, 2018

(65) Prior Publication Data

US 2018/0371510 A1 Dec. 27, 2018

Related U.S. Application Data

(63) Continuation of application No. 15/103,191, filed as application No. PCT/EP2014/077237 on Dec. 10, 2014, now Pat. No. 10,093,950.

(30) Foreign Application Priority Data

Dec. 12, 2013 (DE) .......... 10 2013 022 175

(51) Int. Cl.

| | | |
|---|---|---|
| C12P 7/64 | (2006.01) | |
| C12N 9/04 | (2006.01) | |
| C12P 7/44 | (2006.01) | |
| C12N 9/90 | (2006.01) | |
| C12N 9/02 | (2006.01) | |

(52) U.S. Cl.
CPC .......... *C12P 7/6409* (2013.01); *C12N 9/001* (2013.01); *C12N 9/0006* (2013.01); *C12N 9/90* (2013.01); *C12P 7/44* (2013.01); *C12P 7/6427* (2013.01); *C12Y 101/0302* (2013.01); *C12Y 103/03006* (2013.01); *C12Y 502/01008* (2013.01)

(58) Field of Classification Search
None
See application file for complete search history.

(56) References Cited

U.S. PATENT DOCUMENTS

| | | | |
|---|---|---|---|
| 4,339,536 A | 7/1982 | Kato et al. | |
| 7,238,482 B2 | 7/2007 | Picataggio et al. | |
| 9,157,103 B2 | 10/2015 | Hattendorf et al. | |
| 10,093,950 B2 * | 10/2018 | Gatter | C12N 9/0006 |
| 10,308,962 B1 * | 6/2019 | Leonard | A01N 31/02 |
| 2010/0041115 A1 * | 2/2010 | Nicaud | C12N 9/0042 |
| | | | 435/145 |
| 2014/0275595 A1 | 9/2014 | Wampler et al. | |
| 2015/0275188 A1 | 10/2015 | Hu et al. | |
| 2015/0275245 A1 | 10/2015 | Hans et al. | |
| 2016/0039737 A1 | 2/2016 | Champagne et al. | |
| 2016/0222419 A1 | 8/2016 | Stuart | |
| 2016/0304913 A1 | 10/2016 | Gatter et al. | |
| 2017/0037069 A1 | 2/2017 | Toth et al. | |
| 2017/0066993 A1 | 3/2017 | Wampler et al. | |
| 2017/0145433 A1 | 5/2017 | Merlo et al. | |

FOREIGN PATENT DOCUMENTS

| | | |
|---|---|---|
| EP | 0296506 A2 | 12/1988 |
| WO | WO 2000/017380 A1 | 3/2000 |
| WO | WO 2006/064131 A | 6/2006 |
| WO | WO 2011/008232 A2 | 1/2011 |
| WO | WO 2013/006730 A2 | 1/2013 |
| WO | WO 2013/006733 A2 | 1/2013 |
| WO | WO 2013/092426 A1 | 6/2013 |
| WO | WO 2013/151393 A1 | 10/2013 |
| WO | WO 2015/086684 A1 | 6/2015 |
| WO | WO 2015/155593 A1 | 10/2015 |
| WO | WO 2016/159869 A1 | 10/2016 |

OTHER PUBLICATIONS

Morin et al. PLoS One. 2011;6(11):e27966. Epub Nov. 22, 2011. (Year: 2011).*
Matatiele. Fatty Alcohol and Fatty Aldehyde Dehydrogenases of Yarrowia lipolytica. May 2005. (Year: 2005).*
Xue et al. Nat Biotechnol. Aug. 2013;31(8):734-40. Epub Jul. 21, 2013 (Year: 2013).*
Accession Q6CEP8. Aug. 16, 2004.
Accession Q6C297. Aug. 16, 2004.
Accession Q6C7TO. Aug. 16, 2004.
Accession F2Z678. May 31, 2011.
Accession Q6CGT5. Aug. 16, 2004.
Accession Q6C5R5. Aug. 16, 2004.
Accession Q6CAJ7. Aug. 16, 2004.
Accession Q6CGX5. Aug. 16, 2004.
Accession Q6C6PO. Aug. 16, 2004.
Accession F2Z6C9. May 31, 2011.
Accession Q6C7L9. Aug. 16, 2004.
Accession Q6CD17. Aug. 16, 2004.
Athenstaedt, K. "YALI0E32769g (DGA1) and YALI0E16797g (LRO1) encode major triacylglycerol synthases of the oleaginous yeast *Yarrowia lipolytica*." Biochimica et Biophysica Acta (BBA)—Molecular and Cell Biology of Lipids (2011); 1811.10: 587-596.
Barth, et al. "Physiology and genetics of the dimorphic fungus *Yarrowia lipolytica*." FEMS Microbiology Reviews (1997); 19.4: 219-237.
Boeke, et al. "A positive selection for mutants lacking orotidine-5'-phosphate decarboxylase activity in yeast: 5-fluoro-orotic acid resistance." Molecular and General Genetics MGG (1984); 197.2: 345-346.

(Continued)

*Primary Examiner* — Christian L Fronda
(74) *Attorney, Agent, or Firm* — Cooley LLP

(57) ABSTRACT

The invention relates to various new yeast strains of the type *Yarrowia lipolytica* as well as relevant methods for the biocatalytic preparation of ω-hydroxy fatty acids or dicarboxylic acids with the aid of these strains, whereby the formation of ω-hydroxy fatty acids or dicarboxylic acids is advantageously increased.

21 Claims, 7 Drawing Sheets

Specification includes a Sequence Listing.

(56) References Cited

OTHER PUBLICATIONS

Dujon, et al., "Genome evolution in yeasts." Nature (2004); 430: 35-44.
Fickers, et al. "Hydrophobic substrate utilisation by the yeast *Yarrowia lipolytica*, and its potential applications." FEMS Yeast Research (2005); 5.6-7: 527-543.
Fickers, et al. "New disruption cassettes for rapid gene disruption and marker rescue in the yeast *Yarrowia lipolytica*." Journal of Microbiological Methods (2003); 55.3: 727-737.
Gatter, Michael, et al. "A newly identified fatty alcohol oxidase gene is mainly responsible for the oxidation of long-chain ω-hydroxy fatty acids in Yarrowia lipolytica." FEMS Yeast Research (2014); 14.6: 858-872.
Haddouche et al. "Roles of multiple acyl-CoA oxidases in the routing of carbon flow towards β-oxidation and polyhydroxyalkanoate biosynthesis in Yarrowia lipolytica." FEMS Yeast Research (2010); 10(7): 917-927.
Kemp, Glenwyn D., et al. "Light sensitivity of then-alkane-induced fatty alcohol oxidase from Candida tropicalis and Yarrowia lipolytica." Applied Microbiology and Biotechnology (1990); 32.4: 461-464.
Lu, et al. "Biosynthesis of Monomers for Plastics from Renewable Oils." Journal of the American Chemical Society (2010); 132.43: 15451-15455.
Matatiele, Puleng Rose. "Fatty alchohol and fatty aldehyde dehydrogenases of Yarrowia lipolytica." Diss. University of the Free State (2005); 201 pages.
Mauersberger, et al. "Insertional Mutagenesis in the n-Alkane-Assimilating Yeast *Yarrowia lipolytica*: Generation of Tagged Mutations in Genes Involved in Hydrophobic Substrate Utilization." Journal of Bacteriology (2001); 183.17: 5102-5109.
Nicaud. "Yarrowia lipolytica." Yeast (2012); 29(10): 409-418.
PCT/EP2014/077237, International Preliminary Report on Patentability dated Jun. 14, 2016, 8 pages.
PCT/EP2014/077237, International Search Report and Written Opinion dated Apr. 7, 2015, 12 pages.
Picataggio, et al. "Metabolic Engineering of Candida Tropicalis for the Production of Long-Chain Dicarboxylic Acids." Nature Biotechnology (1992); 10.8: 894-898.
Smit, et al. "αω-Dicarboxylic acid accumulation by acyl-CoA oxidase deficient mutants of Yarrowia lipolytica." Biotechnology Letters (2005); 27.12: 859-864.
Takai et al. "Construction and characterization of a Yarrowia lipolytica mutant lacking genes encoding cytochromes P450 subfamily 52." Fungal Genetics and Biology Biol. (2012); 49(1): 58-64.

* cited by examiner

SEQUENCE LISTING

<160> NUMBER OF SEQ ID NOS: 101

<210> SEQ ID NO 1
<211> LENGTH: 2974
<212> TYPE: DNA
<213> ORGANISM: Artificial Sequence
<220> FEATURE:
<223> OTHER INFORMATION: pJET1.2/blunt (blunt end cloning verctor)

<400> SEQUENCE: 1

```
atcttgctga aaaactcgag ccatccggaa gatctggcgg ccgctctccc tatagtgagt      60
cgtattacgc cggatggata tggtgttcag gcacaagtgt taaagcagtt gattttattc     120
actatgatga aaaaacaat gaatggaacc tgctccaagt taaaaataga gataataccg     180
aaaactcatc gagtagtaag attagagata atacaacaat aaaaaaatgg tttagaactt     240
actcacagcg tgatgctact aattgggaca attttccaga tgaagtatca tctaagaatt     300
taaatgaaga agacttcaga gcttttgtta aaaattattt ggcaaaaata atataattcg     360
gctgcagggg cggcctcgtg atacgcctat ttttataggt taatgtcatg ataataatgg     420
tttcttagac gtcaggtggc acttttcggg gaaatgtgcg cggaacccct atttgtttat     480
ttttctaaat acattcaaat atgtatccgc tcatgagaca ataaccctga taaatgcttc     540
aataatattg aaaaggaag agtatgagta ttcaacattt ccgtgtcgcc cttattccct     600
ttttgcggc attttgcctt cctgtttttg ctcacccaga aacgctggtg aaagtaaaag     660
atgctgaaga tcagttgggt gcacgagtgg gttacatcga actggatctc aacagcggta     720
agatccttga gagttttcgc cccgaagaac gttttccaat gatgagcact tttaaagttc     780
tgctatgtgg cgcggtatta tcccgtattg acgccgggca agagcaactc ggtcgccgca     840
tacactattc tcagaatgac ttggttgagt actcaccagt cacagaaaag catcttacgg     900
atggcatgac agtaagagaa ttatgcagtg ctgccataac catgagtgat aacactgcgg     960
ccaacttact tctgacaacg atcggaggac cgaaggagct aaccgctttt ttgcacaaca    1020
tgggggatca tgtaactcgc cttgatcgtt gggaaccgga gctgaatgaa gccataccaa    1080
acgacgagcg tgacaccacg atgcctgtag caatggcaac aacgttgcgc aaactattaa    1140
ctggcgaact acttactcta gcttcccggc aacaattaat agactggatg gaggcggata    1200
aagttgcagg accacttctg cgctcggccc ttccggctgg ctggtttatt gctgataaat    1260
ctggagccgg tgagcgtggg tctcgcggta tcattgcagc actggggcca gatggtaagc    1320
cctcccgtat cgtagttatc tacacgacgg ggagtcaggc aactatggat gaacgaaata    1380
gacagatcgc tgagataggt gcctcactga ttaagcattg gtaactgtca gaccaagttt    1440
actcatatat actttagatt gatttaaaac ttcattttta atttaaaagg atctaggtga    1500
agatcctttt tgataatctc atgaccaaaa tcccttaacg tgagttttcg ttccactgag    1560
cgtcagaccc cgtagaaaag atcaaaggat cttcttgaga tcctttttt ctgcgcgtaa    1620
tctgctgctt gcaaacaaaa aaaccaccgc taccagcggt ggtttgtttg ccggatcaag    1680
agctaccaac tcttttccg aaggtaactg gcttcagcag agcgcagata ccaaatactg    1740
tccttctagt gtagccgtag ttaggccacc acttcaagaa ctctgtagca ccgcctacat    1800
acctcgctct gctaatcctg ttaccagtgg ctgctgccag tggcgataag tcgtgtctta    1860
ccgggttgga ctcaagacga tagttaccgg ataaggcgca gcggtcgggc tgaacggggg    1920
gttcgtgcac acagcccagc ttggagcgaa cgacctacac cgaactgaga tacctacagc    1980
gtgagctatg agaaagcgcc acgcttcccg aagggagaaa ggcggacagg tatccggtaa    2040
```

```
gcggcagggt cggaacagga gagcgcacga gggagcttcc aggggggaaac gcctggtatc    2100 tttatagtcc tgtcgggttt cgccacctct gacttgagcg tcgatttttg tgatgctcgt    2160
caggggggcg gagcctatgg aaaaacgcca gcaacgcggc cttttttacgg ttcctggcct    2220 tttgctggcc ttttgctcac atgttctttc ctgcgttatc ccctgattct gtggataacc    2280
gtattaccgc ctttgagtga gctgataccg ctcgccgcag ccgaacgacc gagcgcagcg    2340
agtcagtgag cgaggaagcg gaagagcgcc caatacgcaa accgcctctc cccgcgcgtt    2400
ggccgattca ttaatgcagc tggcacgaca ggtttcccga ctggaaagca attggcagtg    2460
agcgcaacgc aattaatgtg agttagctca ctcattaggc accccaggct ttacacttta    2520
tgcttccggc tcgtataatg tgtggaatta tgagcggata taatttcac acaggaggtt    2580 taaactttaa acatgtcaaa agagacgtct tttgttaaga atgctgagga acttgcaaag    2640
caaaaaatgg atgctattaa ccctgaactt tcttcaaaat ttaaattttt aataaaattc    2700
ctgtctcagt ttcctgaagc ttgctctaaa cctcgttcaa aaaaaatgca gaataaagtt    2760
ggtcaagagg aacatattga atatttagct cgtagttttc atgagagtcg attgccaaga    2820
aaacccacgc cacctacaac ggttcctgat gaggtggtta gcatagttct taatataagt    2880
tttaatatac agcctgaaaa tcttgagaga ataaaagaag aacatcgatt ttccatggca    2940
gctgagaata ttgtaggaga tcttctagaa agat                                2974
```

```
<210> SEQ ID NO 2
<211> LENGTH: 2725
<212> TYPE: DNA
<213> ORGANISM: Artificial Sequence
<220> FEATURE:
<223> OTHER INFORMATION: pUCBM21 (cloning vector)

<400> SEQUENCE: 2
```

```
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcaccccagg ctttacactt tatgcttccg gctcgtatgt tgtgtggaat     180
tgtgagcgga taacaatttc acacaggaaa cagctatgac catgattacg ccaagcttcc     240
atgggatatc gcatgcctgc agagctctag agtcgacggg cccggtaccg cggccgcact     300
taagttacgc gtggatcccc gggaattcac tggccgtcgt tttacaacgt cgtgactggg     360
aaaaccctgg cgttacccaa cttaatcgcc ttgcagcaca tccccctttc gccagctggc     420
gtaatagcga agaggcccgc accgatcgcc cttcccaaca gttgcgcagc ctgaatggcg     480
aatggcgcct gatgcggtat tttctcctta cgcatctgtg cggtatttca caccgcatat     540
ggtgcactct cagtacaatc tgctctgatg ccgcatagtt aagccagccc cgacacccgc     600
caacacccgc tgacgcgccc tgacgggctt gtctgctccc ggcatccgct tacagacaag     660
ctgtgaccgt ctccgggagc tgcatgtgtc agaggttttc accgtcatca ccgaaacgcg     720
cgagacgaaa gggcctcgtg atacgcctat ttttataggt taatgtcatg ataataatgg     780
tttcttagac gtcaggtggc acttttcggg gaaatgtgcg cggaacccct atttgtttat     840
ttttctaaat acattcaaat atgtatccgc tcatgagaca ataaccctga taatgcttc     900 aataatattg aaaaaggaag agtatgagta ttcaacattt ccgtgtcgcc cttattccct     960 ttttgcggc attttgcctt cctgtttttg ctcacccaga aacgctggtg aaagtaaaag    1020
atgctgaaga tcagttgggt gcacgagtgg gttacatcga actggatctc aacagcggta    1080
```

```
agatccttga gagttttcgc cccgaagaac gttttccaat gatgagcact tttaaagttc      1140
tgctatgtgg cgcggtatta tcccgtattg acgccgggca agagcaactc ggtcgccgca      1200
tacactattc tcagaatgac ttggttgagt actcaccagt cacagaaaag catcttacgg      1260
atggcatgac agtaagagaa ttatgcagtg ctgccataac catgagtgat aacactgcgg      1320
ccaacttact tctgacaacg atcggaggac cgaaggagct aaccgctttt ttgcacaaca      1380
tgggggatca tgtaactcgc cttgatcgtt gggaaccgga gctgaatgaa gccataccaa      1440
acgacgagcg tgacaccacg atgcctgtag caatggcaac aacgttgcgc aaactattaa      1500
ctggcgaact acttactcta gcttcccggc aacaattaat agactggatg gaggcggata      1560
aagttgcagg accacttctg cgctcggccc ttccggctgg ctggtttatt gctgataaat      1620
ctggagcccg tgagcgtggg tctcgcggta tcattgcagc actggggcca gatggtaagc      1680
cctcccgtat cgtagttatc tacacgacgg ggagtcaggc aactatggat gaacgaaata      1740
gacagatcgc tgagataggt gcctcactga ttaagcattg gtaactgtca gaccaagttt      1800
actcatatat actttagatt gatttaaaac ttcatttttt atttaaaagg atctaggtga      1860
agatccttt tgataatctc atgaccaaaa tcccttaacg tgagttttcg ttccactgag      1920
cgtcagaccc cgtagaaaag atcaaaggat cttcttgaga tcctttttt ctgcgcgtaa      1980
tctgctgctt gcaaacaaaa aaaccaccgc taccagcggt ggtttgtttg ccggatcaag      2040
agctaccaac tcttttccg aaggtaactg gcttcagcag agcgcagata ccaaatactg      2100
tccttctagt gtagccgtag ttaggccacc acttcaagaa ctctgtagca ccgcctacat      2160
acctcgctct gctaatcctg ttaccagtgg ctgctgccag tggcgataag tcgtgtctta      2220
ccgggttgga ctcaagacga tagttaccgg ataaggcgca gcggtcgggc tgaacggggg      2280
gttcgtgcac acagcccagc ttggagcgaa cgacctacac cgaactgaga tacctacagc      2340
gtgagctatg agaaagcgcc acgcttcccg aagggagaaa ggcggacagg tatccggtaa      2400
gcggcagggt cggaacagga gagcgcacga gggagcttcc agggggaaac gcctggtatc      2460
tttatagtcc tgtcgggttt cgccacctct gacttgagcg tcgatttttg tgatgctcgt      2520
caggggggcg gagcctatgg aaaaacgcca gcaacgcggc cttttacgg ttcctggcct      2580
tttgctggcc ttttgctcac atgttctttc ctgcgttatc ccctgattct gtggataacc      2640
gtattaccgc ctttgagtga gctgataccg ctcgccgcag ccgaacgacc gagcgcagcg      2700
agtcagtgag cgaggaagcg gaaga                                           2725

<210> SEQ ID NO 3
<211> LENGTH: 9203
<212> TYPE: DNA
<213> ORGANISM: Artificial Sequence
<220> FEATURE:
<223> OTHER INFORMATION: pUC-Lys2-DK2 (source of URA blaster)
<220> FEATURE:
<221> NAME/KEY: CDS
<222> LOCATION: (5937)..(6797)

<400> SEQUENCE: 3
catgcgatat cccatggaag cttggcgtaa tcatggtcat agctgtttcc tgtgtgaaat       60
tgttatccgc tcacaattcc acacaacata cgagccggaa gcataaagtg taaagcctgg      120
ggtgcctaat gagtgagcta actcacatta attgcgttgc gctcactgcc cgctttccag      180
tcgggaaacc tgtcgtgcca gctgcattaa tgaatcggcc aacgcgcggg gagaggcggt      240
ttgcgtattg ggcgctcttc cgcttcctcg ctcactgact cgctgcgctc ggtcgttcgg      300
```

```
ctgcggcgag cggtatcagc tcactcaaag gcggtaatac ggttatccac agaatcaggg      360
gataacgcag gaaagaacat gtgagcaaaa ggccagcaaa aggccaggaa ccgtaaaaag      420
gccgcgttgc tggcgttttt ccataggctc cgcccccctg acgagcatca caaaaatcga      480
cgctcaagtc agaggtggcg aaacccgaca ggactataaa gataccaggc gtttccccct      540
ggaagctccc tcgtgcgctc tcctgttccg accctgccgc ttaccggata cctgtccgcc      600
tttctccctt cgggaagcgt ggcgctttct catagctcac gctgtaggta tctcagttcg      660
gtgtaggtcg ttcgctccaa gctgggctgt gtgcacgaac cccccgttca gcccgaccgc      720
tgcgccttat ccggtaacta tcgtcttgag tccaacccgg taagacacga cttatcgcca      780
ctggcagcag ccactggtaa caggattagc agagcgaggt atgtaggcgg tgctacagag      840
ttcttgaagt ggtggcctaa ctacggctac actagaagga cagtatttgg tatctgcgct      900
ctgctgaagc cagttacctt cggaaaaaga gttggtagct cttgatccgg caaacaaacc      960
accgctggta gcggtggttt ttttgtttgc aagcagcaga ttacgcgcag aaaaaaagga     1020
tctcaagaag atcctttgat cttttctacg ggtctgacg ctcagtggaa cgaaaactca     1080
cgttaaggga ttttggtcat gagattatca aaaaggatct tcacctagat ccttttaaat     1140
taaaaatgaa gttttaaatc aatctaaagt atatatgagt aaacttggtc tgacagttac     1200
caatgcttaa tcagtgaggc acctatctca gcgatctgtc tatttcgttc atccatagtt     1260
gcctgactcc ccgtcgtgta gataactacg atacgggagg gcttaccatc tggccccagt     1320
gctgcaatga taccgcgaga cccacgctca cgggctccag atttatcagc aataaaccag     1380
ccagccggaa gggccgagcg cagaagtggt cctgcaactt tatccgcctc catccagtct     1440
attaattgtt gccgggaagc tagagtaagt agttcgccag ttaatagttt gcgcaacgtt     1500
gttgccattg ctacaggcat cgtggtgtca cgctcgtcgt ttggtatggc ttcattcagc     1560
tccggttccc aacgatcaag gcgagttaca tgatccccca tgttgtgcaa aaaagcggtt     1620
agctccttcg gtcctccgat cgttgtcaga agtaagttgg ccgcagtgtt atcactcatg     1680
gttatggcag cactgcataa ttctcttact gtcatgccat ccgtaagatg cttttctgtg     1740
actggtgagt actcaaccaa gtcattctga gaatagtgta tgcggcgacc gagttgctct     1800
tgcccggcgt caatacggga taataccgcg ccacatagca gaactttaaa agtgctcatc     1860
attggaaaac gttcttcggg gcgaaaactc tcaaggatct taccgctgtt gagatccagt     1920
tcgatgtaac ccactcgtgc acccaactga tcttcagcat cttttacttt caccagcgtt     1980
tctgggtgag caaaaacagg aaggcaaaat gccgcaaaaa agggaataag ggcgacacgg     2040
aaatgttgaa tactcatact cttccttttt caatattatt gaagcattta tcagggttat     2100
tgtctcatga gcggatacat atttgaatgt atttagaaaa ataaacaaat aggggttccg     2160
cgcacatttc cccgaaaagt gccacctgac gtctaagaaa ccattattat catgacatta     2220
acctataaaa ataggcgtat cacgaggccc tttcgtctcg cgcgtttcgg tgatgacggt     2280
gaaaacctct gacacatgca gctcccggag acggtcacag cttgtctgta agcggatgcc     2340
gggagcagac aagcccgtca gggcgcgtca gcgggtgttg gcgggtgtcg ggctggctt      2400 aactatgcgg catcagagca gattgtactg agagtgcacc atatgcggtg tgaaataccg     2460
cacagatgcg taaggagaaa ataccgcatc aggcgccaac gccgagaagg agtggaacga     2520
gctcttcgcc aagtacggta aggagtatcc caaggagcac tctgagatca tccgacgatt     2580
caagcgagag ctgcccgagg gatgggagaa ggctctgcct acctacaccc cgccgacaa      2640 tgccgttgct tctcgaaagc tgtccgagat tgtcctcacc aagatccacg aggtcctccc     2700
```

```
cgagcttgtt ggtggttccg ccgatctgac cggctcaaac ctgacccgat ggaaggacgc    2760
tgttgatttc cagcctcctg tcacccacct tggtgactac tccggccgat atatccgata    2820
cggtgttcga gagcacggca tgggcgctat catgaacggt atgaacgctt acggaggtat    2880
catcccctac ggaggtactt tccttaactt cgtctcctac gccgctggtg ccgtccgact    2940
gtctgccctg tctggccacc acgttatctg ggttgctacc catgactcca ttggtctggg    3000
tgaggatggc cctacccatc agcccattga gactgtcgcc tggctccgag ccaccccaa    3060 cctctctgtg tggcgacctg ccgacggtaa cgagacctcc gctgcttact acaaggccat    3120
caccaactac cacactccct ctgtcctgtc tctgacccga cagaacctgc ctcagcttga    3180
gggctcttcc atcgagaagg cctccaaggg tggttaccag ctcatctccg aggacaaggg    3240
tgacatctac cttgtgtcca ctggttctga ggttgccatc tgtgttgctg ccgccaagct    3300
cctcaaggag aagaagggta tcactgccgg tgtcatctct ctgcccgact ggttcacctt    3360
cgagcagcag tctctcgagt accgaaagtc tgttttcccc gatggcatcc ccatgctttc    3420
cgtcgaggtc tactccgact ttggctggtc tcgatactct caccagcagt ttggtctgga    3480
ccgattcggt gcttctgctc ccttccagca ggtctacgat gcctttgagt tcaatgccga    3540
gggtgtcgcc aagcgagctg aggccaccat taactactac aagggccaga ctgtcaagtc    3600
tcctattcag cgagccttcg acccccattga cgtcaacacc cgaccggcc acggtgtcta    3660 agtgggttgc ccgtctgata taagtattga tatagagtat atttaaatgg aaccccatga    3720
gtttgtagaa ccttgcgtga caactggcat gtatgtgatg tcactgatag ttgtattgcc    3780
gtatgtaact attacgagtt ctggggatga gattcccatg cttccacttg ctcatcagca    3840
aacgctatca aatttacgct caattttttga gcactggcta caatacaaac catctcaaac    3900
gaaaaatgct gtaattattg cgacacctca catttagtca tatatatcat aattaattaa    3960
atcatacaaa aatagtctgc tcacagacaa gcaataatca ccattacacg gtaacaaata    4020
acaaaatggc aatgcttcgc atcgccttat ggtcaaggca ctccctacgg cactgcttac    4080
ttgttaccac cacgtccacc gacactcttc agcttatcaa gggtctgctc agacagctcc    4140
accttcggca aagcaagctc aaccttggac tgggggcat ccaggaagcc gacagccacc    4200
aggtaagcca ggtagatacc catttgagcc tcgtcaacgc ccttaccagc ggacaaatcg    4260
actccggtcc actcagcgtc tcgagagaga gcagatcgag cattggagtc atccagctcg    4320
ggggccttgg tagactgggg aaggtcatcg agcacaaagt gtagcagagg atacagggca    4380
gagtcctgcg agtcctcaac aacaaacttc tccagagcca gacgccaggt gacgtagtcc    4440
tcgacagaaa ctttgtaacc gtacttctgg agggtctgca ggaattcgtt gaaccgtgtt    4500
cgaggctggg aagtcacatg ggcgacaacc acgccgaag gctgcttggg ccagaaagag    4560
gcggcagtaa caacccgagc cacgtgatcg acgggcacca tgttgaccga gttgtggatg    4620
ttgggaatct cacccagctg gatgcatccc ttgatcattc gaaccaggaa atcgtccgtg    4680
ttggtggctc cggtcttgga gtctccgaca acgtaaccag gtcgaatgat ggttccggtg    4740
agtccccggg ctccggcctc tcggatcacg tgctctgcga cccacttgga ctgtccgtag    4800
ccgttgccga gacccacaga agaacccatg agatcgtcgg actcgggaac gccagccttg    4860
ccctcctcca ccagatcggc agacagcttg ttgaagtgct cggtgtcgac ggcagaggtg    4920
gaggacacaa agttgaagat ctactgggct gcttcctaat gcaggagtcg cataaggag    4980 agcgtcgacc gatgcccttg agagccttca acccagtcag ctccttccgg tgggcgcggg    5040
```

| | |
|---|---|
| gcatgactat cgtcgccgca cttatgactg tcttctttat catgcaactc gtaggacagg | 5100 |
| tgccggcagc gctctgggtc attttcggcg aggaccgctt tcgctggagc gcgacgatga | 5160 |
| tcggcctgtc gcttgcggta ttcggaatct tgcacgccct cgctcaagcc ttcgtcactg | 5220 |
| gtcccgccac caaacgtttc ggcgagaagc aggccattat cgccggcatg gcggccgacg | 5280 |
| cgctgggcta cgtcttgctg gcgttcgcga cgcgaggctg gatggccttc cccattatga | 5340 |
| ttcttctcgc ttccggcggc atcgggatgc ccgcgttgca ggccatgctg tccaggcagg | 5400 |
| tagatgacga ccatcaggga cagcttcaag gatcgctcgc ggctcttacc agcctaactt | 5460 |
| cgatcactgg accgctgatc gtcacggcga tttatgccgc ctcggcgagc acatggaacg | 5520 |
| ggttggcatg gattgtaggc gccgccctat accttgtctg cctcctgtct gactcgtcat | 5580 |
| tgccgccttt ggagtacgac tccaactatg agtgtgcttg gatcactttg acgatacatt | 5640 |
| cttcgttgga ggctgtgggt ctgacagctg cgttttcggc gcggttggcc gacaacaata | 5700 |
| tcagctgcaa cgtcattgct ggctttcatc atgatcacat ttttgtcggc aaaggcgacg | 5760 |
| cccagagagc cattgacgtt ctttctaatt tggaccgata gccgtatagt ccagtctatc | 5820 |
| tataagttca actaactcgt aactattacc ataacatata cttcactgcc ccagataagg | 5880 |
| ttccgataaa aagttctgca gactaaattt atttcagtct cctcttcacc accaaa atg<br>                                                    Met<br>                                                    1 | 5939 |
| ccc tcc tac gaa gct cga gct aac gtc cac aag tcc gcc ttt gcc gct<br>Pro Ser Tyr Glu Ala Arg Ala Asn Val His Lys Ser Ala Phe Ala Ala<br>     5          10          15 | 5987 |
| cga gtg ctc aag ctc gtg gca gcc aag aaa acc aac ctg tgt gct tct<br>Arg Val Leu Lys Leu Val Ala Ala Lys Lys Thr Asn Leu Cys Ala Ser<br>   20          25          30 | 6035 |
| ctg gat gtt acc acc acc aag gag ctc att gag ctt gcc gat aag gtc<br>Leu Asp Val Thr Thr Thr Lys Glu Leu Ile Glu Leu Ala Asp Lys Val<br>35          40          45 | 6083 |
| gga cct tat gtg tgc atg atc aag acc cat atc gac atc att gac gac<br>Gly Pro Tyr Val Cys Met Ile Lys Thr His Ile Asp Ile Ile Asp Asp<br>50          55          60          65 | 6131 |
| ttc acc tac gcc ggc act gtg ctc ccc ctc aag gaa ctt gct ctt aag<br>Phe Thr Tyr Ala Gly Thr Val Leu Pro Leu Lys Glu Leu Ala Leu Lys<br>        70          75          80 | 6179 |
| cac ggt ttc ttc ctg ttc gag gac aga aag ttc gca gat att ggc aac<br>His Gly Phe Phe Leu Phe Glu Asp Arg Lys Phe Ala Asp Ile Gly Asn<br>          85          90          95 | 6227 |
| act gtc aag cac cag tac aag aac ggt gtc tac cga atc gcc gag tgg<br>Thr Val Lys His Gln Tyr Lys Asn Gly Val Tyr Arg Ile Ala Glu Trp<br>100         105         110 | 6275 |
| tcc gat atc acc aac gcc cac ggt gta ccc gga acc gga atc att gct<br>Ser Asp Ile Thr Asn Ala His Gly Val Pro Gly Thr Gly Ile Ile Ala<br>   115         120         125 | 6323 |
| ggc ctg cga gct ggt gcc gag gaa act gtc tct gaa cag aag aag gag<br>Gly Leu Arg Ala Gly Ala Glu Glu Thr Val Ser Glu Gln Lys Lys Glu<br>130         135        140        145 | 6371 |
| gac gtc tct gac tac gag aac tcc cag tac aag gag ttc ctg gtc ccc<br>Asp Val Ser Asp Tyr Glu Asn Ser Gln Tyr Lys Glu Phe Leu Val Pro<br>        150         155         160 | 6419 |
| tct ccc aac gag aag ctg gcc aga ggt ctg ctc atg ctg gcc gag ctg<br>Ser Pro Asn Glu Lys Leu Ala Arg Gly Leu Leu Met Leu Ala Glu Leu<br>          165         170        175 | 6467 |
| tct tgc aag ggc tct ctg gcc act ggc gag tac tcc aag cag acc att<br>Ser Cys Lys Gly Ser Leu Ala Thr Gly Glu Tyr Ser Lys Gln Thr Ile<br>   180         185        190 | 6515 |

| | | | | | | | | | | | | | | |
|---|---|---|---|---|---|---|---|---|---|---|---|---|---|---|
| gag | ctt | gcc | cga | tcc | gac | ccc | gag | ttt | gtg | gtt | ggc | ttc | att | gcc cag | 6563
| Glu | Leu | Ala | Arg | Ser | Asp | Pro | Glu | Phe | Val | Val | Gly | Phe | Ile | Ala Gln |
| | 195 | | | | 200 | | | | | 205 | | | | |

```
gag ctt gcc cga tcc gac ccc gag ttt gtg gtt ggc ttc att gcc cag    6563
Glu Leu Ala Arg Ser Asp Pro Glu Phe Val Val Gly Phe Ile Ala Gln
    195                 200                 205 aac cga cct aag ggc gac tct gag gac tgg ctt att ctg acc ccc ggg    6611
Asn Arg Pro Lys Gly Asp Ser Glu Asp Trp Leu Ile Leu Thr Pro Gly
210                 215                 220                 225 gtg ggt ctt gac gac aag gga gac gct ctc gga cag cag tac cga act    6659
Val Gly Leu Asp Asp Lys Gly Asp Ala Leu Gly Gln Gln Tyr Arg Thr
                230                 235                 240 gtt gag gat gtc atg tct acc gga acg gat atc ata att gtc ggc cga    6707
Val Glu Asp Val Met Ser Thr Gly Thr Asp Ile Ile Ile Val Gly Arg
            245                 250                 255 ggt ctg tac ggc cag aac cga gat cct att gag gag gcc aag cga tac    6755
Gly Leu Tyr Gly Gln Asn Arg Asp Pro Ile Glu Glu Ala Lys Arg Tyr
        260                 265                 270 cag aag gct ggc tgg gag gct tac cag aag att aac tgt tag            6797
Gln Lys Ala Gly Trp Glu Ala Tyr Gln Lys Ile Asn Cys
    275                 280                 285 aggttagact atggatatgt catttaactg tgtatataga gagcgtgcaa gtatggagcg   6857
cttgttcagc ttgtatgatg gtcagacgac ctgtctgatc gagtatgtat gatactgcac   6917
aacctgtgta tccgcatgat ctgtccaatg gggcatgttg ttgtgtttct cgatacggag   6977
atgctgggta caagtagcta atacgattga actacttata cttatatgag gcttgaagaa   7037
agctgacttg tgtatgactt attctcaact acatccccag tcacaatacc accagaattc   7097
tactgggctg cttcctaatg caggagtcgc ataaggggaga cgtcgaccg atgcccttga   7157 gagccttcaa cccagtcagc tccttccggt gggcgcgggg catgactatc gtcgccgcac   7217
ttatgactgt cttctttatc atgcaactcg taggacaggt gccggcagcg ctctgggtca   7277
ttttcggcga ggaccgcttt cgctggagcg cgacgatgat cggcctgtcg cttgcggtat   7337
tcggaatctt gcacgccctc gctcaagcct tcgtcactgg tcccgccacc aaacgtttcg   7397
gcgagaagca ggccattatc gccggcatgg cggccgacgc gctgggctac gtcttgctgg   7457
cgttcgcgac gcgaggctgg atggccttcc ccattatgat tcttctcgct tccggcggca   7517
tcgggatgcc cgcgttgcag gccatgctgt ccaggcaggt agatgacgac catcagggac   7577
agcttcaagg atcgctcgcg gctcttacca gcctaacttc gatcactgga ccgctgatcg   7637
tcacggcgat ttatgccgcc tcggcagca catggaacgg gttggcatgg attgtaggcg    7697
ccgccctata ccttgtctgc ctggatctcc agttctgtac agccgatccc ggggacccctt   7757 gtagaactct ctccaggcct cacccttgtt gaccttctcg tcctcctgga tccgagacac   7817
acgtcctcgt cgcccgagag acggtagacg agaatggcgt agagagccag agctgcagag   7877
aaatcagtag cgcctgctac accgctgttc ttggcaatct gatcgagctc ggccacggtc   7937
ttggagctaa gagcctccgt caattgtgct tcgactacac tgccttcagc ggggcggacg   7997
aaatcgaacg ggaggactga gagtgtgggg ttggtaaggg cggttgccca ttgtgttact   8057
gtattagtac ggtacatagg gccgaaggtc agagcggacc taataaatag ctgacacaga   8117
ataagtaccc tttctttgtc caggtcatga gtctcggtat cacgtcttaa aagagtcctg   8177
ccgttgtcca tgagtatagt atagcagaca acatagtatt catactgcga tgacggcggg   8237
aattggaggc tacagaactc gaagcgggt catatagaca atcgcatttg ccaacgagtg   8297
tctgattaag gcttctccgt gtgactgctc attgtgtcaa tgctatactg tagtcatagc   8357
tacattgaca gaaagacaac gacagacagt gataaagtaa ccagatcctc aatcaaaaga   8417
```

```
gccgcaatga tccatttctc atatcgcata ccatccactc tgtttgtgcc gcatcctcca    8477
caacgatttg ctcatggcac tgttctggtc agatcagaca tcggtagaca caatccagat    8537
gacagttcac agacgattga tctcaatttt aagcctgacc aagcgatctc acgaacgatt    8597
ccttcaattt cccatggata ctcacacgac attgtcggta gttttttttt tttgtagaga    8657
caagttttca aacagatgtc aaaaccgaaa gttgcaagct ttcgatttgg aaggttatat    8717
cgagacaggt gcactgagtc atactgcagt ggagtgcagc tgatgggggg tgatcaaaga    8777
aaatggtcac gtgattttac tgacctatag atattatcac tgcaaatgca gatgacataa    8837
taaatcatac cacgagctcc gcaccccaac tatacccctaa ccctacagtc ttctgaaaaa    8897
cctgatctgt gaacacagac cccaacccgg acaaggcttg aaccgctact cgtacagtac    8957
atctccaagg tgggttgatg tgcagagcga tgtcattaat gacaggctgt ggttggctgt    9017
ggtatcaaat gataaagtga taaaaatttg agacacggtt acagattatg agcaacaagg    9077
aggaatcagg gagatgaatg ggagtaagtt gtggtctcaa tgagtggaac agttgacttt    9137
tatacagact aatcatagct tcttgcagtc tcattattat gggctctgta acacattcta    9197
ttgaag                                                               9203
```

<210> SEQ ID NO 4
<211> LENGTH: 286
<212> TYPE: PRT
<213> ORGANISM: Artificial Sequence
<220> FEATURE:
<223> OTHER INFORMATION: Synthetic Construct

<400> SEQUENCE: 4

```
Met Pro Ser Tyr Glu Ala Arg Ala Asn Val His Lys Ser Ala Phe Ala
1               5                   10                  15

Ala Arg Val Leu Lys Leu Val Ala Lys Lys Thr Asn Leu Cys Ala
            20                  25                  30

Ser Leu Asp Val Thr Thr Thr Lys Glu Leu Ile Glu Leu Ala Asp Lys
        35                  40                  45

Val Gly Pro Tyr Val Cys Met Ile Lys Thr His Ile Asp Ile Ile Asp
    50                  55                  60

Asp Phe Thr Tyr Ala Gly Thr Val Leu Pro Leu Lys Glu Leu Ala Leu
65                  70                  75                  80

Lys His Gly Phe Phe Leu Phe Glu Asp Arg Lys Phe Ala Asp Ile Gly
                85                  90                  95

Asn Thr Val Lys His Gln Tyr Lys Asn Gly Val Tyr Arg Ile Ala Glu
            100                 105                 110

Trp Ser Asp Ile Thr Asn Ala His Gly Val Pro Gly Thr Gly Ile Ile
        115                 120                 125

Ala Gly Leu Arg Ala Gly Ala Glu Glu Thr Val Ser Glu Gln Lys Lys
    130                 135                 140

Glu Asp Val Ser Asp Tyr Glu Asn Ser Gln Tyr Lys Glu Phe Leu Val
145                 150                 155                 160

Pro Ser Pro Asn Glu Lys Leu Ala Arg Gly Leu Leu Met Leu Ala Glu
                165                 170                 175

Leu Ser Cys Lys Gly Ser Leu Ala Thr Gly Glu Tyr Ser Lys Gln Thr
            180                 185                 190

Ile Glu Leu Ala Arg Ser Asp Pro Glu Phe Val Val Gly Phe Ile Ala
        195                 200                 205

Gln Asn Arg Pro Lys Gly Asp Ser Glu Asp Trp Leu Ile Leu Thr Pro
    210                 215                 220
```

```
Gly Val Gly Leu Asp Asp Lys Gly Asp Ala Leu Gly Gln Gln Tyr Arg
225                 230                 235                 240

Thr Val Glu Asp Val Met Ser Thr Gly Thr Asp Ile Ile Ile Val Gly
            245                 250                 255

Arg Gly Leu Tyr Gly Gln Asn Arg Asp Pro Ile Glu Glu Ala Lys Arg
        260                 265                 270

Tyr Gln Lys Ala Gly Trp Glu Ala Tyr Gln Lys Ile Asn Cys
    275                 280                 285

<210> SEQ ID NO 5
<211> LENGTH: 10839
<212> TYPE: DNA
<213> ORGANISM: Artificial Sequence
<220> FEATURE:
<223> OTHER INFORMATION: pINTB-HMG1 (cloning vector)
<220> FEATURE:
<221> NAME/KEY: CDS
<222> LOCATION: (207)..(3206)
<223> OTHER INFORMATION: 3-methyl-glutaryl-CoA reductase (HMG1) gene

<400> SEQUENCE: 5
ctagtttctt tgtctggcca tccgggtaac ccatgccgga cgcaaaatag actactgaaa      60 attttttgc tttgtggttg ggactttagc caagggtata aagaccacc gtccccgaat       120 taccttcct cttcttttct ctctctcctt gtcaactcac acccgaaatc gttaagcatt     180
```

| | | | | |
|---|---|---|---|---|
| tccttctgag tataagaatc attcaa atg cta caa gca gct att gga aag att | | | | | 233 |
| | Met Leu Gln Ala Ala Ile Gly Lys Ile | | | |
| | 1 | 5 | | |

```
gtg gga ttt gcg gtc aac cga ccc atc cac aca gtt gtc ctg acg tcc       281
Val Gly Phe Ala Val Asn Arg Pro Ile His Thr Val Val Leu Thr Ser
10              15                  20                  25 atc gtg gcg tca acc gca tac ctc gcc atc ctc gac att gcc atc ccg       329
Ile Val Ala Ser Thr Ala Tyr Leu Ala Ile Leu Asp Ile Ala Ile Pro
            30                  35                  40 ggt ttc gag ggc aca caa ccc atc tca tac tac cac cct gca gca aaa       377
Gly Phe Glu Gly Thr Gln Pro Ile Ser Tyr Tyr His Pro Ala Ala Lys
        45                  50                  55 tct tac gac aac cct gct gat tgg acc cac att gca gag gcc gac atc       425
Ser Tyr Asp Asn Pro Ala Asp Trp Thr His Ile Ala Glu Ala Asp Ile
    60                  65                  70 cct tca gac gcc tac cga ctt gca ttt gcc cag atc cgt gtc agt gat       473
Pro Ser Asp Ala Tyr Arg Leu Ala Phe Ala Gln Ile Arg Val Ser Asp
75                  80                  85 gtt cag ggc gga gag gcc ccc acc atc cct ggc gcc gtg gcc gtg tct       521
Val Gln Gly Gly Glu Ala Pro Thr Ile Pro Gly Ala Val Ala Val Ser
90                  95                  100                 105 gat ctc gac cac aga atc gtc atg gac tac aaa cag tgg gcc ccc tgg       569
Asp Leu Asp His Arg Ile Val Met Asp Tyr Lys Gln Trp Ala Pro Trp
            110                 115                 120 acc gcc agc aac gag cag atc gcc tcg gag aac cac atc tgg aag cac       617
Thr Ala Ser Asn Glu Gln Ile Ala Ser Glu Asn His Ile Trp Lys His
        125                 130                 135 tcc ttc aag gac cac gtg gcc ttc agc tgg atc aag tgg ttc cga tgg       665
Ser Phe Lys Asp His Val Ala Phe Ser Trp Ile Lys Trp Phe Arg Trp
    140                 145                 150 gcc tac ctg cgt ttg tcc act ctc atc cag ggg gca gac aac ttc gac       713
Ala Tyr Leu Arg Leu Ser Thr Leu Ile Gln Gly Ala Asp Asn Phe Asp
155                 160                 165 att gcc gtg gtc gcc ctt ggc tat ctt gcc atg cac tac acc ttc ttc       761
Ile Ala Val Val Ala Leu Gly Tyr Leu Ala Met His Tyr Thr Phe Phe
```

```
                                                                          -continued 170                 175                 180                 185
agt ctc ttc cga tcc atg cga aag gtt ggc tcg cac ttt tgg ctt gcc           809
Ser Leu Phe Arg Ser Met Arg Lys Val Gly Ser His Phe Trp Leu Ala
                190                 195                 200 tcc atg gct ctg gtc tct tcc acc ttc gct ttc ctg ctt gcg gtg gtg           857
Ser Met Ala Leu Val Ser Ser Thr Phe Ala Phe Leu Leu Ala Val Val
            205                 210                 215 gct tcc tct agc ctg ggt tac cga cct agc atg atc acc atg tcc gag           905
Ala Ser Ser Ser Leu Gly Tyr Arg Pro Ser Met Ile Thr Met Ser Glu
        220                 225                 230 ggc ctg ccc ttc ctc gtg gtc gcc att ggc ttt gac cga aag gtc aac           953
Gly Leu Pro Phe Leu Val Val Ala Ile Gly Phe Asp Arg Lys Val Asn
    235                 240                 245 ctg gct agc gag gtg ctc aca tcc aag agc agc cag ctc gct ccc atg          1001
Leu Ala Ser Glu Val Leu Thr Ser Lys Ser Ser Gln Leu Ala Pro Met
250                 255                 260                 265 gtg cag gtg atc aca aag atc gcc tcc aag gcg ctg ttt gag tac agc          1049
Val Gln Val Ile Thr Lys Ile Ala Ser Lys Ala Leu Phe Glu Tyr Ser
                270                 275                 280 ctt gag gtg gcc gcc ctg ttt gct ggc gcc tat acc gga gtt cct cga          1097
Leu Glu Val Ala Ala Leu Phe Ala Gly Ala Tyr Thr Gly Val Pro Arg
            285                 290                 295 ctg tcc cag ttt tgc ttc tta tct gct tgg atc ctc atc ttc gac tac          1145
Leu Ser Gln Phe Cys Phe Leu Ser Ala Trp Ile Leu Ile Phe Asp Tyr
        300                 305                 310 atg ttt ttg ctg acc ttc tac tct gct gtc ctt gct atc aag ttt gag          1193
Met Phe Leu Leu Thr Phe Tyr Ser Ala Val Leu Ala Ile Lys Phe Glu
    315                 320                 325 atc aat cac att aag cga aac cga atg atc cag gat gct ctc aag gag          1241
Ile Asn His Ile Lys Arg Asn Arg Met Ile Gln Asp Ala Leu Lys Glu
330                 335                 340                 345 gat ggt gta tct gct gct gtt gcc gag aag gta gcc gac tct tct ccc          1289
Asp Gly Val Ser Ala Ala Val Ala Glu Lys Val Ala Asp Ser Ser Pro
                350                 355                 360 gac gcc aag ctc gac cga aag tcc gac gtt tct ctt ttt gga gcc tct          1337
Asp Ala Lys Leu Asp Arg Lys Ser Asp Val Ser Leu Phe Gly Ala Ser
            365                 370                 375 ggc gcc att gcg gtg ttc aag atc ttc atg gtc ctt ggg ttc ctt ggt          1385
Gly Ala Ile Ala Val Phe Lys Ile Phe Met Val Leu Gly Phe Leu Gly
        380                 385                 390 ctc aac ctc atc aac ctg act gcc atc cct cac ctt ggc aag gcg gcc          1433
Leu Asn Leu Ile Asn Leu Thr Ala Ile Pro His Leu Gly Lys Ala Ala
    395                 400                 405 gcc gct gcc cag tct gtg act ccc atc acc ctc tcc ccc gag ctt ctc          1481
Ala Ala Ala Gln Ser Val Thr Pro Ile Thr Leu Ser Pro Glu Leu Leu
410                 415                 420                 425 cat gcc atc ccc gcc tct gtg ccc gtt gtc acc ttt gtg ccc agc              1529
His Ala Ile Pro Ala Ser Val Pro Val Val Thr Phe Val Pro Ser
                430                 435                 440 gtt gtg tac gag cac tcc cag ctc att ctg cag ctg gag gac gcc ctc          1577
Val Val Tyr Glu His Ser Gln Leu Ile Leu Gln Leu Glu Asp Ala Leu
            445                 450                 455 act acc ttc ctg gct gcc tgc tcc aaa act att ggt gac ccc gtc atc          1625
Thr Thr Phe Leu Ala Ala Cys Ser Lys Thr Ile Gly Asp Pro Val Ile
        460                 465                 470 tcc aag tac atc ttc ctg tgc ctg atg gtc tcc acc gcc ctg aac gtc          1673
Ser Lys Tyr Ile Phe Leu Cys Leu Met Val Ser Thr Ala Leu Asn Val
    475                 480                 485 tac ctg ttt gga gcc acc cga gaa gtt gtg cga acc cag tct gtg aag          1721
```

```
            Tyr Leu Phe Gly Ala Thr Arg Glu Val Val Arg Thr Gln Ser Val Lys
            490                 495                 500                 505 gtg gtt gag aag cac gtt cct atc gtc att gag aag ccc agc gag aag         1769
Val Val Glu Lys His Val Pro Ile Val Ile Glu Lys Pro Ser Glu Lys
                    510                 515                 520 gag gag gac acc tct tct gaa gac tcc att gag ctg act gtc gga aag         1817
Glu Glu Asp Thr Ser Ser Glu Asp Ser Ile Glu Leu Thr Val Gly Lys
                525                 530                 535 cag ccc aag ccc gtg acc gag acc cgt tct ctg gac gac cta gag gct         1865
Gln Pro Lys Pro Val Thr Glu Thr Arg Ser Leu Asp Asp Leu Glu Ala
            540                 545                 550 atc atg aag gca ggt aag acc aag ctt ctg gag gac cac gag gtt gtc         1913
Ile Met Lys Ala Gly Lys Thr Lys Leu Leu Glu Asp His Glu Val Val
        555                 560                 565 aag ctc tct ctc gag ggc aag ctt cct ttg tat gct ctt gag aag cag         1961
Lys Leu Ser Leu Glu Gly Lys Leu Pro Leu Tyr Ala Leu Glu Lys Gln
570                 575                 580                 585 ctt ggt gac aac acc cga gct gtt ggc atc cga cga tct atc atc tcc         2009
Leu Gly Asp Asn Thr Arg Ala Val Gly Ile Arg Arg Ser Ile Ile Ser
                590                 595                 600 cag cag tct aat acc aag act tta gag acc tca aag ctt cct tac ctg         2057
Gln Gln Ser Asn Thr Lys Thr Leu Glu Thr Ser Lys Leu Pro Tyr Leu
            605                 610                 615 cac tac gac tac gac cgt gtt ttt gga gcc tgt tgc gag aac gtt att         2105
His Tyr Asp Tyr Asp Arg Val Phe Gly Ala Cys Cys Glu Asn Val Ile
        620                 625                 630 ggt tac atg cct ctc ccc gtt ggt gtt gct ggc ccc atg aac att gat         2153
Gly Tyr Met Pro Leu Pro Val Gly Val Ala Gly Pro Met Asn Ile Asp
635                 640                 645 ggc aag aac tac cac att cct atg gcc acc act gag ggt tgt ctt gtt         2201
Gly Lys Asn Tyr His Ile Pro Met Ala Thr Thr Glu Gly Cys Leu Val
650                 655                 660                 665 gcc tca acc atg cga ggt tgc aag gcc atc aac gcc ggt ggt ggt gtt         2249
Ala Ser Thr Met Arg Gly Cys Lys Ala Ile Asn Ala Gly Gly Gly Val
                670                 675                 680 acc act gtg ctt act cag gac ggt atg aca cga ggt cct tgt gtt tcc         2297
Thr Thr Val Leu Thr Gln Asp Gly Met Thr Arg Gly Pro Cys Val Ser
            685                 690                 695 ttc ccc tct ctc aag cgg gct gga gcc gct aag atc tgg ctt gat tcc         2345
Phe Pro Ser Leu Lys Arg Ala Gly Ala Ala Lys Ile Trp Leu Asp Ser
        700                 705                 710 gag gag ggt ctc aag tcc atg cga aag gcc ttc aac tcc acc tct cga         2393
Glu Glu Gly Leu Lys Ser Met Arg Lys Ala Phe Asn Ser Thr Ser Arg
715                 720                 725 ttt gct cgt ctc cag tct ctt cac tct acc ctt gct ggt aac ctg ctg         2441
Phe Ala Arg Leu Gln Ser Leu His Ser Thr Leu Ala Gly Asn Leu Leu
730                 735                 740                 745 ttt att cga ttc cga acc acc act ggt gat gcc atg ggc atg aac atg         2489
Phe Ile Arg Phe Arg Thr Thr Thr Gly Asp Ala Met Gly Met Asn Met
                750                 755                 760 atc tcc aag ggc gtc gaa cac tct ctg gcc gtc atg gtc aag gag tac         2537
Ile Ser Lys Gly Val Glu His Ser Leu Ala Val Met Val Lys Glu Tyr
            765                 770                 775 ggc ttc cct gat atg gac att gtg tct gtc tcg ggt aac tac tgc act         2585
Gly Phe Pro Asp Met Asp Ile Val Ser Val Ser Gly Asn Tyr Cys Thr
        780                 785                 790 gac aag aag ccc gca gcg atc aac tgg atc gaa ggc cga ggc aag agt         2633
Asp Lys Lys Pro Ala Ala Ile Asn Trp Ile Glu Gly Arg Gly Lys Ser
795                 800                 805
```

| | |
|---|---|
| gtt gtt gcc gaa gcc acc atc cct gct cac att gtc aag tct gtt ctc<br>Val Val Ala Glu Ala Thr Ile Pro Ala His Ile Val Lys Ser Val Leu<br>810                       815                   820                 825 | 2681 |
| aaa agt gag gtt gac gct ctt gtt gag ctc aac atc agc aag aat ctg<br>Lys Ser Glu Val Asp Ala Leu Val Glu Leu Asn Ile Ser Lys Asn Leu<br>                       830                   835                   840 | 2729 |
| atc ggt agt gcc atg gct ggc tct gtg gga ggt ttc aat gca cac gcc<br>Ile Gly Ser Ala Met Ala Gly Ser Val Gly Gly Phe Asn Ala His Ala<br>                       845                   850                   855 | 2777 |
| gca aac ctg gtg acc gcc atc tac ctt gcc act ggc cag gat cct gct<br>Ala Asn Leu Val Thr Ala Ile Tyr Leu Ala Thr Gly Gln Asp Pro Ala<br>               860                   865                   870 | 2825 |
| cag aat gtc gag tct tcc aac tgc atc acg ctg atg agc aac gtc gac<br>Gln Asn Val Glu Ser Ser Asn Cys Ile Thr Leu Met Ser Asn Val Asp<br>     875                   880                   885 | 2873 |
| ggt aac ctg ctc atc tcc gtt tcc atg cct tct atc gag gtc ggt acc<br>Gly Asn Leu Leu Ile Ser Val Ser Met Pro Ser Ile Glu Val Gly Thr<br>890                       895                   900                   905 | 2921 |
| att ggt gga ggt act att ttg gag ccc cag ggg gct atg ctg gag atg<br>Ile Gly Gly Gly Thr Ile Leu Glu Pro Gln Gly Ala Met Leu Glu Met<br>                       910                   915                   920 | 2969 |
| ctt ggc gtg cga ggt cct cac atc gag acc ccc ggt gcc aac gcc caa<br>Leu Gly Val Arg Gly Pro His Ile Glu Thr Pro Gly Ala Asn Ala Gln<br>             925                   930                   935 | 3017 |
| cag ctt gct cgc atc att gct tct gga gtt ctt gca gcg gag ctt tcg<br>Gln Leu Ala Arg Ile Ile Ala Ser Gly Val Leu Ala Ala Glu Leu Ser<br>          940                   945                   950 | 3065 |
| ctg tgt tct gct ctt gct gcc ggc cat ctt gtg caa agt cat atg acc<br>Leu Cys Ser Ala Leu Ala Ala Gly His Leu Val Gln Ser His Met Thr<br>955                       960                   965 | 3113 |
| cac aac cgg tcc cag gct cct act ccg gcc aag cag tct cag gcc gat<br>His Asn Arg Ser Gln Ala Pro Thr Pro Ala Lys Gln Ser Gln Ala Asp<br>970                       975                   980                   985 | 3161 |
| ctg cag cgt cta caa aac ggt tcg aat att tgc ata cgg tca tag<br>Leu Gln Arg Leu Gln Asn Gly Ser Asn Ile Cys Ile Arg Ser<br>                       990                   995 | 3206 |
| gcatgcaagc tttaagcagt ttgtttagca aaatatattt aacgagtttg atagaggcgc | 3266 |
| tggactacat cattactgaa tcacgcgtac atgtctcagc tcaaattgta tcacggtttc | 3326 |
| tttgtagcaa tggagggga gagttgacaa ggcattagag aagagagcga gaggagaaga | 3386 |
| caagtggata gacgactgca atcatatgat ctgcacaaac tgcgatgttt tcctgtcaga | 3446 |
| tcatgttctt ttgctcatag ttaagctatc gtgactttac ggatccagga ggacgagaag | 3506 |
| gtcaacaagg gtgaggcctg gagagagttc tacaagggtc cccgggatcg gctgtacaga | 3566 |
| actgagatc caggcagaca aggtataggg cggcgcctac aatccatgcc aacccgttcc | 3626 |
| atgtgctcgc cgaggcggca taatcgccg tgacgatcag cggtccagtg atcgaagtta | 3686 |
| ggctggtaag agccgcgagc gatccttgaa gctgtccctg atggtcgtca tctacctgcc | 3746 |
| tggacagcat ggcctgcaac gcgggcatcc cgatgccgcc ggaagcgaga agaatcataa | 3806 |
| tggggaaggc catccagcct cgcgtcgcga acgccagcaa gacgtagccc agcgcgtcgg | 3866 |
| ccgccatgcc ggcgataatg gcctgcttct cgccgaaacg tttggtggcg ggaccagtga | 3926 |
| cgaaggcttg agcgagggcg tgcaagattc cgaataccgc aagcgacagg ccgatcatcg | 3986 |
| tcgcgctcca gcgaaagcgg tcctcgccga aaatgaccca gagcgctgcc ggcacctgtc | 4046 |
| ctacgagttg catgataaag aagacagtca taagtgcggc gacgatagtc atgccccgcg | 4106 |
| cccaccggaa ggagctgact gggttgaagg ctctcaaggg catcggtcga cgctctccct | 4166 |

```
tatgcgactc ctgcattagg aagcagccca gtagaattct ggtggtattg tgactgggga   4226
tgtagttgag aataagtcat acacaagtca gctttcttca agcctcatat aagtataagt   4286
agttcaatcg tattagctac ttgtacccag catctccgta tcgagaaaca caacaacatg   4346
ccccattgga cagatcatgc ggatacacag gttgtgcagt atcatacata ctcgatcaga   4406
caggtcgtct gaccatcata caagctgaac aagcgctcca tacttgcacg ctctctatat   4466
acacagttaa atgacatatc catagtctaa cctctaacag ttaatcttct ggtaagcctc   4526
ccagccagcc ttctggtatc gcttggcctc ctcaatagga tctcggttct ggccgtacag   4586
acctcggccg acaattatga tatccgttcc ggtagacatg acatcctcaa cagttcggta   4646
ctgctgtccg agagcgtctc ccttgtcgtc aagacccacc ccggggtca gaataagcca   4706 gtcctcagag tcgcccttag gtcggttctg ggcaatgaag ccaaccacaa actcggggtc   4766
ggatcgggca agctcaatgg tctgcttgga gtactcgcca gtggccagag agcccttgca   4826
agacagctcg gccagcatga gcagacctct ggccagcttc tcgttgggag aggggaccag   4886
gaactccttg tactgggagt tctcgtagtc agagacgtcc tccttcttct gttcagagac   4946
agtttcctcg gcaccagctc gcaggccagc aatgattccg gttccgggta caccgtgggc   5006
gttggtgata tcgaccact cggcgattcg gtagacaccg ttcttgtact ggtgcttgac   5066
agtgttgcca atatctgcga actttctgtc ctcgaacagg aagaaaccgt gcttaagagc   5126
aagttccttg aggggagca cagtgccggc gtaggtgaag tcgtcaatga tgtcgatatg   5186
ggtcttgatc atgcacacat aaggtccgac cttatcggca agctcaatga gctccttggt   5246
ggtggtaaca tccagagaag cacacaggtt ggttttcttg gctgccacga gcttgagcac   5306
tcgagcggca aaggcggact tgtggacgtt agctcgagct tcgtaggagg gcattttggt   5366
ggtgaagagg agactgaaat aaatttagtc tgcagaactt tttatcggaa ccttatctgg   5426
ggcagtgaag tatatgttat ggtaatagtt acgagttagt tgaacttata gatagactgg   5486
actatacggc tatcggtcca aattagaaag aacgtcaatg gctctctggg cgtcgccttt   5546
gccgacaaaa atgtgatcat gatgaaagcc agcaatgacg ttgcagctga tattgttgtc   5606
ggccaaccgc gccgaaaacg cagctgtcag acccacagcc tccaacgaag aatgtatcgt   5666
caaagtgatc caagcacact catagttgga gtcgtactcc aaaggcggca atgacgagtc   5726
agacaggagg cagacaaggt atagggcggc gcctacaatc catgccaacc cgttccatgt   5786
gctcgccgag gcggcataaa tcgccgtgac gatcagcggt ccagtgatcg aagttaggct   5846
ggtaagagcc gcgagcgatc cttgaagctg tccctgatgg tcgtcatcta cctgcctgga   5906
cagcatggcc tgcaacgcgg gcatcccgat gccgccggaa gcgagaagaa tcataatggg   5966
gaaggccatc cagcctcgcg tcgcgaacgc cagcaagacg tagcccagcg cgtcggccgc   6026
catgccggcg ataatggcct gcttctcgcc gaaacgtttg gtggcgggac cagtgacgaa   6086
ggcttgagcg agggcgtgca agattccgaa taccgcaagc gacaggccga tcatcgtcgc   6146
gctccagcga aagcggtcct cgccgaaaat gacccagagc gctgccggca cctgtcctac   6206
gagttgcatg ataaagaaga cagtcataag tgcggcgacg atagtcatgc cccgcgccca   6266
ccggaaggag ctgactgggt tgaaggctct caagggcatc ggtcgacgct ctcccttatg   6326
cgactcctgc attaggaagc agcccagtag atccccggga attcactggc cgtcgtttta   6386
caacgtcgtg actgggaaaa ccctggcgtt acccaactta atcgccttgc agcacatccc   6446
cctttcgcca gctggcgtaa tagcgaagag gcccgcaccg atcgcccttc ccaacagttg   6506
```

```
cgcagcctga atggcgaatg gcgcctgatg cggtattttc tccttacgca tctgtgcggt    6566
atttcacacc gcatatggtg cactctcagt acaatctgct ctgatgccgc atagttaagc    6626
cagccccgac acccgccaac acccgctgac gcgccctgac gggcttgtct gctcccggca    6686
tccgcttaca gacaagctgt gaccgtctcc gggagctgca tgtgtcagag gttttcaccg    6746
tcatcaccga aacgcgcgag acgaaagggc ctcgtgatac gcctattttt ataggttaat    6806
gtcatgataa taatggtttc ttagacgtca ggtggcactt ttcggggaaa tgtgcgcgga    6866
acccctattt gtttattttt ctaaatacat tcaaatatgt atccgctcat gagacaataa    6926
ccctgataaa tgcttcaata atattgaaaa aggaagagta tgagtattca acatttccgt    6986
gtcgccctta ttccctttt tgcggcattt tgccttcctg ttttgctca cccagaaacg    7046 ctggtgaaag taaaagatgc tgaagatcag ttgggtgcac gagtgggtta catcgaactg    7106
gatctcaaca gcggtaagat ccttgagagt tttcgccccg aagaacgttt tccaatgatg    7166
agcactttta agttctgct atgtggcgcg gtattatccc gtattgacgc cgggcaagag    7226
caactcggtc gccgcataca ctattctcag aatgacttgg ttgagtactc accagtcaca    7286
gaaaagcatc ttacggatgg catgacagta agagaattat gcagtgctgc cataaccatg    7346
agtgataaca ctgcggccaa cttacttctg acaacgatcg aggaccgaa ggagctaacc    7406 gcttttttgc acaacatggg ggatcatgta actcgccttg atcgttggga accggagctg    7466
aatgaagcca taccaaacga cgagcgtgac accacgatgc ctgtagcaat ggcaacaacg    7526
ttgcgcaaac tattaactgg cgaactactt actctagctt cccggcaaca attaatagac    7586
tggatggagg cggataaagt tgcaggacca cttctgcgct cggcccttcc ggctggctgg    7646
tttattgctg ataaatctgg agccggtgag cgtgggtctc gcggtatcat tgcagcactg    7706
gggccagatg gtaagccctc ccgtatcgta gttatctaca cgacggggag tcaggcaact    7766
atggatgaac gaaatagaca gatcgctgag ataggtgcct cactgattaa gcattggtaa    7826
ctgtcagacc aagtttactc atatatactt tagattgatt taaaacttca tttttaattt    7886
aaaaggatct aggtgaagat cctttttgat aatctcatga ccaaaatccc ttaacgtgag    7946
ttttcgttcc actgagcgtc agaccccgta gaaaagatca aaggatcttc ttgagatcct    8006
ttttttctgc gcgtaatctg ctgcttgcaa acaaaaaac caccgctacc agcggtggtt    8066
tgtttgccgg atcaagagct accaactctt tttccgaagg taactggctt cagcagagcg    8126
cagataccaa atactgtcct tctagtgtag ccgtagttag gccaccactt caagaactct    8186
gtagcaccgc ctacatacct cgctctgcta atcctgttac cagtggctgc tgccagtggc    8246
gataagtcgt gtcttaccgg gttggactca agacgatagt taccggataa ggcgcagcgg    8306
tcgggctgaa cggggggttc gtgcacacag cccagcttgg agcgaacgac ctacaccgaa    8366
ctgagatacc tacagcgtga gctatgagaa agcgccacgc ttcccgaagg gagaaaggcg    8426
gacaggtatc cggtaagcgg cagggtcgga acaggagagc gcacgaggga gcttccaggg    8486
ggaaacgcct ggtatcttta tagtcctgtc gggtttcgcc acctctgact tgagcgtcga    8546
tttttgtgat gctcgtcagg ggggcggagc ctatggaaaa acgccagcaa cgcggccttt    8606
ttacggttcc tggccttttg ctggcctttt gctcacatgt tctttcctgc gttatcccct    8666
gattctgtgg ataaccgtat taccgccttt gagtgagctg ataccgctcg ccgcagccga    8726
acgaccgagc gcagcgagtc agtgagcgag gaagcggaag agcgcccaat acgcaaaccg    8786
cctctccccg cgcgttggcc gattcattaa tgcagctggc acgacaggtt cccgactgg    8846 aaagcgggca gtgagcgcaa cgcaattaat gtgagttagc tcactcatta ggcaccccag    8906
```

```
gctttacact ttatgcttcc ggctcgtatg ttgtgtggaa ttgtgagcgg ataacaattt    8966
cacacaggaa acagctatga ccatgattac gccaagcttc catgggatct ctagagtcga    9026
cgggcccggt accccacag ttctcactca gatcatggag actctaacct tgagacatca     9086
attatcagct ctcgaggata atgttagtgc agttccagga ctcattgtgc aactgtcacc    9146
acggcatttt gggtctgttc ttttgaagta cagaaatatc ctcattgttg gtatactttg    9206
ggactttttc ttgttacaga agaataaaaa aacctcgact gatgtactaa ttacatggtt    9266
aacatcccca aggtcaaagt acagatattg taccgacttc tgaaatttgt gggatccaca    9326 cacgacctc tgcgatgata caatatcatg gttccatggt ctcttgaatc acaccactca     9386
ataataaaca ccagctcttt caatccaact tagctttctt ccacttgaac ataggccatc    9446
cccccttctt tctattttac ataaaatagca agatccttac ccctacatgt ctcataacac    9506
aatctcaact tgacttccca taagaagttc actaccctaa ggactctggc agtatttact    9566
gctctcgtgg cggccgcacc tgctcctgca cctaagttcg tcaaaatcgg ttttactcag    9626
agaatcaaca accctaccaa ctgtacatac tgctaaccct gattctttga ataaccccaa    9686
taaggctcct gctgaccctt ctgccgttct aggaaaccag cttgttgagt acgctgtgaa    9746
catcactctt ggtatacccg gtcagccctt ctcagttcag attgacacag gctcgtctga    9806
cttgtgggtg aagagtgacg gctcctccgg tgcattcaac aagaaggctt cttctacttt    9866
tcaggaggac gttcccaacg gctttgcaat gcccacgga gacaaaacct ctgccattgg     9926
agattgggtc aaagatacca tcaatatcgg tggtgttagt attgaccagt atagtattga    9986
ccagtatgag ttcgccatgg ctactcagac aaatactgac ccggtttttg gtatcggcta    10046
cccgagcaac gaggcgtctt atgggtaccc attccccaca gtaaccatct atattgcaaa    10106
acaatacgac tgcaattggg gattgttgct cgtatcgcac ccgtaccgtg ccaccgtaac    10166
accccccaga caccaatcac tacgaccgat ccaactccac gtttctgcta cccagtctgc    10226
tggccggctt ggctttgcgt ttcgctccca cactacaccg taataccacg tcactctcat    10286
tgcaggttac cctgcccgta gtcgctcgat ccacctcctc cttctctcgt gtgtgcagca    10346
aagaggcaga gatggagccc gtatggtgag ccgtagagtg gagcgagggg cgatcttaca    10406
acggctgtcg gcggatataa acggtatttt cacaattgca ccccagccag accgatagcc    10466
ggtcgcaatc cgccacccac aaccgtctac ctcccacaga accccgtcac ttccacccct    10526
ttccaccaga tcatatgtcc caacttgcca aattaaaacc gtgcgaattt tcaaaataaa    10586
ctttggcaaa gaggctgcaa aggaggggct ggtgagggcg tctggaagtc gaccagagac    10646
cgggttggcg gcgcatttgt gtcccaaaaa acagccccaa ttgccccaat gaccccaaa     10706 ttgacccagt agcgggccca accccggcga gagccccctt ctcccacat atcaaacctc    10766 ccccggttcc cacacttgcc gttaagggcg tagggtactg cagtctggaa tctacgcttg    10826
ttcagacttt gta                                                      10839
```

<210> SEQ ID NO 6
<211> LENGTH: 999
<212> TYPE: PRT
<213> ORGANISM: Artificial Sequence
<220> FEATURE:
<223> OTHER INFORMATION: Synthetic Construct

<400> SEQUENCE: 6

Met Leu Gln Ala Ala Ile Gly Lys Ile Val Gly Phe Ala Val Asn Arg
1               5                   10                  15

```
Pro Ile His Thr Val Leu Thr Ser Ile Val Ala Ser Thr Ala Tyr
        20                  25                  30

Leu Ala Ile Leu Asp Ile Ala Ile Pro Gly Phe Glu Gly Thr Gln Pro
            35                  40                  45

Ile Ser Tyr Tyr His Pro Ala Ala Lys Ser Tyr Asp Asn Pro Ala Asp
50                  55                  60

Trp Thr His Ile Ala Glu Ala Asp Ile Pro Ser Asp Ala Tyr Arg Leu
65                      70                  75                  80

Ala Phe Ala Gln Ile Arg Val Ser Asp Val Gln Gly Gly Glu Ala Pro
                    85                  90                  95

Thr Ile Pro Gly Ala Val Ala Val Ser Asp Leu Asp His Arg Ile Val
                100                 105                 110

Met Asp Tyr Lys Gln Trp Ala Pro Trp Thr Ala Ser Asn Glu Gln Ile
            115                 120                 125

Ala Ser Glu Asn His Ile Trp Lys His Ser Phe Lys Asp His Val Ala
130                 135                 140

Phe Ser Trp Ile Lys Trp Phe Arg Trp Ala Tyr Leu Arg Leu Ser Thr
145                 150                 155                 160

Leu Ile Gln Gly Ala Asp Asn Phe Asp Ile Ala Val Val Ala Leu Gly
                    165                 170                 175

Tyr Leu Ala Met His Tyr Thr Phe Phe Ser Leu Phe Arg Ser Met Arg
                180                 185                 190

Lys Val Gly Ser His Phe Trp Leu Ala Ser Met Ala Leu Val Ser Ser
                195                 200                 205

Thr Phe Ala Phe Leu Leu Ala Val Val Ala Ser Ser Leu Gly Tyr
            210                 215                 220

Arg Pro Ser Met Ile Thr Met Ser Glu Gly Leu Pro Phe Leu Val Val
225                 230                 235                 240

Ala Ile Gly Phe Asp Arg Lys Val Asn Leu Ala Ser Glu Val Leu Thr
                245                 250                 255

Ser Lys Ser Ser Gln Leu Ala Pro Met Val Gln Val Ile Thr Lys Ile
                260                 265                 270

Ala Ser Lys Ala Leu Phe Glu Tyr Ser Leu Glu Val Ala Ala Leu Phe
            275                 280                 285

Ala Gly Ala Tyr Thr Gly Val Pro Arg Leu Ser Gln Phe Cys Phe Leu
            290                 295                 300

Ser Ala Trp Ile Leu Ile Phe Asp Tyr Met Phe Leu Leu Thr Phe Tyr
305                 310                 315                 320

Ser Ala Val Leu Ala Ile Lys Phe Glu Ile Asn His Ile Lys Arg Asn
                325                 330                 335

Arg Met Ile Gln Asp Ala Leu Lys Glu Asp Gly Val Ser Ala Ala Val
            340                 345                 350

Ala Glu Lys Val Ala Asp Ser Ser Pro Asp Ala Lys Leu Asp Arg Lys
            355                 360                 365

Ser Asp Val Ser Leu Phe Gly Ala Ser Gly Ala Ile Ala Val Phe Lys
            370                 375                 380

Ile Phe Met Val Leu Gly Phe Leu Gly Leu Asn Leu Ile Asn Leu Thr
385                 390                 395                 400

Ala Ile Pro His Leu Gly Lys Ala Ala Ala Ala Gln Ser Val Thr
                405                 410                 415

Pro Ile Thr Leu Ser Pro Glu Leu Leu His Ala Ile Pro Ala Ser Val
            420                 425                 430
```

```
Pro Val Val Val Thr Phe Val Pro Ser Val Val Tyr Glu His Ser Gln
            435                 440                 445

Leu Ile Leu Gln Leu Glu Asp Ala Leu Thr Thr Phe Leu Ala Ala Cys
    450                 455                 460

Ser Lys Thr Ile Gly Asp Pro Val Ile Ser Lys Tyr Ile Phe Leu Cys
465                 470                 475                 480

Leu Met Val Ser Thr Ala Leu Asn Val Tyr Leu Phe Gly Ala Thr Arg
                485                 490                 495

Glu Val Val Arg Thr Gln Ser Val Lys Val Val Glu Lys His Val Pro
            500                 505                 510

Ile Val Ile Glu Lys Pro Ser Glu Lys Glu Asp Thr Ser Ser Glu
            515                 520                 525

Asp Ser Ile Glu Leu Thr Val Gly Lys Gln Pro Lys Pro Val Thr Glu
530                 535                 540

Thr Arg Ser Leu Asp Asp Leu Glu Ala Ile Met Lys Ala Gly Lys Thr
545                 550                 555                 560

Lys Leu Leu Glu Asp His Glu Val Val Lys Leu Ser Leu Glu Gly Lys
                565                 570                 575

Leu Pro Leu Tyr Ala Leu Glu Lys Gln Leu Gly Asp Asn Thr Arg Ala
            580                 585                 590

Val Gly Ile Arg Arg Ser Ile Ile Ser Gln Gln Ser Asn Thr Lys Thr
            595                 600                 605

Leu Glu Thr Ser Lys Leu Pro Tyr Leu His Tyr Asp Tyr Asp Arg Val
            610                 615                 620

Phe Gly Ala Cys Cys Glu Asn Val Ile Gly Tyr Met Pro Leu Pro Val
625                 630                 635                 640

Gly Val Ala Gly Pro Met Asn Ile Asp Gly Lys Asn Tyr His Ile Pro
                645                 650                 655

Met Ala Thr Thr Glu Gly Cys Leu Val Ala Ser Thr Met Arg Gly Cys
            660                 665                 670

Lys Ala Ile Asn Ala Gly Gly Gly Val Thr Thr Val Leu Thr Gln Asp
            675                 680                 685

Gly Met Thr Arg Gly Pro Cys Val Ser Phe Pro Ser Leu Lys Arg Ala
    690                 695                 700

Gly Ala Ala Lys Ile Trp Leu Asp Ser Glu Glu Gly Leu Lys Ser Met
705                 710                 715                 720

Arg Lys Ala Phe Asn Ser Thr Ser Arg Phe Ala Arg Leu Gln Ser Leu
                725                 730                 735

His Ser Thr Leu Ala Gly Asn Leu Leu Phe Ile Arg Phe Arg Thr Thr
            740                 745                 750

Thr Gly Asp Ala Met Gly Met Asn Met Ile Ser Lys Gly Val Glu His
            755                 760                 765

Ser Leu Ala Val Met Val Lys Glu Tyr Gly Phe Pro Asp Met Asp Ile
770                 775                 780

Val Ser Val Ser Gly Asn Tyr Cys Thr Asp Lys Lys Pro Ala Ala Ile
785                 790                 795                 800

Asn Trp Ile Glu Gly Arg Gly Lys Ser Val Val Ala Glu Ala Thr Ile
                805                 810                 815

Pro Ala His Ile Val Lys Ser Val Leu Lys Ser Glu Val Asp Ala Leu
            820                 825                 830

Val Glu Leu Asn Ile Ser Lys Asn Leu Ile Gly Ser Ala Met Ala Gly
            835                 840                 845

Ser Val Gly Gly Phe Asn Ala His Ala Ala Asn Leu Val Thr Ala Ile
```

```
            850                 855                 860
Tyr Leu Ala Thr Gly Gln Asp Pro Ala Gln Asn Val Glu Ser Ser Asn
865                 870                 875                 880

Cys Ile Thr Leu Met Ser Asn Val Asp Gly Asn Leu Leu Ile Ser Val
                885                 890                 895

Ser Met Pro Ser Ile Glu Val Gly Thr Ile Gly Gly Thr Ile Leu
            900                 905                 910

Glu Pro Gln Gly Ala Met Leu Glu Met Leu Gly Val Arg Gly Pro His
        915                 920                 925

Ile Glu Thr Pro Gly Ala Asn Ala Gln Gln Leu Ala Arg Ile Ile Ala
    930                 935                 940

Ser Gly Val Leu Ala Ala Glu Leu Ser Leu Cys Ser Ala Leu Ala Ala
945                 950                 955                 960

Gly His Leu Val Gln Ser His Met Thr His Asn Arg Ser Gln Ala Pro
                965                 970                 975

Thr Pro Ala Lys Gln Ser Gln Ala Asp Leu Gln Arg Leu Gln Asn Gly
            980                 985                 990

Ser Asn Ile Cys Ile Arg Ser
        995

<210> SEQ ID NO 7
<211> LENGTH: 20
<212> TYPE: DNA
<213> ORGANISM: Yarrowia lipolytica

<400> SEQUENCE: 7
tccagaagcg ctacaaagag                                              20

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
attaccctgt tatccctatg aaggttgcag tcgtagtc                          38

<210> SEQ ID NO 9
<211> LENGTH: 38
<212> TYPE: DNA
<213> ORGANISM: Artificial Sequence
<220> FEATURE:
<223> OTHER INFORMATION: primer

<400> SEQUENCE: 9
tagggataac agggtaattg cgatctcgat gagtgatg                          38

<210> SEQ ID NO 10
<211> LENGTH: 20
<212> TYPE: DNA
<213> ORGANISM: Yarrowia lipolytica

<400> SEQUENCE: 10
gcccagaaga ttggaatgac                                              20

<210> SEQ ID NO 11
<211> LENGTH: 31
<212> TYPE: DNA
<213> ORGANISM: Artificial Sequence
<220> FEATURE:
```

<223> OTHER INFORMATION: primer

<400> SEQUENCE: 11
atataccgcg ggattccgcc aagtgagact g                                    31

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
attaccctgt tatccctacg tcgaggaagt aggtcatc                             38

<210> SEQ ID NO 13
<211> LENGTH: 38
<212> TYPE: DNA
<213> ORGANISM: Artificial Sequence
<220> FEATURE:
<223> OTHER INFORMATION: primer

<400> SEQUENCE: 13
tagggataac agggtaatgc gagcttgatg aggaatag                             38

<210> SEQ ID NO 14
<211> LENGTH: 31
<212> TYPE: DNA
<213> ORGANISM: Artificial Sequence
<220> FEATURE:
<223> OTHER INFORMATION: primer

<400> SEQUENCE: 14
atataccgcg gcctgacgcc aatttgaaga g                                    31

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
atataccgcg gctgggctgt tcggtcgata g                                    31

<210> SEQ ID NO 16
<211> LENGTH: 38
<212> TYPE: DNA
<213> ORGANISM: Artificial Sequence
<220> FEATURE:
<223> OTHER INFORMATION: primer

<400> SEQUENCE: 16
tagggataac agggtaatag gacgcacaac gccatcac                             38

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
attaccctgt tatccctacg ctcccattgg aaacta                               36

```
<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18 ataccgcg gtctcttcgc tgtggtctag g                              31

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19 ataccgcg gtccaccgtt ctccttcata c                              31

<210> SEQ ID NO 20
<211> LENGTH: 38
<212> TYPE: DNA
<213> ORGANISM: Artificial Sequence
<220> FEATURE:
<223> OTHER INFORMATION: primer

<400> SEQUENCE: 20
tagggataac agggtaatat gtctctaggg tcgaagtc                     38

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
attaccctgt tatccctatg gcaagcctca ctactacg                     38

<210> SEQ ID NO 22
<211> LENGTH: 31
<212> TYPE: DNA
<213> ORGANISM: Artificial Sequence
<220> FEATURE:
<223> OTHER INFORMATION: primer

<400> SEQUENCE: 22 ataccgcg gtgcggcgga actactgtat c                              31

<210> SEQ ID NO 23
<211> LENGTH: 31
<212> TYPE: DNA
<213> ORGANISM: Artificial Sequence
<220> FEATURE:
<223> OTHER INFORMATION: primer

<400> SEQUENCE: 23 ataccgcg ggggattctc cgggttattt g                              31

<210> SEQ ID NO 24
<211> LENGTH: 38
<212> TYPE: DNA
<213> ORGANISM: Artificial Sequence
<220> FEATURE:
<223> OTHER INFORMATION: primer
```

```
<400> SEQUENCE: 24
tagggataac agggtaatac gtctcggacc ttgaattg                    38

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
attaccctgt tatccctacc ttcaacctgt ccgacttc                    38

<210> SEQ ID NO 26
<211> LENGTH: 31
<212> TYPE: DNA
<213> ORGANISM: Artificial Sequence
<220> FEATURE:
<223> OTHER INFORMATION: primer

<400> SEQUENCE: 26
atataccgcg ggaagcggtc ctcgttgtat g                           31

<210> SEQ ID NO 27
<211> LENGTH: 20
<212> TYPE: DNA
<213> ORGANISM: Yarrowia lipolytica

<400> SEQUENCE: 27
gtgtagcaac tcggatacag                                        20

<210> SEQ ID NO 28
<211> LENGTH: 38
<212> TYPE: DNA
<213> ORGANISM: Artificial Sequence
<220> FEATURE:
<223> OTHER INFORMATION: primer

<400> SEQUENCE: 28
tagggataac agggtaatgg tccataagca gagtgttc                    38

<210> SEQ ID NO 29
<211> LENGTH: 38
<212> TYPE: DNA
<213> ORGANISM: Artificial Sequence
<220> FEATURE:
<223> OTHER INFORMATION: primer

<400> SEQUENCE: 29
attaccctgt tatccctaac cctcgacctc cttattac                    38

<210> SEQ ID NO 30
<211> LENGTH: 20
<212> TYPE: DNA
<213> ORGANISM: Yarrowia lipolytica

<400> SEQUENCE: 30
ctcttcttga ctggcatagc                                        20

<210> SEQ ID NO 31
<211> LENGTH: 31
<212> TYPE: DNA
<213> ORGANISM: Artificial Sequence
<220> FEATURE:
<223> OTHER INFORMATION: primer
```

```
<400> SEQUENCE: 31
atataaagct tgcggctcgg cacgtgatct g                              31

<210> SEQ ID NO 32
<211> LENGTH: 32
<212> TYPE: DNA
<213> ORGANISM: Artificial Sequence
<220> FEATURE:
<223> OTHER INFORMATION: primer

<400> SEQUENCE: 32
atataggatc catcgtgcgt acgtcgctag tg                             32

<210> SEQ ID NO 33
<211> LENGTH: 31
<212> TYPE: DNA
<213> ORGANISM: Artificial Sequence
<220> FEATURE:
<223> OTHER INFORMATION: primer

<400> SEQUENCE: 33
atataggatc ccgaccggca cgatcaattg g                              31

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
atatacatat gggtgcatct cagcccgacc tc                             32

<210> SEQ ID NO 35
<211> LENGTH: 20
<212> TYPE: DNA
<213> ORGANISM: Yarrowia lipolytica

<400> SEQUENCE: 35
tcccgaaaca cagaacttcc                                           20

<210> SEQ ID NO 36
<211> LENGTH: 32
<212> TYPE: DNA
<213> ORGANISM: Artificial Sequence
<220> FEATURE:
<223> OTHER INFORMATION: primer

<400> SEQUENCE: 36
atataaagct tggtggacgt tccggcagac ag                             32

<210> SEQ ID NO 37
<211> LENGTH: 32
<212> TYPE: DNA
<213> ORGANISM: Artificial Sequence
<220> FEATURE:
<223> OTHER INFORMATION: primer

<400> SEQUENCE: 37
atataggatc cctcccaggc atctccacac tc                             32

<210> SEQ ID NO 38
<211> LENGTH: 31
<212> TYPE: DNA
```

```
<213> ORGANISM: Artificial Sequence
<220> FEATURE:
<223> OTHER INFORMATION: primer

<400> SEQUENCE: 38
atataggatc ccacttacag gcttagcaag g                                        31

<210> SEQ ID NO 39
<211> LENGTH: 32
<212> TYPE: DNA
<213> ORGANISM: Artificial Sequence
<220> FEATURE:
<223> OTHER INFORMATION: primer

<400> SEQUENCE: 39
atatagcggc cgcggaaatc acgcttgatt cg                                       32

<210> SEQ ID NO 40
<211> LENGTH: 20
<212> TYPE: DNA
<213> ORGANISM: Yarrowia lipolytica

<400> SEQUENCE: 40
taggcgctgg tacagaagag                                                     20

<210> SEQ ID NO 41
<211> LENGTH: 31
<212> TYPE: DNA
<213> ORGANISM: Artificial Sequence
<220> FEATURE:
<223> OTHER INFORMATION: primer

<400> SEQUENCE: 41
atataaagct tgagtacagt aggtggtact c                                        31

<210> SEQ ID NO 42
<211> LENGTH: 31
<212> TYPE: DNA
<213> ORGANISM: Artificial Sequence
<220> FEATURE:
<223> OTHER INFORMATION: primer

<400> SEQUENCE: 42
atataggatc cagtggtggt ggtggtggta g                                        31

<210> SEQ ID NO 43
<211> LENGTH: 31
<212> TYPE: DNA
<213> ORGANISM: Artificial Sequence
<220> FEATURE:
<223> OTHER INFORMATION: primer

<400> SEQUENCE: 43
atataggatc ctttacgtgc aacaggagga g                                        31

<210> SEQ ID NO 44
<211> LENGTH: 31
<212> TYPE: DNA
<213> ORGANISM: Artificial Sequence
<220> FEATURE:
<223> OTHER INFORMATION: primer

<400> SEQUENCE: 44
atatacatat ggcctgtctt gagttctttg g                                        31
```

<210> SEQ ID NO 45
<211> LENGTH: 20
<212> TYPE: DNA
<213> ORGANISM: Yarrowia lipolytica

<400> SEQUENCE: 45
agggtcgtag ataacgagtc                                               20

<210> SEQ ID NO 46
<211> LENGTH: 32
<212> TYPE: DNA
<213> ORGANISM: Artificial Sequence
<220> FEATURE:
<223> OTHER INFORMATION: primer

<400> SEQUENCE: 46
atataaagct tcacgtggct gctgggccaa cc                                 32

<210> SEQ ID NO 47
<211> LENGTH: 31
<212> TYPE: DNA
<213> ORGANISM: Artificial Sequence
<220> FEATURE:
<223> OTHER INFORMATION: primer

<400> SEQUENCE: 47
atataggatc ccgcacggta tcggagcatc g                                  31

<210> SEQ ID NO 48
<211> LENGTH: 31
<212> TYPE: DNA
<213> ORGANISM: Artificial Sequence
<220> FEATURE:
<223> OTHER INFORMATION: primer

<400> SEQUENCE: 48
atataggatc ccgcggctat tgacgctgag g                                  31

<210> SEQ ID NO 49
<211> LENGTH: 34
<212> TYPE: DNA
<213> ORGANISM: Artificial Sequence
<220> FEATURE:
<223> OTHER INFORMATION: primer

<400> SEQUENCE: 49
atatacatat gcccgtcagc tccatcgacg agtg                               34

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
aggtgtactg tagccaccct gac                                           23

<210> SEQ ID NO 51
<211> LENGTH: 31
<212> TYPE: DNA
<213> ORGANISM: Artificial Sequence
<220> FEATURE:
<223> OTHER INFORMATION: primer

<400> SEQUENCE: 51
atataaagct tccggccagc cgctggcaac g                                                31

<210> SEQ ID NO 52
<211> LENGTH: 31
<212> TYPE: DNA
<213> ORGANISM: Artificial Sequence
<220> FEATURE:
<223> OTHER INFORMATION: primer

<400> SEQUENCE: 52
atataggatc cacacgacag ctgcacctga c                                                31

<210> SEQ ID NO 53
<211> LENGTH: 31
<212> TYPE: DNA
<213> ORGANISM: Artificial Sequence
<220> FEATURE:
<223> OTHER INFORMATION: primer

<400> SEQUENCE: 53
atataggatc ccagccatga gccaggcatt g                                                31

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54
atatacatat gggcgccagc cacatttgcc ctc                                              33

<210> SEQ ID NO 55
<211> LENGTH: 20
<212> TYPE: DNA
<213> ORGANISM: Yarrowia lipolytica

<400> SEQUENCE: 55
agcgatacag cagttgactc                                                             20

<210> SEQ ID NO 56
<211> LENGTH: 20
<212> TYPE: DNA
<213> ORGANISM: Yarrowia lipolytica

<400> SEQUENCE: 56
tcagccgtct acttgtagag                                                             20

<210> SEQ ID NO 57
<211> LENGTH: 31
<212> TYPE: DNA
<213> ORGANISM: Artificial Sequence
<220> FEATURE:
<223> OTHER INFORMATION: primer

<400> SEQUENCE: 57
atataggatc cgtggctcgg atactcctga c                                                31

<210> SEQ ID NO 58
<211> LENGTH: 31
<212> TYPE: DNA
<213> ORGANISM: Artificial Sequence
<220> FEATURE:
<223> OTHER INFORMATION: primer

<400> SEQUENCE: 58

```
atataggatc cagccggagg tcagatcaag c                              31

<210> SEQ ID NO 59
<211> LENGTH: 32
<212> TYPE: DNA
<213> ORGANISM: Artificial Sequence
<220> FEATURE:
<223> OTHER INFORMATION: primer

<400> SEQUENCE: 59
atatacatat ggcgcaatag ttcgccggcc tg                             32

<210> SEQ ID NO 60
<211> LENGTH: 20
<212> TYPE: DNA
<213> ORGANISM: Yarrowia lipolytica

<400> SEQUENCE: 60
ctcgtgttgt gcctttcttg                                           20

<210> SEQ ID NO 61
<211> LENGTH: 34
<212> TYPE: DNA
<213> ORGANISM: Artificial Sequence
<220> FEATURE:
<223> OTHER INFORMATION: primer

<400> SEQUENCE: 61
atataaagct tgcgcgacaa cccatagcga tggc                           34

<210> SEQ ID NO 62
<211> LENGTH: 31
<212> TYPE: DNA
<213> ORGANISM: Artificial Sequence
<220> FEATURE:
<223> OTHER INFORMATION: primer

<400> SEQUENCE: 62
atataggatc cgataagagg gcgctctgac c                              31

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
atataggatc cggcgtgaca tcgagtttgg                                30

<210> SEQ ID NO 64
<211> LENGTH: 31
<212> TYPE: DNA
<213> ORGANISM: Artificial Sequence
<220> FEATURE:
<223> OTHER INFORMATION: primer

<400> SEQUENCE: 64
atatacatat gctacgtctc gccgcagagg g                              31

<210> SEQ ID NO 65
<211> LENGTH: 20
<212> TYPE: DNA
<213> ORGANISM: Yarrowia lipolytica
```

<400> SEQUENCE: 65
agcgagaggt tatacggaag                                              20

<210> SEQ ID NO 66
<211> LENGTH: 20
<212> TYPE: DNA
<213> ORGANISM: Yarrowia lipolytica

<400> SEQUENCE: 66
ctcctacagc ctctcaagac                                              20

<210> SEQ ID NO 67
<211> LENGTH: 20
<212> TYPE: DNA
<213> ORGANISM: Yarrowia lipolytica

<400> SEQUENCE: 67
gtctacaaga cagcccagag                                              20

<210> SEQ ID NO 68
<211> LENGTH: 20
<212> TYPE: DNA
<213> ORGANISM: Yarrowia lipolytica

<400> SEQUENCE: 68
ccgcttgaga agagcaatac                                              20

<210> SEQ ID NO 69
<211> LENGTH: 31
<212> TYPE: DNA
<213> ORGANISM: Artificial Sequence
<220> FEATURE:
<223> OTHER INFORMATION: primer

<400> SEQUENCE: 69
atataaagct tcgccacctg tccacgtctc g                                 31

<210> SEQ ID NO 70
<211> LENGTH: 31
<212> TYPE: DNA
<213> ORGANISM: Artificial Sequence
<220> FEATURE:
<223> OTHER INFORMATION: primer

<400> SEQUENCE: 70
atataggatc cgcgaagcga cgtgtggtga g                                 31

<210> SEQ ID NO 71
<211> LENGTH: 31
<212> TYPE: DNA
<213> ORGANISM: Artificial Sequence
<220> FEATURE:
<223> OTHER INFORMATION: primer

<400> SEQUENCE: 71
atataggatc cgctgagcac gcgagtacac c                                 31

<210> SEQ ID NO 72
<211> LENGTH: 31
<212> TYPE: DNA
<213> ORGANISM: Artificial Sequence
<220> FEATURE:
<223> OTHER INFORMATION: primer

<400> SEQUENCE: 72

-continued atatagaatt cgatctgtcg tacaactaag g	31

<210> SEQ ID NO 73
<211> LENGTH: 20
<212> TYPE: DNA
<213> ORGANISM: Yarrowia lipolytica

<400> SEQUENCE: 73
cagaagttac gacgccaagg	20

<210> SEQ ID NO 74
<211> LENGTH: 31
<212> TYPE: DNA
<213> ORGANISM: Artificial Sequence
<220> FEATURE:
<223> OTHER INFORMATION: primer

<400> SEQUENCE: 74
atataaagct tccgtaataa atgcccgtct c	31

<210> SEQ ID NO 75
<211> LENGTH: 31
<212> TYPE: DNA
<213> ORGANISM: Artificial Sequence
<220> FEATURE:
<223> OTHER INFORMATION: primer

<400> SEQUENCE: 75
atataggatc caggtcgatt tcggcgctgt g	31

<210> SEQ ID NO 76
<211> LENGTH: 31
<212> TYPE: DNA
<213> ORGANISM: Artificial Sequence
<220> FEATURE:
<223> OTHER INFORMATION: primer

<400> SEQUENCE: 76
atataggatc cggttaggca aatagctaat g	31

<210> SEQ ID NO 77
<211> LENGTH: 31
<212> TYPE: DNA
<213> ORGANISM: Artificial Sequence
<220> FEATURE:
<223> OTHER INFORMATION: primer

<400> SEQUENCE: 77
atatagaatt cgcctggagc gagtttctga g	31

<210> SEQ ID NO 78
<211> LENGTH: 20
<212> TYPE: DNA
<213> ORGANISM: Yarrowia lipolytica

<400> SEQUENCE: 78
tcgcaagggc catagaggtg	20

<210> SEQ ID NO 79
<211> LENGTH: 31
<212> TYPE: DNA
<213> ORGANISM: Artificial Sequence
<220> FEATURE:
<223> OTHER INFORMATION: primer

<400> SEQUENCE: 79
atataaagct tccttgcaca tctccgatga c                                    31

<210> SEQ ID NO 80
<211> LENGTH: 31
<212> TYPE: DNA
<213> ORGANISM: Artificial Sequence
<220> FEATURE:
<223> OTHER INFORMATION: primer

<400> SEQUENCE: 80
atataggatc cggtgttacg ccaccacgtt g                                    31

<210> SEQ ID NO 81
<211> LENGTH: 31
<212> TYPE: DNA
<213> ORGANISM: Artificial Sequence
<220> FEATURE:
<223> OTHER INFORMATION: primer

<400> SEQUENCE: 81
atataggatc cgggacctgc gatacgaatg c                                    31

<210> SEQ ID NO 82
<211> LENGTH: 31
<212> TYPE: DNA
<213> ORGANISM: Artificial Sequence
<220> FEATURE:
<223> OTHER INFORMATION: primer

<400> SEQUENCE: 82
atatagaatt cgcttgcgca gccggtgtat c                                    31

<210> SEQ ID NO 83
<211> LENGTH: 20
<212> TYPE: DNA
<213> ORGANISM: Yarrowia lipolytica

<400> SEQUENCE: 83
ggcgttgtgg agctatcacc                                                 20

<210> SEQ ID NO 84
<211> LENGTH: 31
<212> TYPE: DNA
<213> ORGANISM: Artificial Sequence
<220> FEATURE:
<223> OTHER INFORMATION: primer

<400> SEQUENCE: 84
atataaagct tgcgtgcggt gcgtgcgtat g                                    31

<210> SEQ ID NO 85
<211> LENGTH: 31
<212> TYPE: DNA
<213> ORGANISM: Artificial Sequence
<220> FEATURE:
<223> OTHER INFORMATION: primer

<400> SEQUENCE: 85
atataggatc ccagcaccac gaaattatac g                                    31

<210> SEQ ID NO 86
<211> LENGTH: 31
<212> TYPE: DNA
<213> ORGANISM: Artificial Sequence
<220> FEATURE:
<223> OTHER INFORMATION: primer

<400> SEQUENCE: 86
atataggatc cgtgcgctta catgtggacc g                            31

<210> SEQ ID NO 87
<211> LENGTH: 31
<212> TYPE: DNA
<213> ORGANISM: Artificial Sequence
<220> FEATURE:
<223> OTHER INFORMATION: primer

<400> SEQUENCE: 87
atatagaatt ccaggcagct tcttgccaat g                            31

<210> SEQ ID NO 88
<211> LENGTH: 20
<212> TYPE: DNA
<213> ORGANISM: Yarrowia lipolytica

<400> SEQUENCE: 88
gagataggag gttcccatac                                         20

<210> SEQ ID NO 89
<211> LENGTH: 20
<212> TYPE: DNA
<213> ORGANISM: Yarrowia lipolytica

<400> SEQUENCE: 89
ctacgcttgt tcagactttg                                         20

<210> SEQ ID NO 90
<211> LENGTH: 46
<212> TYPE: DNA
<213> ORGANISM: Artificial Sequence
<220> FEATURE:
<223> OTHER INFORMATION: primer

<400> SEQUENCE: 90
gtgtgcttgt cgtcagacat tttgaatgat tcttatactc agaagg            46

<210> SEQ ID NO 91
<211> LENGTH: 46
<212> TYPE: DNA
<213> ORGANISM: Artificial Sequence
<220> FEATURE:
<223> OTHER INFORMATION: primer

<400> SEQUENCE: 91
ccttctgagt ataagaatca ttcaaaatgt ctgacgacaa gcacac            46

<210> SEQ ID NO 92
<211> LENGTH: 26
<212> TYPE: DNA
<213> ORGANISM: Artificial Sequence
<220> FEATURE:
<223> OTHER INFORMATION: primer

<400> SEQUENCE: 92
gcatgcttag attcgaggtc ggagat                                  26

<210> SEQ ID NO 93
<211> LENGTH: 26
<212> TYPE: DNA

```
<213> ORGANISM: Artificial Sequence
<220> FEATURE:
<223> OTHER INFORMATION: primer

<400> SEQUENCE: 93
ggtaccacgc acggatagtt tatcca                                              26

<210> SEQ ID NO 94
<211> LENGTH: 31
<212> TYPE: DNA
<213> ORGANISM: Artificial Sequence
<220> FEATURE:
<223> OTHER INFORMATION: primer

<400> SEQUENCE: 94
ggtacccaaa gtcaactaat gtcaagtaaa g                                        31

<210> SEQ ID NO 95
<211> LENGTH: 17
<212> TYPE: DNA
<213> ORGANISM: Yarrowia lipolytica

<400> SEQUENCE: 95
cctccaacgt gactttc                                                        17

<210> SEQ ID NO 96
<211> LENGTH: 17
<212> TYPE: DNA
<213> ORGANISM: Yarrowia lipolytica

<400> SEQUENCE: 96
agagacctcc cacaaag                                                        17

<210> SEQ ID NO 97
<211> LENGTH: 46
<212> TYPE: DNA
<213> ORGANISM: Artificial Sequence
<220> FEATURE:
<223> OTHER INFORMATION: primer

<400> SEQUENCE: 97
agagagtcga gtagagccat tttgaatgat tcttatactc agaagg                        46

<210> SEQ ID NO 98
<211> LENGTH: 46
<212> TYPE: DNA
<213> ORGANISM: Artificial Sequence
<220> FEATURE:
<223> OTHER INFORMATION: primer

<400> SEQUENCE: 98
ccttctgagt ataagaatca ttcaaaatgg ctctactcga ctctct                        46

<210> SEQ ID NO 99
<211> LENGTH: 35
<212> TYPE: DNA
<213> ORGANISM: Yarrowia lipolytica

<400> SEQUENCE: 99
atatagcatg cctaccacac atcttcctgg tagac                                    35

<210> SEQ ID NO 100
<211> LENGTH: 18
<212> TYPE: DNA
<213> ORGANISM: Yarrowia lipolytica
```

```
<400> SEQUENCE: 100
ctcaagatac ggcattgg                                                 18

<210> SEQ ID NO 101
<211> LENGTH: 18
<212> TYPE: DNA
<213> ORGANISM: Yarrowia lipolytica

<400> SEQUENCE: 101
tccttggcta gacgaatg                                                 18
```

YEAST STRAINS WITH REDUCED FATTY ALCOHOL OXIDASE ACTIVITY AND METHOD FOR THE PRODUCTION OF OMEGA-HYDROXY FATTY ACIDS AND DICARBOXYLIC ACIDS

CROSS REFERENCE TO RELATED APPLICATIONS

This application is a continuation of U.S. patent application Ser. No. 15/103,191, filed on Jun. 9, 2016, which is itself a U.S. national stage of International Application No. PCT/EP2014/077237 filed on Dec. 10, 2014, which itself claims the benefit of priority under 35 U.S.C. § 119 of German Application No. DE 102013022175.7, filed on Dec. 12, 2013; all applications are incorporated by reference herein in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: PRVI_018_02US_SeqList.txt, date recorded: Aug. 13, 2018, file size 75 kilobytes).

BACKGROUND OF THE INVENTION

The invention relates to various yeast strains of the type *Yarrowia lipolytica* as well as relevant methods for the biocatalytic preparation of ω-hydroxy fatty acids or dicarboxylic acids with the aid of these strains.

Dicarboxylic acids comprise carboxylic acids having two carboxy groups (general structure: HOOC—$(CH_2)_n$—COOH), which have diverse applications in the chemical industry, e.g. for the preparation of fragrances, adhesives, Nylon and other polyamides, resins, corrosion inhibitors or lubricants. In particular, the biotechnological production of long-chain dicarboxylic acids is of particular interest since a number of undesired side products are formed during the chemical synthesis of the same.

ω-hydroxy fatty acids contain at the $C_ω$ atom (C atom having the furthest possible distance from the carboxyl group) a hydroxyl group (general structure: HOOC—$(CH_2)_n$—$CH_2OH$). ω-hydroxy fatty acids are also of great importance in the chemical industry since they are used, inter alia, in lubricants, adhesives, cosmetics and cancer therapeutic agents. Furthermore, ω-hydroxy fatty acids could acquire great importance in future since they can be used as monomers for the synthesis of bioplastics.

In order to obtain ω-hydroxy fatty acids and dicarboxylic acids from n-alkanes and fatty acids, the non-conventional yeast *Yarrowia (Y.) lipolytica* is to be used within the framework of the invention. The yeast *Y. lipolytica* was selected as host organism for the bioconversion since it is able to use a plurality of substrates as carbon source. In addition to glucose, glycerol, proteins, alcohols and acetate, this also includes a plurality of hydrophobic substrates such as vegetable oils, fats, fatty acids and n-alkanes (Barth G & Gaillardin C (1997) *FEMS Microbiol Rev* 19: 219-237). The hydrophobic substrates are emulsified by the yeasts and assimilated into the cell interior with the aid of specialized membrane transporters (Fickers P, Benetti P H, Waché Y, Marty A, Mauersberger S, Smit M S & Nicaud J M (2005) *FEMS Yeast Res* 5: 527-543). n-alkanes assimilated into the cell are converted stepwise to fatty acid having the same chain length (FIG. 1) in the course of the primary (monoterminal) alkane oxidation. The fatty acids are then broken down in the course of the β-oxidation to acetyl CoA which flows into the tri-carboxylic acid and the glyoxylate cycle. In parallel with the β-oxidation of fatty acids in the peroxisomes, ω-oxidation takes place in the endoplasmic reticulum (cf. FIG. 1). However, this diterminal oxidation of fatty acids naturally takes place to a far lesser extent than the β-oxidation.

Various yeasts such as, for example, *Candida (C.) tropicalis* and *Y. lipolytica* are capable of converting long-chain alkanes or fatty acids to α,ω-dicarboxylic acids. In order that the hydrophobic substrates can be converted at all to the respective dicarboxylic acid, their metabolization in the course of the β-oxidation must be prevented. This can be accomplished, for example, by deletion of the POX gene coding for the acyl-CoA-oxidase. If the β-oxidation is eliminated, this leads to an increased ω-oxidation of the fatty acids (Smit et al. (2005) *Biotechnol. Lett.* 27: 859-864).

The microbial production of long-chain dicarboxylic acids has already been carried out with the aid of the yeast *C. tropicalis*:

Picataggio S, Rohrer T, Deanda K, Lanning D, Reynolds R, Mielenz J & Eirich L D (1992) Biotechnology (N.Y.) 10: 894-898.

In this case, the production of the dicarboxylic acids was primarily achieved by deletion of the genes POX4 and POX5. There are a number of patents which protect corresponding *C. tropicalis* production strains and relevant production methods (e.g. U.S. Pat. No. 4,339,536A, EP296506A2 and WO200017380A1).

In a 2013 patent specification it is described how yeasts in general (in a manner known per se) can be induced to produce increased quantities of dicarboxylic acids. In the exemplary embodiments however, only *C. tropicalis* is specifically discussed here (WO201306730A2, WO201306733A2).

The microbial production of long-chain ω-hydroxy fatty acids has also already been carried out with the aid of the yeast *C. tropicalis*:

Lu W, Ness J E, Xie W, Zhang X, Minshull J & Gross R A (2010) J Am Chem Soc 132: 15451-15455.

For this purpose, in addition to the genes POX4 and POX5, six cytochrome P450, four alcohol oxidase and six alcohol dehydrogenase genes were deleted. These strains and production methods are already protected under patent law (WO2011008232A2).

Furthermore, it has already been described how *Y. lipolytica* can be induced to form dicarboxylic acids:

Smit M S, Mokgoro M M, Setati E & Nicaud J M (2005) Biotechnol Lett 27: 859-864.

In this case, all the presently known acyl-CoA-oxidase genes (POX1, POX2, POX3, POX4, POX5 and POX6) as well as the acyl-CoA-diacylglycerol-acyltransferase gene (DGA1) and the lecithin-cholesterol-acyltransferase gene (LRO_1) were deleted. Furthermore, the NADPH-cytochrome P450-reductase gene (CPR1) was overexpressed (WO200664131A8).

In addition to the biotechnological production of ω-hydroxy fatty acids and dicarboxylic acids with the aid of genetically modified yeasts using the intracellular ω-oxidation of fatty acids, there are also other biotechnological methods based on other enzymatic conversions. An example of this is the use of Baeyer-Villiger monooxygenase, which catalyzes the conversion of a ketone to the ester (WO2013151393A1).

DETAILED DESCRIPTION

It is the object of the present invention to provide new types of yeast strains of the type *Y. lipolytica* which are suitable for the microbial production of ω-hydroxy fatty acids or dicarboxylic acids in larger quantities than previously known as well as a method for cultivating precisely these strains.

The object is solved by a yeast strain according to claim 1 and by methods according to claims 8 and 11. Advantageous embodiments are given in the dependent claims.

According to a first aspect of the invention, for the microbial production of ω-hydroxy fatty acids from hydrophobic substrates, a yeast strain of the type *Y. lipolytica* is provided, which exhibits a reduction in the activities of acyl-CoA oxidases (namely POX1: YALI0E32835g, POX2: YALI0F10857g, POX3: YALI0D24750g, POX4: YALI0E27654g, POX5: YALI0C23859g, POX6: YALI0E06567g), wherein in this yeast strain the activities of relevant (fatty) alcohol dehydrogenases (=(fatty acid) alcohol dehydrogenases, namely selected from FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g and/or ADH7: YALI0E07766g) are reduced and the activities of relevant (fatty) alcohol oxidases (=(fatty acid) alcohol oxidases, namely FAO1: YALI0B14014g) are reduced, which leads to an increased formation of ω-hydroxy fatty acids, preferably linear ω-hydroxy fatty acids according to the general structure: HOOC—$(CH_2)_n$—$CH_2OH$, HOOC—$(C_nH_{2n-2})$—$CH_2OH$, COOC—$(C_nH_{2n-4})$—$CH_2OH$ or HOOC—$(C_nH_{2n-6})$—$CH_2OH$, wherein n is in the range from 6 to 18, preferably in the range from 8 to 16, from a hydrophobic substrate, in particular a corresponding n-alkane or a fatty acid (and other hydrophobic substrates).

Particularly preferably the ω-hydroxy fatty acid is a linear ω-hydroxy fatty acid according to the general structure: HOOC—$(CH_2)_n$—$CH_2OH$ where n is in the range from 8 to 16.

The formation of ω-hydroxy fatty acids or dicarboxylic acids is increased in the sense of the present invention if this is increased compared with yeast cells without the corresponding genetic modification by at least 10 mol. %, particularly preferably at least 20 mol. %.

The invention is based on the recently obtained finding that the gene which codes for the fatty alcohol oxidase FAO1: YALI0B14014g in the yeast strain of the type *Y. lipolytica*, could be identified.

The inventors have additionally now surprisingly found that the deletion of the gene which codes for the enzyme Faolp reduces the further ω-oxidation of the ω-hydroxy fatty acids to the fatty acid aldehyde or to the dicarboxylic acid in the course of the ω-oxidation of fatty acids.

The reduction of the activity of the products of FADH, ADH1, ADH2, ADH3, ADH4, ADH5, ADH6, ADH7 and/or FAO1 particularly advantageously prevents or reduces the further oxidation of ω-hydroxy fatty acids to the fatty acid aldehyde or to the dicarboxylic acid in the course of the ω-oxidation of fatty acids.

The fatty alcohol oxidase gene has not yet been described so far in *Y. lipolytica*. Its use within the framework of biotechnological fields of application is also part of this invention.

A reduction in the activity of a protein is preferably to be understood that the activity of the protein per cell is reduced. Particularly preferably this is to be understood as the lack of activity of the protein in the yeast cell.

The reduction in the activity of proteins can be achieved by various methods known to the person skilled in the art such as, for example:
  (i) through the inhibition or reduction in the expression of the gene coding for this
  (ii) by partial or complete deletion of the genes coding for this
  (iii) by expression of non-functional genes
  (iv) by inhibition or reduction in the activity of the expressed genes.

The inhibition or reduction of the expression of a gene coding for a protein can, for example, be accomplished by inhibition or reduction of the transcription of the coding gene or the translation of the mRNA formed. The deletion of the coding genes can be performed, for example, by a removal of the genes by means of deletion cassettes. The expression of a dysfunctional or activity-reduced gene product can be accomplished, for example, by insertion, substitution or point mutation in the gene coding for the protein.

The deletion of a coding gene is preferred for the reduction in activity.

The yeast strain according to the invention for the production of ω-hydroxy fatty acids thus exhibits a deletion of the genes for the acyl-CoA oxidases (POX1, POX2, POX3, POX4, POX5 and POX6) as well as for the (fatty) alcohol dehydrogenases (FADH, ADH1, ADH2, ADH3, ADH4, ADH5, ADH6, ADH7) and/or for the (fatty) alcohol oxidases (FAO1). Furthermore, the formation of lipid bodies is reduced, preferably due to the reduction in the activity of the gene products of PAH1 and/or SCT1.

The deletion of the genes POX1, POX2, POX3, POX4, POX5 and POX6 prevents the β-oxidation and thus inhibits the breakdown of fatty acids (to acetyl-CoA or propionyl-CoA).

Preferably in the yeast strain according to the invention for the microbial production of ω-hydroxy fatty acids, the activities of individual or all cytochrome P450-gene products, in particular of ALK1: YALI0E25982g, ALK2: YALI0F01320g, ALK3: YALI0A20130g, ALK4: YALI0B13816g, ALK5: YALI0B13838g, ALK6: YALI0B01848g, ALK7: YALI0A15488g, ALK8: YALI0C12122g, ALK9: YALI0B06248g, ALK10: YALI0B20702g, ALK11: YALI0C10054g and/or ALK12: YALI0A20130g are additionally increased. Advantageously the increase in individual or all cytochrome P450-gene products results in an increased formation of ω-hydroxy fatty acids from the corresponding hydrophobic salt, in particular n-alkanes and fatty acids.

It can be advantageous that in the yeast strain according to the invention for the microbial production of ω-hydroxy fatty acids, the activity of the NADPH-cytochrome P450-reductase (CPRI: YALI0D04422g) is additionally increased, which leads to an increased formation of ω-hydroxy fatty acids from the corresponding hydrophobic substrate, in particular n-alkanes and fatty acids.

Preferably in the yeast strain according to the invention for the microbial production of ω-hydroxy fatty acids, the activity of the phosphatidic acid-dephosphohydrolase (PAH1: YALI0D27016p) is additionally reduced. Advantageously this leads to a reduction in the size of the lipid bodies and therefore to an increased formation of ω-hydroxy fatty acids or dicarboxylic acids from the corresponding hydrophobic substrate, in particular n-alkanes and fatty acids.

According to a preferred embodiment of the present invention, in the yeast strain according to the invention for the microbial production of ω-hydroxy fatty acids, the activity of the glycerol-3-phosphate-acyltransferase (SCT1: YALI0C00209g) is additionally reduced, which advantageously leads to a reduction in the size of the lipid bodies and therefore to an increased formation of ω-hydroxy fatty acids from the corresponding hydrophobic substrate, in particular n-alkanes and fatty acids (and other hydrophobic substrates).

It can also be further provided that in the yeast strain according to the invention for the microbial production of ω-hydroxy fatty acids, the activity of the phospholipid-diacylglycerol-acyltransferase (LRO1: YALI0E16797g) is additionally reduced, which leads to a reduction in the size of the lipid bodies and therefore to an increased formation of ω-hydroxy fatty acids from the corresponding hydrophobic substrate, in particular n-alkanes and fatty acids.

According to a preferred embodiment of the present invention, in the yeast strain according to the invention for the microbial production of ω-hydroxy fatty acids, the activity of the diacylglycerol-acyltransferase (DGAJ: YALI0E32769g) is additionally reduced, which leads to a reduction in the size of the lipid bodies and therefore to an increased formation of ω-hydroxy fatty acids from the corresponding hydrophobic substrate, in particular n-alkanes and fatty acids.

According to a preferred embodiment of the present invention, in the yeast strain according to the invention for the microbial production of ω-hydroxy fatty acids, the activity of the glycerol-3-phosphate-dehydrogenase (GUT2: YALI0B13970g) is additionally increased, which leads to a reduction in the size of the lipid bodies and therefore to an increased formation of ω-hydroxy fatty acids from the corresponding hydrophobic substrate, in particular n-alkanes and fatty acids.

It was particularly advantageously now found that the additional increase in the activities of relevant triacylglycerol lipases (TGL3/TGL4: YALI0F10010g, YALI0D16379g, YALI0D17534g) in the yeast strain according to the invention for the microbial production of ω-hydroxy fatty acids, leads to a reduction in the size of the lipid bodies and therefore to an increased formation of ω-hydroxy fatty acids from the corresponding hydrophobic substrate, in particular n-alkanes and fatty acids.

The reduction in the activity of the citrate and oxalacetate transporters (YHM2: YALI0B10736g) and/or the reduction in the activity of the citrate transport protein (CTP1: YALI0F26323g) in the yeast strain according to the invention for the microbial production of ω-hydroxy fatty acids has proved to be particularly advantageous since as a result, a smaller quantity of organic acids is produced and/or secreted into the culture medium.

It can optionally be provided that in the yeast strain according to the invention for the microbial production of ω-hydroxy fatty acids, the transport of ω-hydroxy fatty acids from the yeast cell or from the endoplasmic reticulum into the cytoplasm is additionally increased, e.g. due to the increased activity of specific membrane transporters, which leads to an increased formation of ω-hydroxy fatty acids from the corresponding hydrophobic substrate, in particular n-alkanes and fatty acids.

Preferably in the yeast strain according to the invention for the microbial production of ω-hydroxy fatty acids, the transport of the hydrophobic substrate into the yeast cell or the respective organelles (peroxisomes, endoplasmic reticulum), is additionally increased, e.g. due to the increased activity of specific membrane transporters, which leads to an increased formation of ω-hydroxy fatty acids from the corresponding hydrophobic substrate, in particular n-alkanes and fatty acids.

The invention also relates to the use of the yeast strain according to the invention for the microbial production of ω-hydroxy fatty acids having the general structure: HOOC—$(CH_2)_n$—OH, HOOC—$(C_nH_{2n-2})$—$CH_2OH$, COOC—$(C_nH_{2n-4})$—$CH_2OH$ or HOOC—$(C_nH_{2n-6})$—$CH_2OH$, where n is in the range from 6 to 18, from a hydrophobic substrate.

The invention also comprises a yeast strain of the type Y. lipolytica for the microbial production of dicarboxylic acids from n-alkanes and fatty acids (and other hydrophobic substrates) which exhibit a reduction in the activities of acyl-CoA oxidases (namely POX1: YALI0E32835g, POX2: YALI0F10857g, POX3: YALI0D24750g, POX4: YALI0E27654g, POX5: YALI0C23859g, POX6: YALI0E06567g) and is characterized in that in this yeast strain the activities of relevant (fatty) alcohol dehydrogenases (namely selected from FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g and/or ADH7: YALI0E07766g) and the activities of relevant (fatty) alcohol oxidases (namely FAO1: YALI0B14014g) are additionally increased, which leads to an increased formation of dicarboxylic acids, preferably according to the general structure: HOOC—$(CH_2)_n$—COOH, HOOC—$(C_nH_{2n-2})$—COOH, COOC—$(C_nH_{2n-4})$—COOH or HOOC—$(C_nH_{2n-6})$—COOH, where n is in the range from 6 to 18, preferably in the range from 8 to 16, from n-alkanes and fatty acids (and other hydrophobic substrates).

The yeast strain according to the invention for the production of dicarboxylic acids preferably exhibits a deletion of the genes POX1, POX2, POX3, POX4, POX5 and POX6. In addition, it exhibits an increased activity of the products of FADH, ADH1, ADH2, ADH3, ADH4, ADH5, ADH6, ADH7 and/or FAO1. Furthermore, the formation of lipid bodies is reduced, preferably due to the reduction in the activity of gene products of PAH1 and/or SCT1.

Particularly advantageously, the increase in activity of the gene products of FADH, ADH1, ADH2, ADH3, ADH4, ADH5, ADH6, ADH7 and/or FAO1 intensifies the further oxidation of ω-hydroxy fatty acids to fatty acid aldehyde or to dicarboxylic acid in the course of the ω-oxidation of fatty acids, so that the desired dicarboxylic acids are increasingly formed.

An increased activity of a protein is preferably to be understood that the activity per cell is increased which can be achieved by the increase in the quantity of protein or by the increase in the protein's own activity. The increase in the quantity of protein is characterized in that more protein is formed than for an unmodified strain under the same conditions. The increase in the protein's own activity is characterized in that the same quantity of protein has a higher activity in a modified strain than in an unmodified strain.

An increased activity of the proteins can be produced in various ways:
 (i) by introducing the relevant gene in multiple, preferably 8 to 12-fold, copy into the genome of the organism (gene-dose effect)
 (ii) by exchange of the natural promoter of the relevant gene by a stronger promoter than the natural promoter, preferably a promoter which possesses at least 50% of the activity of the promoter of the translation elongation factor 1 of the alpha-gene (TEF1:

YALI0C09141g), most preferably a promoter which possesses at least the activity of the TEF1 promoter. In this case promoters can be selected which are either active during the entire cultivation or only in a desired growth phase (gene regulation effect).

For the increase in activity, the additional introduction of the relevant gene under control of a strong promoter is particularly preferred, preferably the TEF1 promoter from *Yarrowia lipolytica*.

According to the invention, the yeast strains of the type *Y. lipolytica* for the production of ω-hydroxy fatty acids or dicarboxylic acids are not capable of breaking down fatty acids in the course of the β-oxidation. This can be ensured, for example, by the following measures:

(i) Reduction in the activity of acyl-CoA oxidases (POX1: YALI0E32835g, POX2: YALI0F10857g, POX3: YALI0D24750g, POX4: YALI0E27654g, POX5: YALI0C23859g, POX6: YALI0E06567g)

(ii) Prevention of peroxisome biogenesis, e.g. by reduction in the activity of the peroxines (e.g. PEX10: YALI0C01023g)

For the production of ω-hydroxy fatty acids, in addition to the prevention of β-oxidation, the oxidation of ω-hydroxy fatty acids to fatty acid aldehyde or to dicarboxylic acid in the course of ω-oxidation must be prevented or reduced. This can be achieved as follows:

(i) Reduction in the activity of relevant (fatty) alcohol dehydrogenases (FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g, ADH7: YALI0E07766g)

(ii) Reduction in the activity of relevant (fatty) alcohol oxidases (FAO1: YALI0B14014g)

The product yield is preferably further increased by the direct influencing of relevant metabolic pathways, in particular these are:

(i) increasing the activity of the cytochrome P450-gene products (ALK1: YALI0E25982g, ALK2: YALI0F01320g, ALK3: YALI0A20130g, ALK4: YALI0B13816g, ALK5: YALI0B13838g, ALK6: YALI0B01848g, ALK7: YALI0A15848g, ALK8: YALI0C12122g, ALK9: YALI0B06248g, ALK10: YALI0B20702g, ALK11: YALI0C10054g, ALK12: YALI0A20130g)

(ii) increasing the activity of the NADPH-cytochrome P450-reductase (CPR1: YALI0D04422g)

Only for the production of dicarboxylic acids:

(iii) increasing the activity of relevant (fatty) alcohol dehydrogenases (FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g, ADH7: YALI0E07766g)

(iv) increasing the activity of relevant (fatty) alcohol oxidases (FAO1: YALI0B14014g)

(v) increasing the activity of relevant (fatty) aldehyde dehydrogenases (FALDH1: YALI0A17875g, FALDH2: YALI0E15400g, FALDH3: YALI0B01298g, FALDH4: YALI0F23793g)

In the course of our investigations, it was established that the cells form very large lipid bodies in the course of cultivation. It can be assumed that the fatty acids (or intracellular derivatives thereof) are esterified with glycerol and stored intracellularly in the lipid bodies. This reduces the product yield ultimately achieved:

Genetic modifications preferably result in the formation of smaller lipid bodies and therefore in an increased product yield, in particular these are:

(i) reduction in the activity of phosphatidic acid dephosphohydrolase (PAH1: YALI0D27016p)

(ii) reduction in the activity of phospholipid diacylglycerol acyltransferase (LRO1: YALI0E16797g)

(iii) reduction in the activity of diacylglycerol acyltransferase (DGA1: YALI0E32769g)

(iv) reduction in the activity of glycerol-3-phosphate acyltransferase (SCT1: YALI0C00209g)

(v) increase in the activity of glycerol-3-phosphate dehydrogenase (GUT2: YALI0B13970g)

(vi) increase in the activity of triacylglycerol lipases (TGL3/TGL4: YALI0F10010g, YALI0D16379g, YALI0D17534g)

In particular, the reduction in the activity of phosphatidic acid dephosphohydrolase, diacyl-glycerol acyltransferase and/or glycerol-3-phosphate acyltransferase result in an increased product yield, i.e. production of ω-hydroxy fatty acids or dicarboxylic acids.

Furthermore, transport of the substrates into the cell or the respective organelles (peroxisomes, endoplasmic reticulum) as well as transport of the products (ω-hydroxy fatty acids and dicarboxylic acids) from the cell or from the respective organelles is increased. This can be ensured, for example, by the increase in the activity of specific transporters.

According to a particularly preferred embodiment of the present invention, the combination of several of the aforesaid genetic modifications results in an increased product yield, an increased output and/or an increased space-time yield.

A wild type isolate of the yeast *Y. lipolytica*, preferably of the strain H222 can be used as the starting strain for the construction of a strain according to the invention. The strain H222 was deposited on 29 Apr. 2013 at the DSMZ (Deutsche Sammlung für Mikroorganismen und Zellkulturen GmbH, D-38142 Braunschweig) under the number DSM 27185 according to the Budapest Treaty on the international Recognition of the Deposit of Microorganisms for the Purposes of Patent Procedure.

A selection marker is required for the use of a strain for further genetic processing. This selection marker can be introduced into the strain in a manner known per se, e.g. in the form of the uracil auxotroph. Alternatively, already known uracil auxotrophic strains can be used, preferably the strain H222-S4 (Mauersberger S, Wang H J, Gaillardin C, Barth G & Nicaud J M (2001) J Bacteriol 183: 5102-5109).

Additional genes or constructs are introduced, which replace the existing genes, preferably by means of usual methods known in the prior art. In order to ensure an efficient transcription of the introduced genes, it is preferable to link promoters functioning for the organism to the open reading frame of the genes. In this case, both constitutive promoters and also promoters dependent on the cultivation conditions can be used.

Preferably the introduced genes which code for the said enzymes are placed functionally under the control of a constitutive promoter, where the promoters can be identical or different from one another.

Preferably constitutive promoters are used. Particularly preferably the promoter of the translation elongation factor 1 alpha (pTEF1) is used.

Alternatively preferably the introduced genes are placed under the control of a promoter which is dependent on the cultivation conditions. Preferably activators or inductors activate the promoter which is dependent on the cultivation conditions (in the sense of the application also called operator) by interacting directly with a controllable promoter or by binding to a repressor protein which then detaches from the promoter. As a result of the contact of the yeast strain according to the invention with the activator and/or inductor, the aforesaid enzymes are synthesized in the yeast strain according to the invention and are thus available for the biocatalytic conversion of a hydrophobic substrate, in particular of a corresponding n-alkane or a fatty acid.

In one embodiment of the invention, the promoters dependent on the cultivation conditions differ from one another so that the promoters are activatable in a primary-signal specific manner. The presence of different activators and/or inductors in the yeast strain can thus advantageously lead to the expression of selected genes, whereby the stress for a recombinant yeast cell is reduced.

The corresponding nucleic acid sequences for promoters (for example, pTEF1, pPOX2, pPOT1, pXPR1, pICL1), which can be used for a method according to the invention are extremely well known to the person skilled in the art or can be deduced from known databases. Advantageously for a method according to the invention, natural promoters can also be used in addition to promoters introduced artificially into the organisms.

Likewise it is preferable to provide the open reading frame of the genes with a terminator. Preferably the terminator of the gene of the isocitrate lyase (ICL1t) is used.

The subject matter of the invention is also a method for the biocatalytic production of ω-hydroxy fatty acids, preferably according to the general structure: HOOC—$(CH_2)_n$—$CH_2OH$, HOOC—$(C_nH_{2n-2})$—$CH_2OH$, COOC—$(C_nH_{2n-4})$—$CH_2OH$ or HOOC—$(C_nH_{2n-6})$—$CH_2OH$, where n is in the range from 6 to 18, preferably in the range from 8 to 16, from a hydrophobic substrate, which comprises the following steps:
  a) preparation of yeast cells of at least one yeast strain of the type *Y. lipolytica*, which exhibits
    (i) a reduction of the activities of the acyl-CoA oxidases,
    (ii) a reduced activity of relevant (fatty) alcohol dehydrogenases and
    (iii) a reduced activity of relevant (fatty) alcohol oxidases in a suitable cultivation medium,
  b) contacting the yeast cells with the hydrophobic substrate, wherein the hydrophobic substrate is reacted with at least one of the enzymes of the yeast cells selected from the group,
    (i) of cytochrome P450-gene products,
    (ii) of NADPH-cytochrome P450 reductase,
    (iii) of (fatty) alcohol dehydrogenases
    to give the reaction product ω-hydroxy fatty acid,
  c) isolation of the dicarboxylic acid.

Particularly preferably the ω-hydroxy fatty acid is a linear ω-hydroxy fatty acid having the general structure HOOC—$(CH_2)_n$—$CH_2OH$ where n is in the range from 8 to 16.

According to a preferred embodiment of the method according to the invention for the biocatalytic production of ω-hydroxy fatty acids, it can be provided that the reaction to give the reaction product ω-hydroxy fatty acid additionally takes place with (fatty) alcohol oxidases, (fatty) alcohol dehydrogenases remaining in the yeast cells used.

Preferably the yeast cells of at least one yeast strain in the method according to the invention for the biocatalytic production of ω-hydroxy fatty acids of the type *Y. lipolytica* are selected from the yeast strain according to the invention for the microbial production of ω-hydroxy fatty acids.

It has surprisingly been shown that after the biocatalytic conversion of the hydrophobic substrate to the desired reaction product ω-hydroxy fatty acids, these are not further metabolized in the yeast cells according to the invention of a yeast strain of the type *Y. lipolytica* (i.e. broken down in the metabolism of the whole cell catalyst) and accumulate in the aqueous component. Advantageously the ω-hydroxy fatty acid accumulates as a consequence of the discharge from the yeast cells in the cultivation medium.

Preferably the contacting of the yeast strain with a hydrophobic substrate takes place by direct addition to the liquid component in the form of liquid and/or solid. During direct addition to the yeast strain, an organic phase can additionally be used as substrate reservoir, whereby the process run time can be optimized.

In the sense of the present invention, a hydrophobic substrate is to be understood as a per se water-insoluble substance having an optionally branched and/or unsaturated hydrocarbon scaffold with 8 to 20 carbon atoms. Preferably the hydrophobic substrate is selected from the group of n-alkanes having the general structure: $H_3C$—$(CH_2)_n$—$CH_3$ (for example, dodecane, pentadecane, hexadecane) or alkenes having the general structure $H_3C$—$(CH_2)_n$—$CH_3$, $H_3C$—$(C_nH_{2n-4})$—$CH_3$ or $H_3C$—$(C_nH_{2n-6})$—$CH_3$, where n is an integer in the range from 6 to 18, the optionally branched saturated fatty acids having the general structure: HOOC—$(CH_2)_n$—$CH_3$, where n is an integer in the range from 6 to 18 (for example, dodecanoic acid, hexadecanoic acid, pentadecanoic acid, phytanic acid), the unsaturated fatty acids having the general structure: HOOC—$(C_nH_{2n-2})$—$CH_3$, COOC—$(C_nH_{2n-4})$—$CH_3$ or HOOC—$(C_nH_{2n-6})$—$CH_3$, where n is an integer in the range from 6 to 18 (for example, oleic acid, linoleic acid, arachidonic acid), and fatty acid alkyl esters having the general structure: ROOC—$(CH_2)_n$—$CH_3$, where n is in the range from 6 to 18 and where R is an optionally branched $C_{1-4}$-alkyl group.

Particularly preferably but not exclusively aforesaid n-alkanes, alkenes or saturated or unsaturated fatty acids having a chain length (number of carbon atoms of the longest chain) from eight to eighteen carbon atoms, i.e., n in the range from 6 to 16 serve as hydrophobic substrate for the bioconversion.

According to an alternatively preferred embodiment of the present invention, preferably but not exclusively n-alkanes and fatty acids having a chain length of eight to eighteen carbon atoms, i.e. n in the range from 6 to 16, serve as hydrophobic substrate for the bioconversion.

According to a preferred embodiment of the method according to the invention, the concentration of the hydrophobic substrate at the beginning of production is 1 to 50 grams per litre of culture medium (g $l^{-1}$), particularly preferred is 5 to 40 g $l^{-1}$.

The invention further relates to a method for the production of dicarboxylic acids, preferably according to the general structure: HOOC—$(CH_2)_n$—COOH, HOOC—$(C_nH_{2n-2})$—COOH, COOC—$(C_nH_{2n-4})$—COOH or HOOC—$(C_nH_{2n-6})$—COOH, where n is in the range from 6 to 18, preferably in the range from 8 to 16, from a hydrophobic substrate, in particular selected from n-alkanes and fatty acids, comprising the following steps:
  a) preparation of yeast cells of at least one yeast strain of the type *Y. lipolytica*, which exhibits
    (i) a reduction of the activities of the acyl-CoA oxidases,
    (ii) an enhanced activity of relevant (fatty) alcohol dehydrogenases and
    (iii) an enhanced activity of relevant (fatty) alcohol oxidases in a suitable cultivation medium, b) contacting the yeast cells with the hydrophobic substrate, wherein the hydrophobic substrate is reacted with at least one of the enzymes of the yeast cells selected from the group,
  (i) of cytochrome P450-gene products,
  (ii) of NADPH-cytochrome P450-reductase,
  (iii) of (fatty) alcohol dehydrogenases according to a),
  (iv) of (fatty) alcohol oxidases according to a) and
  (v) (fatty) aldehyde dehydrogenases
  to give the reaction product dicarboxylic acid,
c) isolation of the dicarboxylic acid.

Particularly preferably the dicarboxylic acid is a linear dicarboxylic acid according to the general structure: HOOC—$(CH_2)_n$—$CH_2OH$ where n is in the range from 8 to 16.

Preferably in the yeast cells for the method according to the invention for the production of ω-hydroxy fatty acids or dicarboxylic acids, the activities of individual or all cytochrome P450-gene products, in particular of ALK1: YALI0E25982g, ALK2: YALI0F01320g, ALK3: YALI0A20130g, ALK4: YALI0B13816g, ALK5: YALI0B13838g, ALK6: YALI0B01848g, ALK7: YALI0A15488g, ALK8: YALI0C12122g, ALK9: YALI0B06248g, ALK10: YALI0B20702g, ALK11: YALI0C10054g and/or ALK12: YALI0A20130g are additionally increased. Advantageously the increase of individual or all cytochrome P450-gene products leads to an increased formation of ω-hydroxy fatty acids or dicarboxylic acids from the corresponding hydrophobic substrate, in particular n-alkanes and fatty acids.

It can advantageously be provided that in the yeast cells for the method according to the invention for the production of ω-hydroxy fatty acids or dicarboxylic acids, the activity of the NADPH-cytochrome P450-reductase (CPR1: YALI0D04422g) is additionally increased, which leads to an increased formation of ω-hydroxy fatty acids or dicarboxylic acids from the corresponding hydrophobic substrate, in particular n-alkanes and fatty acids.

According to a preferred embodiment of the method according to the invention for the production of dicarboxylic acids, in the yeast cells the activities of relevant (fatty) alcohol dehydrogenases (namely FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g, ADH7: YALI0E07766g) can be additionally increased, which advantageously leads to an increased formation of dicarboxylic acids from the corresponding hydrophobic substrate, in particular n-alkanes and fatty acids.

Preferably in the yeast cells of the method according to the invention for the production of dicarboxylic acids, the activities of relevant (fatty) alcohol oxidases (FAO1: YALI0B14014g) are additionally increased, which leads to an increased formation of dicarboxylic acids from the corresponding hydrophobic substrate, in particular n-alkanes and fatty acids.

According to a preferred embodiment of the method according to the invention for the production of dicarboxylic acids, in the yeast cells the activities of relevant (fatty) alcohol dehydrogenases (FALDH1: YALI0A17875g, FALDH2: YALI0E15400g, FALDH3: YALI0B01298g, FALDH4: YALI0F23793g) are additionally increased, which leads to an increased formation of dicarboxylic acids from the corresponding hydrophobic substrate, in particular n-alkanes and fatty acids.

Preferably the yields of ω-hydroxy fatty acids or dicarboxylic acids in the method according to the invention over a period of one day (i.e. 24 h) lie in the range from 1 to 20 g $l^{-1}$, particularly preferably in the range from 4 to 15 g $l^{-1}$.

According to a preferred embodiment of the invention, the production of ω-hydroxy fatty acids and dicarboxylic acids takes place in a bioreactor (fermenter) in which a yeast strain according to the invention is fermented under suitable growth conditions in a suitable cultivation medium.

The invention further relates to method for producing ω-hydroxy fatty acids and dicarboxylic acids which are characterized in that a micro-organism according to the invention is cultivated in a manner known per se in a bioreactor (fermenter).

Preferably the reaction product ω-hydroxy fatty acids and dicarboxylic acids, are isolated by extraction of the aqueous component with an organic solvent selected from the group of phthalic acid esters, particularly preferably ethylacetate, 1,2-cyclo-hexane dicarboxylic acid diisononylester and Mesamoll®, and/or the aliphatic branched and/or linear hydrocarbons, preferably with 5 to 16 carbon atoms such as, for example, n-pentane, cyclopentane, n-hexane, cyclohexane, n-heptane, n-octane, cyclooctane, n-decane, n-dodecane or n-hexadecane. Preferably the said organic solvents are used in a single-phase aqueous system for extraction after conversion of the hydrophobic substrate. Alternatively the said organic solvents are used in a two-phase system in the form of a second phase in addition to the cultivation medium as a reservoir for the hydrophobic substrate and/or for separation of the reaction product.

The isolation of the dicarboxylic acids and/or ω-hydroxy fatty acids by extraction of the aqueous component with an organic solvent preferably takes place after separation of the yeast cells in the form of biomass from the cultivation medium, where the separation of the yeast cells in the form of biomass from the cultivation medium is preferably accomplished by centrifugation or filtration.

Preferably the extraction of the reaction products ω-hydroxy fatty acids and dicarboxylic acids is accomplished with an organic solvent with a pH between 0 and 8, particularly preferably between 1 and 7, quite particularly preferably between 1 and 6.

Optionally a distillation is accomplished following the extraction for purification of the dicarboxylic acids and/or ω-hydroxy fatty acid, where preferably the organic solvent is separated. Preferably the organic solvent is separated by evaporation at a pressure between 0.1 and 1000 mbar, particularly preferably between 0.1 and 750 mbar, quite particularly preferably between 1 and 400 mbar.

Preferably in a yeast strain for the method according to the invention for the production of ω-hydroxy fatty acids or dicarboxylic acids, the activity of the phosphatidic acid dephosphohydrolase (PAHL YALI0D27016p) is additionally reduced. Advantageously this leads to a reduction in the size of the lipid bodies and therefore to an increased formation of ω-hydroxy fatty acids or dicarboxylic acids from the corresponding hydrophobic substrate, in particular n-alkanes and fatty acids.

According to a preferred embodiment of the method according to the invention for the production of ω-hydroxy fatty acids or dicarboxylic acids, in the yeast strain used the activity of the glycerol-3-phosphate acyltransferase (SCT1: YALI0C00209g) is additionally reduced, which advantageously leads to a reduction in the size of the lipid bodies and therefore to an increased formation of ω-hydroxy fatty acids or dicarboxylic acids from the corresponding hydrophobic substrate, in particular n-alkanes and fatty acids (and other hydrophobic substrates).

It can further be provided that in the method according to the invention for the microbial production of ω-hydroxy fatty acids or dicarboxylic acids, in the yeast cells of the yeast strain used, the activity of the phospholipid diacylglycerol acyltransferase (LRO1: YALI0E16797g) is additionally reduced, which leads to a reduction in the size of the lipid bodies and therefore to an increased formation of ω-hydroxy fatty acids or dicarboxylic acids from the corresponding hydrophobic substrate, in particular n-alkanes and fatty acids.

According to a preferred embodiment of the present invention, in the yeast strain according to the invention for the microbial production of ω-hydroxy fatty acids or dicarboxylic acids, the activity of the diacylglycerol acyltransferase (DGA1: YALI0E32769g) is additionally reduced, which leads to a reduction in the size of the lipid bodies and therefore to an increased formation of ω-hydroxy fatty acids or dicarboxylic acids from the corresponding hydrophobic substrate, in particular n-alkanes and fatty acids.

According to a preferred embodiment of the method according to the invention for the production of ω-hydroxy fatty acids or dicarboxylic acids, in the yeast cells of the appropriately used yeast strain, the activity of the glycerol-3-phosphate dehydrogenase (GUT2: YALI0B13970g) is additionally increased, which leads to a reduction in the size of the lipid bodies and therefore to an increased formation of ω-hydroxy fatty acids or dicarboxylic acids from the corresponding hydrophobic substrate, in particular n-alkanes and fatty acids.

Particularly advantageously, it was now found that the additional increase in the activities of relevant triacylglycerol lipases (TGL3/TGL4: YALI0F10010g, YALI0D16379g, YALI0D17534g) in the yeast cells used for the microbial production of ω-hydroxy fatty acids or dicarboxylic acids, leads to a reduction in the size of the lipid bodies and therefore to an increased formation of ω-hydroxy fatty acids or dicarboxylic acids from the corresponding hydrophobic substrate, in particular n-alkanes and fatty acids.

Preferably in the yeast cells of the yeast strain used for the method according to the invention for the production of ω-hydroxy fatty acids or dicarboxylic acids, the transport of the hydrophobic substrates into the yeast cell or the respective organelles (peroxisomes, endoplasmic reticulum), is additionally increased, e.g. due to the increased activity of specific membrane transporters, which leads to an increased formation of ω-hydroxy fatty acids or dicarboxylic acids from the corresponding hydrophobic substrate, in particular n-alkanes and fatty acids.

Optionally it can be provided that in the yeast cells for the microbial production of ω-hydroxy fatty acids or dicarboxylic acids, the transport of ω-hydroxy fatty acids and dicarboxylic acids from the yeast cell or from the endoplasmic reticulum into the cytoplasm is additionally increased, e.g. due to the increased activity of specific membrane transporters, which leads to an increased formation of ω-hydroxy fatty acids or dicarboxylic acids from the corresponding hydrophobic substrate, in particular n-alkanes and fatty acids and enrichment in the culture medium.

The reduction in the activity of the citrate and oxalacetate transporter (YHM2: YALI0B10736g) and/oor the reduction in the activity of the citrate transport protein (CTP1: YALI0F26323g) in the yeast cells has proved to be particularly advantageous for the method according to the invention for the microbial production of ω-hydroxy fatty acids or dicarboxylic acids since as a result, a smaller quantity of organic acids is produced and/or is secreted in the culture medium.

Preferably the cultivation medium is a minimal medium. A minimal medium is understood in the sense of the present invention as an aqueous culture medium which contains all the substrates required for the growth of yeast cells (for example, C source, mineral salts, trace elements, vitamins) in dissolved form but which at the same time has no complex ingredients or complex biomolecules (e.g. yeast extract, peptone, tryptone etc.). The person skilled in the art is familiar with a plurality of minimal media for the cultivation of yeast cells from the prior art.

In addition to the hydrophobic substrate supplied for the bioconversion, another carbon source (C source; substrate for energy recovery) on the basis of which the cell can acquire energy, needs to be provided for the cultivation.

Preferably therefore mono- or disaccharides, for example, glucose, D-fructose, xylose, maltose, saccharose and/or polyvalent alcohols, such as for example, glycerol, raw glycerol and mannitol are added to the cultivation medium as C source, glucose being particularly preferred as the added carbon source.

In particular, ammonium/ammonia or amino acids such as glutamine/glutamate serve as nitrogen source (N source) for the cultivation of yeast strains in the method according to the invention.

For the cultivation of a strain according to the invention, cultivation conditions under which the lipid bodies are comparatively weakly defined and the conversion rate of the supplied substrates are comparatively strongly defined are to be preferred.

A limitation of the cell growth prevents too large quantities of the substrate used being stored in the cells, which reduces the product yield, and prevents the occurrence of oxygen limitation which lowers the productivity.

A possible form of limitation is nitrogen limitation. This limitation in the yeast *Y. lipolytica* results in a stoppage of growth after consumption of the nitrogen source and in the formation of citric acid and iso-citric acid. Preferably the nitrogen content in the medium during the production phase, i.e. after contact of the yeast cells with the hydrophobic substrate, should be less than 2 g $l^{-1}$, preferably less than 1 g $l^{-1}$, highly preferably less than 0.5 g $l^{-1}$, most preferably 0 g $l^{-1}$. The production phase is characterized in that it follows a phase of strong growth (growth phase) and only exhibits (compared to the growth rate) low growth but increased product formation.

Preferably cultivation takes place in the fermenter under controlled process parameters, where particularly preferably the pH is kept constant in the cultivation medium (during a specific growth phase). In particular, the fermentation takes place under limitation conditions.

The pH in the cultivation medium after contact, i.e. during the growth phase, should correspond to the physiologically preferred value of 5.5 and during the production phase, i.e. after contact of the yeast cells with the hydrophobic substrate, should preferably be 5.5-9.0, particularly preferably 7.0-9.0 and especially preferably 8.0.

Preferably the yeast cells are cultivated under physiological conditions at a temperature between 0 and 60° C., preferably between 10 and 50° C., particularly preferably between 20 and 40° C., where the pH of the cultivation medium lies between 2.0 and 9.0, preferably between 5.5 and 9.0, particularly preferably between 7.0 and 9.0, especially preferably around 8.0.

Preferably in the method according to the invention, the said limitation conditions are combined with one another.

The subject matter of the invention is also a kit for the biocatalytic production of dicarboxylic acids or ω-hydroxy fatty acids containing:
a) at least one type of yeast cells, preferably a type of yeast cells modified according to the invention of the yeast strain of the type *Y. lipolytica* in an aqueous component and/or
b) at least one type of cryo-conserved yeast cells, preferably a type of yeast cells modified according to the invention of the yeast strain of the type *Y. lipolytica*.

The biomass in the form of yeast cells for the method according to the invention for the biocatalytic production of dicarboxylic acids or ω-hydroxy fatty acids can be obtained in a manner known to the person skilled in the art involving pre-cultivation of the corresponding yeast cells to be used (propagation on full medium and/or minimal medium, for example, by cultivation in full medium such as YPD-Medium (DSM-Medium No. 393), but preferably by cultivation in a medium which allows the production of high cell densities, for example, by cultivation in minimal medium (for example, 5% (w/v) glucose, 20 g $CaCO_3$, 1 g $l^{-1}$ $KH_2PO_4$, 0.16 g $l^{-1}$ $K_2HPO_4 \times 3$ $H_2O$, 3 g $l^{-1}$ $(NH_4)_2SO_4$, 0.7 g $l^{-1}$ $MgSO_4 \times 7$ $H_2O$, 0.5 g $l^{-1}$ NaCl, 0.4 g $l^{-1}$ $Ca(NO_3)_2 \times 4$ $H_2O$, 0.5 mg $l^{-1}$ $H_3BO_3$, 0.0 mg $l^{-1}$ $CuSO_4 \times 5$ $H_2O$, 0.1 mg $l^{-1}$ KI, 0.4 mg $l^{-1}$ $MnSO_4 \times 4$ $H_2O$, 0.2 mg $l^{-1}$ $Na_2MoO_4 \times 2$ $H_2O$, 0.4 mg $l^{-1}$ $ZnSO_4 \times 7$ $H_2O$, 6 mg $l^{-1}$ $FeCl_3 \times 6$ $H_2O$, 0.3 mg $l^{-1}$ thiamine hydrochloride) in particular, greater than $1 \times 10^9$ cells per ml. The propagation of this pre-culture of the yeast cells of the kit according to the invention is preferably accomplished in conventional laboratory shaking flasks, but propagation under controlled conditions in the fermenter is also possible to produce larger quantities of biomass.

A further aspect of the invention also relates to the use of yeast cells modified according to the invention of the yeast strain of the type *Y. lipolytica*, a method according to the invention or a kit according to the invention.

Preferred further developments of the invention are obtained from the combinations or the claims or individual features thereof.

The invention will be explained in detail hereinafter with reference to some exemplary embodiments and relevant figures. The following examples are used to further explain the invention without restricting the invention to these.

BRIEF DESCRIPTION OF THE DRAWINGS

In the figures:

FIG. 5 A-C: shows the accumulation of dodecanoic diacid and ω-hydroxydodecanoic acid in the cultivation of various strains of the yeast *Y. lipolytica* using dodecane as substrate. FIG. 5A—*Y. lipolytica* H222ΔPΔAΔF formed only small quantities of dicarboxylic acids and is thus the preferred initial strain for the construction of production strains for ω-hydroxy fatty acids.

FIG. 6 A-B: shows the (fatty) alcohol dehydrogenase and oxidase enzyme activity in the cultivation of various strains of the yeast *Y. lipolytica* using dodecane as substrate.

EXPLANATIONS ON THE GENETIC MODIFICATIONS

ΔP Deletion of the acyl-CoA oxidase genes (POX1-6)
ΔF Deletion of the (fatty) alcohol oxidase gene (FAO1)
ΔA Deletion of the (fatty) alcohol dehydrogenase genes (FADH, ADH1-7)
ΔD Deletion of the diacylglycerol acyltransferase gene (DGA1)
ΔH Deletion of the phosphatidic acid dephosphohydrolase gene (PAH1)
ΔS Deletion of the glycerol-3-phosphate acyltransferase gene (SCT1)
oC Overexpression of the NADPH-cytochrome P450-reductase gene CPR1
oF Overexpression of the (fatty) alcohol oxidase gene FAO1
Explanations on the Sequence Protocol
SEQ ID NO. 1: DNA sequence of the plasmid pJET1.2/blunt (Fermentas).
SEQ ID NO. 2: DNA sequence of the plasmid pUCBM21 (Boehringer Ingelheim).
SEQ ID NO. 3: DNA sequence of the artificial plasmid pUC-Lys2-DK2.
SEQ ID NO. 5: DNA sequence of the artificial plasmid pINTB_HMG1.

Figure 1:
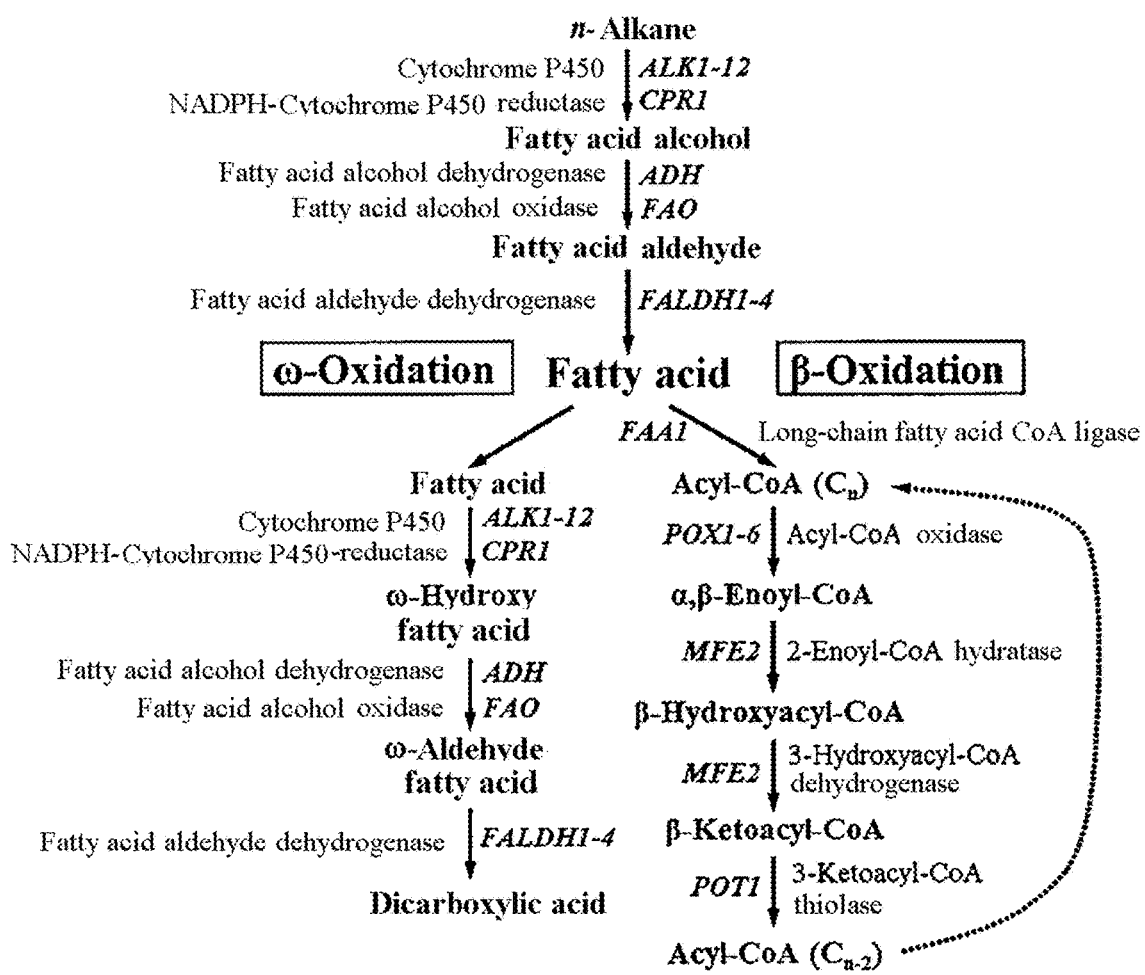
FIG. 1: shows the metabolic paths for the breakdown of hydrophobic substrates by *Y. lipolytica*.

FIG. 1 shows that n-alkanes are assimilated into the cell and are then converted to the corresponding fatty acid with the same chain length in the course of primary alkane oxidation. The fatty acids are then broken down in the course of the β-oxidation to acetyl-CoA (or propionyl-CoA). The diterminal oxidation of fatty acids (ω-oxidation) can take place in parallel. The names of the chemical substances formed are also given as are the designations of the enzymes involved and the corresponding genes. ALK1: YALI0E25982g, ALK2: YALI0F01320g, ALK3: YALI0A20130g, ALK4: YALI0B13816g, ALK5: YALI0B13838g, ALK6: YALI0B01848g, ALK7: YALI0A15488g, ALK8: YALI0C12122g, ALK9: YALI0B06248g, ALK10: YALI0B20702g, ALK11: YALI0C10054g, ALK12: YALI0A20130g, CPR1: YALI0D04422g, FADH: YALI0F09603g, ADH1: YALI0D25630g, ADH2: YALI0E17787g, ADH3: YALI0A16379g, ADH4: YALI0E15818g, ADH5: YALI0D02167g, ADH6: YALI0A15147g, ADH7: YALI0E07766g, ADH8: YALI0C12595g, FAO1:

YALI0B14014g, FALDH1: YALI0A17875g, FALDH2: YALI0E15400g, FALDH3: YALI0B01298g, FALDH4: YALI0F23793g, FAA1: YALI0D17864g, POX1: YALI0E32835g, POX2: YALI0F10857g, POX3: YALI0D24750g, POX4: YALI0E27654g, POX5: YALI0C23859g, POX6: YALI0E06567g, MFE2: YALI0E15378g, POT1: YALI0E18568g.

Figure 2:
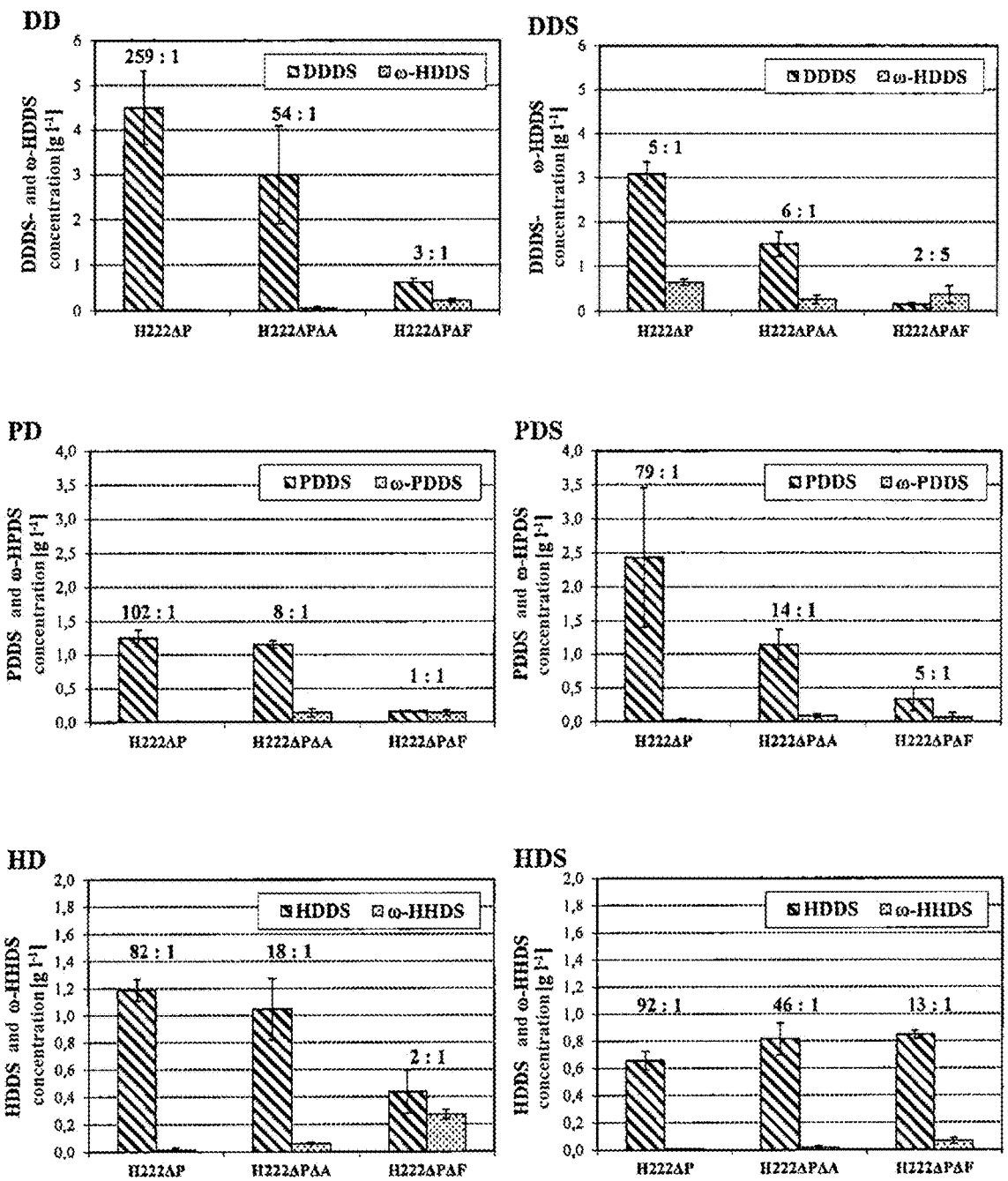
FIG. 2: shows the accumulation of dicarboxylic acids and ω-hydroxy fatty acids in *Y. lipolytica* H222ΔP, H222ΔPΔA and H222ΔPΔF using various hydrophobic substrates.

In FIG. 2 *Y. lipolytica* H222ΔP, H222ΔPΔA and H222ΔPΔF were cultivated in minimal medium with glycerol and various n-alkanes and fatty acids (DD: dodecane; DDS: dodecanoic acid; PD: pentadecane; PDS: pentadecanoic acid; HD: hexadecane; HDS: hexadecanoic acid) in a shaking flask (3% (v/v) glycerol+0.5% (v/v) glycerol after 48 h, 1% (v/v) n-alkane or 1% (v/v) fatty acid, 20 g l$^{-1}$ CaCO$_3$, 17.3 g l$^{-1}$ KH$_2$PO$_4$, 1.35 g l$^{-1}$ K$_2$HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride). The quantities of the dicarboxylic acid and ω-hydroxy fatty acids formed (DDDS: dodecanoic diacid; w-HDDS: ω-hydroxydodecanoic acid; PDDS: pentadecanoic acid; ω-HPDS: ω-hydroxypentadecanoic acid; HDDS: hexadecanoic acid; ω-HHDS: ω-hydroxyhexadecanoic acid) were determined after cultivation for 96 h by means of gas chromatography.

Figure 3:
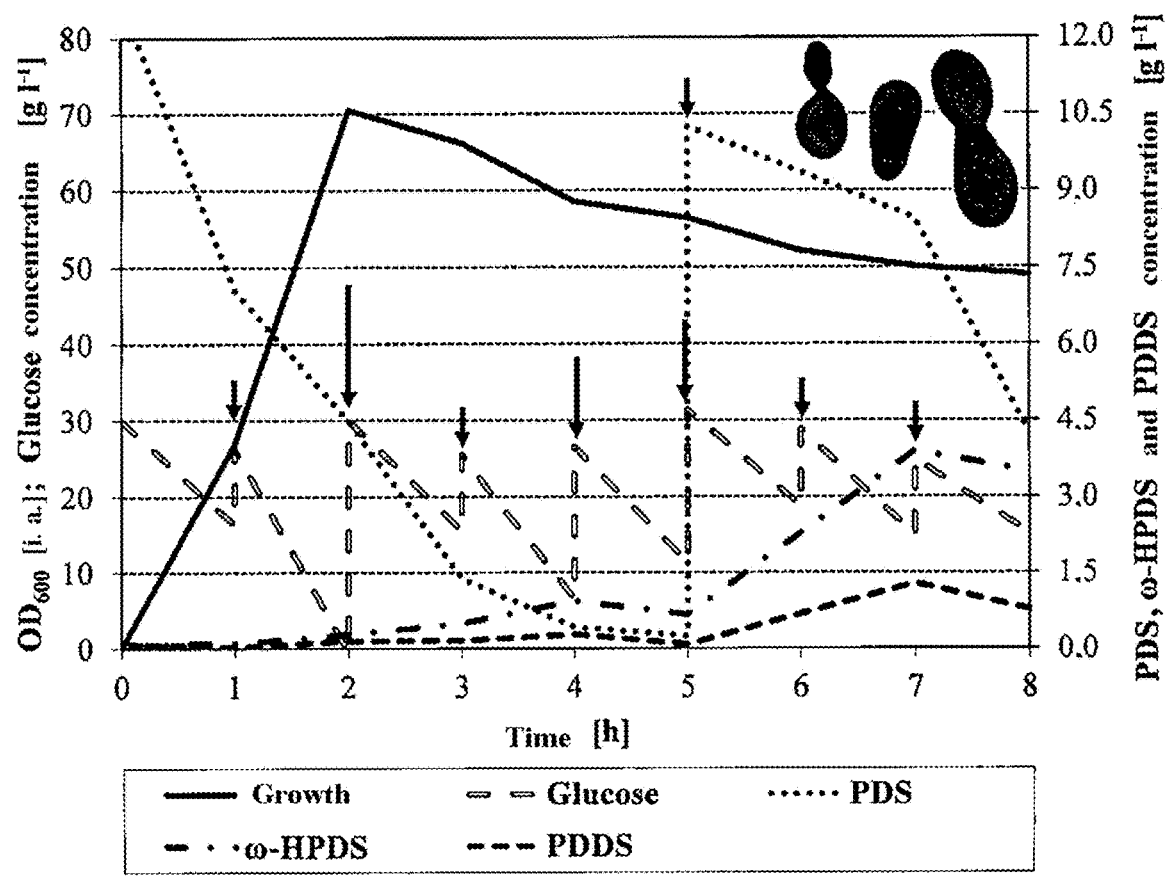
FIG. 3: shows the bioconversion of pentadecanoic acid to ω-hydroxypentadecanoic acid by *Y. lipolytica* H222ΔPΔF.

In FIG. 3 *Y. lipolytica* H222ΔPΔF was cultivated in minimal medium with glucose and pentadecanoic acid (PDS) as carbon sources in a shaking flask (3% (v/v) glucose, 1% (w/v) PDS, 17.3 g l$^{-1}$ KH$_2$PO$_4$, 1.35 g l$^{-1}$ K$_2$HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride). The glucose concentration was held between 2 and 3% (w/v) by regular after-feeding (arrows). After 5 days 1% (w/v) pentadecanoic acid is after-fed. The pentadecanoic acid derivates formed, ω-hydroxypentadecanoic acid (w HPDS) and pentadecanoic acid (PDDS), were quantified by means of gas chromatography. The cells were examined under a microscope towards the end of the cultivation, where the lipid bodies were stained with Nile red.

Figure 4:
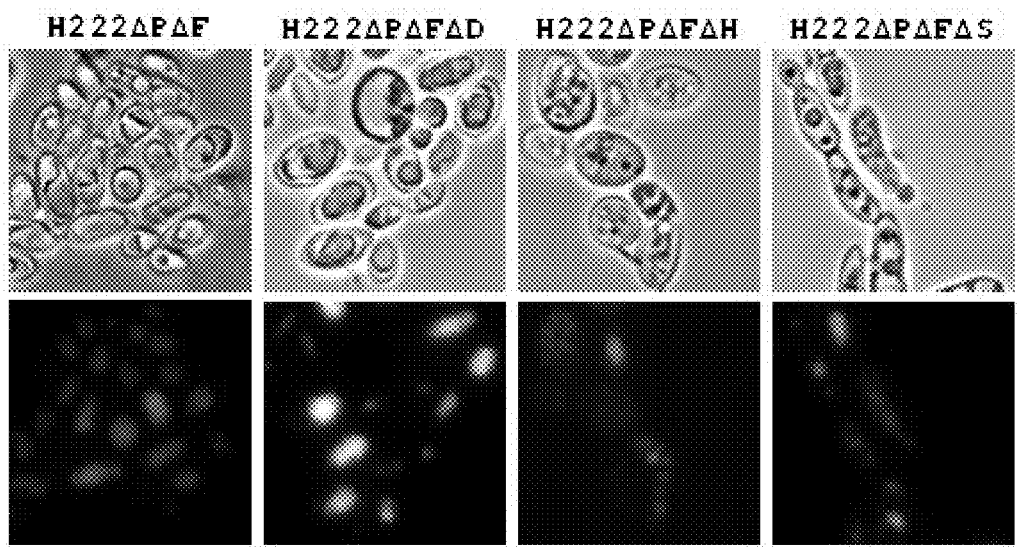
FIG. 4: shows the formation of lipid bodies in *Y. lipolytica* H222ΔPΔF, H222ΔPΔFΔD, H222ΔPΔFΔH and H222ΔPΔFΔS.

FIG. 4 shows the cultivation of *Y. lipolytica* H222ΔPΔF, H222ΔPΔFΔD, H222ΔPΔFΔH and H222ΔPΔFΔS in minimal medium with glucose and pentadecanoic acid (PDS) as carbon sources (3% (v/v) glucose, 1% (w/v) PDS, 17.3 g l$^{-1}$ KH$_2$PO$_4$, 1.35 g l$^{-1}$ K$_2$HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride). The glucose concentration was held between 2 and 3% (w/v) by regular after-feeding. After 3 days 1% (w/v) pentadecanoic acid was after-fed. The cells were examined under a microscope after 5 days, where the lipid bodies were stained with Nile red (top: optical micrograph; bottom: fluorescence micrograph).

In FIG. 5 *Y. lipolytica* H222ΔP, H222ΔPΔA, H222ΔPΔF, H222ΔPΔAΔF, H222ΔPoF, H222ΔPoC, H222ΔPΔFΔС, H222ΔPΔH, H222ΔPΔS, H222ΔPΔAΔFoC, H222ΔPΔAΔFΔD, H222ΔPΔAΔFΔH and H222ΔPΔAΔFΔS was cultivated in a fermenter. The cultivation medium here was minimal medium with glucose (5% (w/v) glucose, 1 g KH$_2$PO$_4$, 0.16 g l$^{-1}$ K$_2$HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride). Cultivation was carried out in a fermenter at 28° C. The oxygen saturation was set at 55%. The cells were inoculated with an OD$_{600}$ of 1 and incubated for 24 h at pH 5.5 (automated titration of HCl and NaOH). Then 15 g l$^{-1}$ DD was added and the pH was set to 8.0. Glucose was added every 24 h to adjust a final concentration of 5% (w/v). The quantities of dodecanoic acid (DDDS) and ω-hydroxydodecanoic acid formed (w-HDDS) were determined after cultivation for 2 d, 3 d and 4 d by means of gas chromatography.

FIG. 6 shows the enzyme activities of the (fatty) alcohol dehydrogenases and oxidase in cell lysates of the strains *Yarrowia lipolytica* H222ΔP, H222ΔPΔA, H222ΔPΔF, H222ΔPΔAΔF and H222ΔPoF. The cells were cultivated as described in Example 8 and harvested and macerated after three days.

Figure 7:
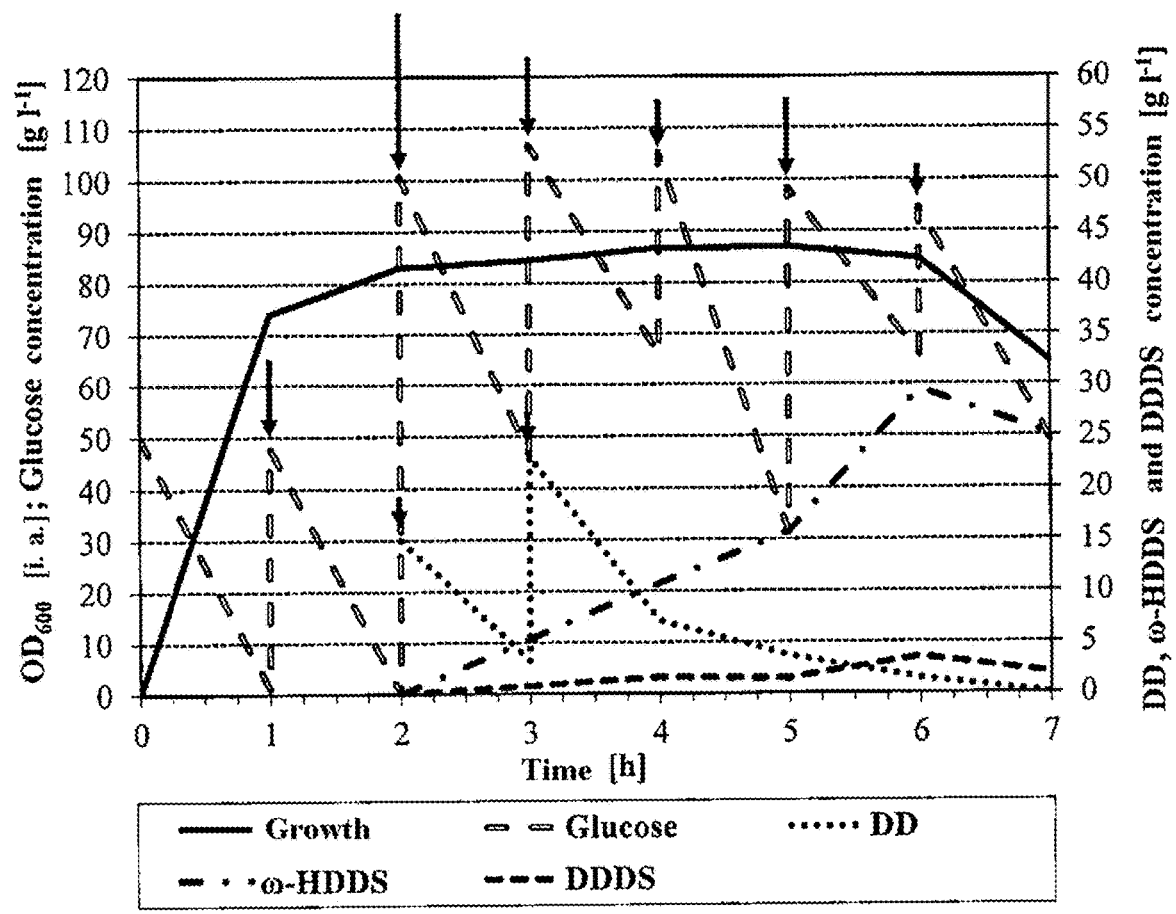
FIG. 7: shows the bioconversion of dodecane to ω-hydroxydodecanoic acid dodecanoic diacid by *Y. lipolytica* H222ΔPΔF.

In FIG. 7 *Y. lipolytica* H222ΔPΔF was cultivated in minimal medium with glucose and dodecane (DD) as carbon sources in a fermenter (5% (w/v) glucose, 2 g l$^{-1}$ KH$_2$PO$_4$, 0.32 g l$^{-1}$ K$_2$HPO$_4$×3 H$_2$O, 6 g l$^{-1}$ (NH$_4$)$_2$SO$_4$, 1.4 g l$^{-1}$ MgSO$_4$×7 H$_2$O, 1 g l$^{-1}$ NaCl, 0.8 g l$^{-1}$ Ca(NO$_3$)$_2$×4 H$_2$O, 1 mg l$^{-1}$ H$_3$BO$_3$, 0.08 mg l$^{-1}$ CuSO$_4$×5 H$_2$O, 0.2 mg l$^{-1}$ KI, 0.8 mg l$^{-1}$ MnSO$_4$×4 H$_2$O, 0.4 mg l$^{-1}$ Na$_2$MoO$_4$×2 H$_2$O, 0.8 mg l$^{-1}$ ZnSO$_4$×7 H$_2$O, 12 mg l$^{-1}$ FeCl$_3$×6 H$_2$O, 0.6 mg l$^{-1}$ thiamine hydrochloride). The glucose was adjusted to 5-10% (w/v) every 24 h by regular after-feeding (arrows). After 2 d the pH was set to 8.0 and 15 g l$^{-1}$ of dodecane was added after 2 d and 3 d. Glucose was added every 24 h in order to adjust a final concentration of 5-10% (w/v).

DETAILED DESCRIPTION OF THE PREFERRED EMBODIMENTS

Example 1

Prevention of the Breakdown of Fatty Acids by Blocking of β-Oxidation

For construction of the deletion cassettes for the POX genes, the respective promoter and terminator region was amplified by PCR, where the primers pXXX_fw/pXXX_rv and XXXt_fw/XXXt_rv were used (XXX stands for the gene to be deleted). Genomic DNA of *Y. lipolytica* H222 was used as template here.

By using overhang primers, an I-SceI-restriction interface was inserted at the end of the promoter and at the beginning of the terminator region. Promoter and terminator fragment were fused together by overlap-PCR with the primers pXXX_fw and XXXt_rv. The overlap fragment was then ligated into the vector pJET1.2/blunt (Fermentas; SEQ ID NO 1). The resulting plasmid was cut with I-SceI and the loxP-URA3-loxP cassette, which was obtained from the pJMP113 plasmid (Fickers P, Le Dall M T, Gaillardin C, Thonart P & Nicaud J M (2003) New disruption cassettes for rapid gene disruption and marker rescue in the yeast *Yarrowia lipolytica*. J Microbiol Methods 55: 727-737) using the restriction enzyme I-SceI was inserted.

The respective deletion cassette was obtained by PCR or restriction and transformed in *Y. lipolytica* H222-S4, which can be produced from *Y. lipolytica* H222 (Mauersberger, S., H. J. Wang, et al. (2001), J Bacteriol 183(17): 5102-5109), according to Barth and Gaillardin (Barth G & Gaillardin C (1996) *Yarrowia lipolytica*. Springer-Verlag, Berlin, Heidelberg, New York).

Before a renewed transformation, the marker was recovered with the aid of the Cre-lox recombination systems (Fickers P, Le Dall M T, Gaillardin C, Thonart P & Nicaud J M (2003) New disruption cassettes for rapid gene disruption and marker rescue in the yeast *Yarrowia lipolytica*. J Microbiol Methods 55: 727-737).

The successful deletion of a gene was confirmed by PCR where the primers pXXX_fw and XXXt_rv as well as pXXX_fw and XXXt_rv2. XXXt_rv2 binds in the region of the gene to be deleted but outside the deletion cassette.

The strain which carried the deletions of the genes POX1, POX2, POX3, POX4, POX5 and POX6 was called H222ΔP and forms the basis for the construction of strains which can be used for the biotechnological production of ω-hydroxy fatty acids and dicarboxylic acids.

Example 2

Prevention of the Oxidation of ω-Hydroxy Fatty Acids to Fatty Acid Aldehyde or to Dicarboxylic Acid in the Course of ω-Oxidation For construction of the deletion cassettes for the (fatty) alcohol dehydrogenase and oxidase genes, the respective promoter and terminator region was amplified by PCR, where the primers pXXX_fw/pXXX_rv and XXXt_fw/XXXt_rv were used (XXX stands for the gene to be deleted). Genomic DNA of *Y. lipolytica* H222 was used as template here.

For the construction of the deletion cassettes for the genes ADH1-ADH6 and FAO1 a BamHI restriction interface was inserted by using overhang primers at the end of the promoter and at the beginning of the terminator region. In addition, an HindIII-restriction interface was attached at the beginning of the promoter region and an NdeI-restriction interface was attached at the end of the terminator region (ADH1: NotI, FAO1: EcoRI). The fragments were ligated into the vector pJET1.2/blunt (Fermentas; SEQ ID NO 1) or

TABLE 1 on the recovery and detection of POX deletion cassettes

| Name | SEQ ID | Sequence (5'→3') | RS |
| --- | --- | --- | --- |
| pPOX1_fw | SEQ ID NO 7 | TCCAGAAGCGCTACAAAGAG | |
| pPOX1_rv | SEQ ID NO 8 | attaccctattatccctaTGAAGGTTGCAGTCGTAGTC | I-SceI |
| POX1t_fw | SEQ ID NO 9 | tagggataacagggtaatTGCGATCTCGATGAGTGATG | I-SceI |
| POX1t_rv | SEQ ID NO 10 | GCCCAGAAGATTGGAATGAC | |
| pPOX2_fw | SEQ ID NO 11 | atataccgcggGATTCCGCCAAGTGAGACTG | Cfr42I |
| pPOX2_rv | SEQ ID NO 12 | attaccctgttatccctaCGTCGAGGAAGTAGGICATC | I-SceI |
| POX2t_fw | SEQ ID NO 13 | tagggataacagggtaatGCGAGCTTGATGAGGAATAG | I-SceI |
| POX2t_rv | SEQ ID NO 14 | atataccgcggCCTGACGCCAATTTGAAGAG | Cfr42I |
| pPOX3_fw | SEQ ID NO 15 | atataccgcggCTGGGCTGTTCGGTCGATAG | Cfr42I |
| pPOX3_rv | SEQ ID NO 16 | tagggataacagggtaatAGGACGCACAACGCCATCAC | I-SceI |
| POX3t_fw | SEQ ID NO 17 | attaccctgttatccctaCGCTCCCATTGGAAACTA | I-SceI |
| POX3t_rv | SEQ ID NO 18 | atataccgcggTCTCTTCGCTGTGGTCTAGG | Cfr42I |
| pPOX4_fw | SEQ ID NO 19 | atataccgcggTCCACCGTTCTCCTTCATAC | Cfr42I |
| pPOX4_rv | SEQ ID NO 20 | tagggataacagggtaatATGTCTCTAGGGTCGAAGTC | I-SceI |
| POX4t_fw | SEQ ID NO 21 | attaccctattatccctaTGGCAAGCCTCACTACTACG | I-SceI |
| POX4t_rv | SEQ ID NO 22 | atataccgcggTGCGGCGGAACTACTGTATC | Cfr42I |
| pPOX5_fw | SEQ ID NO 23 | atataccgcggGGGATTCTCCGGGTTATTTG | Cfr42I |
| pPOX5_rv | SEQ ID NO 24 | tagggataacagggtaatACGTCTCGGACCTTGAATTG | I-SceI |
| POX5t_fw | SEQ ID NO 25 | attaccctgttatccctaCCTTCAACCTGTCCGACTTC | I-SceI |
| POX5t_rv | SEQ ID NO 26 | atataccgcggGAAGCGGTCCTCGTTGTATG | Cfr42I |
| pPOX6_fw | SEQ ID NO 27 | GTGTAGCAACTCGGATACAG | |
| pPOX6_rv | SEQ ID NO 28 | tagggataacagggtaatGGTCCATAAGCAGAGTGTTC | I-SceI |
| POX6t_fw | SEQ ID NO 29 | attaccctgttatccctaACCCTCGACCTCCTTATTAC | I-SceI |
| POX6t_rv | SEQ ID NO 30 | CTCTTCTTGACTGGCATAGC | | pUCBM21 (Boehringer Ingelheim; SEQ ID NO 2). The plasmids thus obtained were linearized with BamHI and the URA blaster (TcR-URA3-TcR-Kassette), which was obtained from the plasmid pUC-Lys2-DK2 (SEQ ID NO 3) by restriction with BamHI and BglII, was inserted.

For the construction of the ADH7 deletion vector, the complete gene (including promoter and terminator region) was amplified by means of PCR, where the primers pADH7_fw and ADH7t rv were used. The fragment obtained was ligated into the vector pJET1.2/blunt (Fermentas; SEQ ID NO 1), the open reading frame of the ADH7 gene was removed by restriction with SanDI and NsiI and the URA blaster, which was obtained from the plasmid pUC-Lys2-DK2 by restriction with SanDI and NsiI, was inserted.

The respective deletion cassette was obtained by PCR or restriction and transformed in *Y. lipolytica* H222-S4, which can be produced from *Y. lipolytica* H222 (Mauersberger, S., H. J. Wang, et al. (2001), J Bacteriol 183(17): 5102-5109), according to Barth and Gaillardin (Barth G & Gaillardin C (1996) *Yarrowia lipolytica*. Springer-Verlag, Berlin, Heidelberg, New York).

Before a renewed transformation, the marker was recovered by FOA selection (Boeke J D, La-Croute F & Fink G R (1984) Mol Gen Genet 197: 345-346).

The successful deletion of a gene was confirmed by PCR, where the primers pXXX_fw and XXXt_rv as well as pXXX_fw and XXXt_rv2 were used. XXXt_rv2 binds in the region of the gene to be deleted but outside the deletion cassette.

The strain which carried both the deletions of the genes POX1, POX2, POX3, POX4, POX5 and POX6 and also FADH, AHD1, AHD2, AHD3, AHD4, AHD5, AHD6 and AHD7 was called H222ΔPΔA.

The strain which carried both the deletions of the genes POX1, POX2, POX3, POX4, POX5 and POX6 and also FAO1 was called H222ΔPΔF.

TABLE 2 on the recovery and detection of (F)ADH- and FAO deletion cassettes

| Name | SEQ ID | Sequence (5'→3') | RS |
|---|---|---|---|
| pFADH_fw | SEQ ID NO 31 | atataaagctTGCGGCTCGGCACGTGATCTG | HindIII |
| pFADH_rv | SEQ ID NO 32 | atataggatccATCGTGCGTACGTCGCTAGTG | BamHI |
| FADHt_fw | SEQ ID NO 33 | atataggatccCGACCGGCACGATCAATTGG | BamHI |
| FADHt_rv | SEQ ID NO 34 | atatacatatgGGTGCATCTCAGCCCGACCTC | NdeI |
| FADHt_rv2 | SEQ ID NO 35 | TCCCGAAACACAGAACTTCC | |
| pADH1_fw | SEQ ID NO 36 | atataaagctTGGTGGACGTTCCGGCAGACAG | HindIII |
| pADH1_rv | SEQ ID NO 37 | atataggatccCTCCCAGGCATCTCCACACTC | BamHI |
| ADH1t_fw | SEQ ID NO 38 | atataggatccCACTTACAGGCTTAGCAAGG | BamHI |
| ADH1t_rv | SEQ ID NO 39 | atatagcggccgcGGAAATCACGCTTGATTCG | NotI |
| ADH1t_rv2 | SEQ ID NO 40 | TAGGCGCTGGTACAGAAGAG | |
| pADH2_fw | SEQ ID NO 41 | atataaagctTGAGTACAGTAGGTGGTACTC | HindIII |
| pADH2_rv | SEQ ID NO 42 | atataggatccAGTGGTGGTGGTGGTGGTAG | BamHI |
| ADH2t_fw | SEQ ID NO 43 | atataggatccTTTACGTGCAACAGGAGGAG | BamHI |
| ADH2t_rv | SEQ ID NO 44 | atatacatatgGCCTGTCTTGAGTTCTTTGG | NdeI |
| ADH2t_rv2 | SEQ ID NO 45 | AGGGTCGTAGATAACGAGTC | |
| pADH3_fw | SEQ ID NO 46 | atataaagctTCACGTGGCTGCTGGGCCAACC | HindIII |
| pADH3_rv | SEQ ID NO 47 | atataggatccCGCACGGTATCGGAGCATCG | BamHI |
| ADH3t_fw | SEQ ID NO 48 | atataggatccCGCGGCTATTGACGCTGAGG | BamHI |
| ADH3t_rv | SEQ ID NO 49 | atatacatatgCCCGTCAGCTCCATCGACGAGTG | NdeI |
| ADH3t_rv2 | SEQ ID NO 50 | AGGTGTACTGTAGCCACCCTGAC | |
| pADH4_fw | SEQ ID NO 51 | atataaagctTCCGGCCAGCCGCTGGCAACG | HindIII |
| pADH4_rv | SEQ ID NO 52 | atataggatccACACGACAGCTGCACCTGAC | BamHI |
| ADH4t_fw | SEQ ID NO 53 | atataggatccCAGCCATGAGCCAGGCATTG | BamHI |
| ADH4t_rv | SEQ ID NO 54 | atatacatatgGGCGCCAGCCACATTTGCCCTC | NdeI |
| ADH4t_rv2 | SEQ ID NO 55 | AGCGATACAGCAGTTGACTC | |
| pADH5_fw | SEQ ID NO 56 | TCAGCCGTCTACTTGTAGAG | |

TABLE 2-continued on the recovery and detection of (F)ADH- and FAO deletion cassettes

| Name | SEQ ID | Sequence (5'→3') | RS |
|---|---|---|---|
| pADH5_rv | SEQ ID NO 57 | atataggatccGTGGCTCGGATACTCCTGAC | BamHI |
| ADH5t_fw | SEQ ID NO 58 | atataggatccAGCCGGAGGTCAGATCAAGC | BamHI |
| ADH5t_rv | SEQ ID NO 59 | atatacatatgGCGCAATAGTTCGCCGGCCTG | NdeI |
| ADH5t_rv2 | SEQ ID NO 60 | CTCGTGTTGTGCCTTTCTTG | |
| pADH6_fw | SEQ ID NO 61 | atataaagctTGCGCGACAACCCATAGCGATGGC | HindIII |
| pADH6_rv | SEQ ID NO 62 | atataggatccGATAAGAGGGCGCTCTGACC | BamHI |
| ADH6t_fw | SEQ ID NO 63 | atataggatccGGCGTGACATCGAGTTTGG | BamHI |
| ADH6t_rv | SEQ ID NO 64 | atatacatatgCTACGTCTCGCCGCAGAGGG | NdeI |
| ADH6t_rv2 | SEQ ID NO 65 | AGCGAGAGGTTATACGGAAG | |
| pADH7_fw | SEQ ID NO 66 | CTCCTACAGCCTCTCAAGAC | |
| ADH7t_rv | SEQ ID NO 67 | GTCTACAAGACAGCCCAGAG | |
| pADH7_fw2 | SEQ ID NO 68 | CCGCTTGAGAAGAGCAATAC | |
| pFAO1_fw | SEQ ID NO 69 | atataaagctTCGCCACCTGTCCACGTCTCG | HindIII |
| pFAO1_rv | SEQ ID NO 70 | atataggatccGCGAAGCGACGTGTGGTGAG | BamHI |
| FAO1t_fw | SEQ ID NO 71 | atataggatccGCTGAGCACGCGAGTACACC | BamHI |
| FAO1t_rv | SEQ ID NO 72 | atatagaattcGATCTGTCGTACAACTAAGG | EcoRI |
| FAO1t_rv2 | SEQ ID NO 73 | CAGAAGTTACGACGCCAAGG | |

Example 3

Comparative Cultivation of Various Production Strains in a Shaking Flask

In order to check whether the initial strains produced Yarrowia lipolytica H222ΔP, H222ΔPΔA and H222ΔPΔF are suitable for the production of larger quantities of ω-hydroxy fatty acids and dicarboxylic acids, these were cultivated in minimal medium with glycerol and various n-alkanes (dodecane, pentadecane, hexadecane) and fatty acids (dodecanoic acid, pentadecanoic acid, hexadecanoic acid) (3% (v/v) glycerol+0.5% (v/v) glycerol after 48 h, 1% (v/v) n-alkane or 1% (v/v) fatty acid, 20 g l$^{-1}$ CaCO$_3$, 17.3 g l$^{-1}$ KH$_2$PO$_4$, 1.35 g l$^{-1}$ K$_2$HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride). The quantities of ω-hydroxy fatty acids (ω-hydroxydodecanoic acid, ω-hydroxypentadecanoic acid, ω-hydroxyhexadecanoic acid) and dicarboxylic acids formed (dodecanoic diacid, pentadecanoic diacid, hexadecanoic diacid) were determined by means of gas chromatography 96 h after cultivation (FIG. 2A-F).

Y. lipolytica H222ΔP here formed relatively large quantities of dicarboxylic acids and can thus be used as initial strain for the construction of a corresponding production strain for dicarboxylic acids.

Both Y. lipolytica H222ΔPΔA and also H222ΔPΔF formed increased quantities of ω-hydroxy fatty acids and can thus be used as initial strains for the construction of corresponding production strains for ω-hydroxy fatty acids. Y. lipolytica H222ΔPΔF is to be preferred to H222ΔPΔA here.

Both n-alkanes and also fatty acids can be converted from all strains to ω-hydroxy fatty acid or dicarboxylic acid having the same chain length.

Example 4

Use of Different Cultivation Conditions and Media

Different strains (e.g. Yarrowia lipolytica H222ΔP and H222ΔPΔF) were cultivated in different media under various conditions, where it was found that the media and conditions used are variously well suited.

The yeasts were cultivated comparatively in minimal medium with glucose (3% (w/v) glucose, 1% (w/v) pentadecanoic acid, 17.3 g l$^{-1}$ KH$_2$PO$_4$, 1.35 g l$^{-1}$ K$_2$HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride) and glycerol (3% (v/v) glycerol, 1% (w/v) pentadecanoic acid, 17.3 g l$^{-1}$ KH$_2$PO$_4$, 1.35 g l$^{-1}$ K2HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride) as carbon source, where after 48 h 1% (w/v) glucose, or 1% (v/v) glycerol were after-fed. After 96 h, all the strains studied (e.g. Y. lipolytica H222ΔP, H222ΔPΔA and H222ΔPΔF) formed larger quantities of ω-hydroxy fatty acid or pentadecanoic diacid for growth in minimal medium with glucose than for growth in minimal medium with glycerol.

The yeasts were then cultivated in full medium with glucose and pentadecanoic acid (1% (w/v) yeast extract, 2% (w/v) peptone, 2% (w/v) glucose and 1% (w/v) pentadecanoic acid in 1% Tween 80), where 1% (w/v) glucose was after-fed when this was used up. After 4 days, 1% (w/v) of pentadecanoic acid in 1% Tween 80 was after-fed. Under these conditions, almost no ω-hydroxy pentadecanoic acid or pentadecanoic diacid was formed (each<0.1 g $l^{-1}$).

The yeasts were cultivated in minimal medium with glucose and pentadecanoic acid (3% (v/v) glucose, 1% (w/v) pentadecanoic acid in 1 Tween 80, 17.3 g $l^{-1}$ KH$_2$PO$_4$, 1.35 g $l^{-1}$K$_2$HPO$_4$×3 H$_2$O, 3 g $l^{-1}$ (NH$_4$)$_2$SO$_4$, 0.7 g $l^{-1}$ MgSO$_4$×7 H$_2$O, 0.5 g $l^{-1}$ NaCl, 0.4 g $l^{-1}$ Ca(NO$_3$)$_2$×4 H$_2$O, 0.5 mg $l^{-1}$ H$_3$BO$_3$, 0.04 mg $l^{-1}$ CuSO$_4$×5 H$_2$O, 0.1 mg $l^{-1}$ KI, 0.4 mg $l^{-1}$ MnSO$_4$×4 H$_2$O, 0.2 mg $l^{-1}$ Na$_2$MoO$_4$×2 H$_2$O, 0.4 mg $l^{-1}$ ZnSO$_4$×7 H$_2$O, 6 mg $l^{-1}$ FeCl$_3$×6 H$_2$O, 0.3 mg $l^{-1}$ thiamine hydrochloride), where 1% (w/v) glucose was after-fed when this was used up. After 4 days, 1% (w/v) pentadecanoic acid in 1% Tween 80 was after-fed. Under these cultivation conditions, the strain *Y. lipolytica* H222ΔPΔF after 10 days formed around 0.7 g $l^{-1}$ω-hydroxy pentadecanoic acid and 2.4 g $l^{-1}$ pentadecanoic diacid.

The yeasts were cultivated in minimal medium with glucose and pentadecanoic acid (3% (v/v) glucose, 1% (w/v) pentadecanoic acid in 1 Tween 80, 17.3 g $l^{-1}$ KH$_2$PO$_4$, 1.35 g $l^{-1}$K$_2$HPO$_4$×3 H$_2$O, 3 g $l^{-1}$ (NH$_4$)$_2$SO$_4$, 0.7 g $l^{-1}$ MgSO$_4$×7 H$_2$O, 0.5 g $l^{-1}$ NaCl, 0.4 g $l^{-1}$ Ca(NO$_3$)$_2$×4 H$_2$O, 0.5 mg $l^{-1}$ H$_3$BO$_3$, 0.04 mg $l^{-1}$ CuSO$_4$×5 H$_2$O, 0.1 mg $l^{-1}$ KI, 0.4 mg $l^{-1}$ MnSO$_4$×4 H$_2$O, 0.2 mg $l^{-1}$ Na$_2$MoO$_4$×2 H$_2$O, 0.4 mg $l^{-1}$ ZnSO$_4$×7 H$_2$O, 6 mg $l^{-1}$ FeCl$_3$×6 H$_2$O, 0.3 mg $l^{-1}$ thiamine hydrochloride), where the glucose was after-fed so that its concentration in the medium was between 1 and 3% (w/v). After 5 days 1% (w/v) pentadecanoic acid in 1% Tween 80 was after-fed. Under these cultivation conditions the strain *Y. lipolytica* H222ΔPΔF after 7 days formed around 3.9 g $l^{-1}$ ω-hydroxy pentadecanoic acid and 1.3 g $l^{-1}$ pentadecanoic diacid.

To sum up, it should be noted that minimal medium is better suited for the cultivation than full medium. Furthermore, glucose is more suitable than glycerol as carbon source for the energy preparation. The glucose should be after-fed in the course of the cultivation so that the glucose is not used up (i.e. its concentration does not drop to 0 g $l^{-1}$).

Example 5

Reduction in the Formation of Lipid Bodies

For construction of the deletion cassettes for the genes DGA1, PAH1 and SCT1 the respective promoter and terminator region was amplified by PCR where the primers pXXX_fw/pXXX_rv and XXXt_fw/XXXt_rv were used (XXX stands for the gene to be deleted). Genomic DNA of *Y. lipolytica* H222 was used as template here.

For the construction of deletion cassettes for the genes DGA1, PAH1 and SCT1 a BamHI-restriction interface was inserted by using overhang primers at the end of the promoter region and at the beginning of the terminator region. In addition a HindIII-restriction interface was attached at the beginning of the promoter region and an EcoRI-restriction interface was attached at the end of the terminator region. The fragments were ligated into the vector pUCBM21 (Boehringer Ingelheim; SEQ ID NO 2). The plasmids thus obtained were linearized with BamHI and the URA blaster (TcR-URA3-TcR-cassette), which was obtained from the plasmid pUC-Lys2-DK2 (SEQ ID NO 3) by restriction with BamHI and BglII was inserted. The respective deletion cassette was obtained by PCR or restriction and transformed in *Y. lipolytica* H222-S4, which can be produced from *Y. lipolytica* H222 (Mauersberger, S., H. J. Wang, et al. (2001), J Bacteriol 183(17): 5102-5109), according to Barth and Gaillardin (Barth G & Gaillardin C (1996) *Yarrowia lipolytica*. Springer-Verlag, Berlin, Heidelberg, New York).

Before a renewed transformation, the marker was recovered by FOA selection (Boeke J D, La-Croute F & Fink G R (1984) Mol Gen Genet 197: 345-346).

The successful deletion of a gene was confirmed by PCR, where the primers pXXX_fw and XXXt_rv as well as pXXX_fw and XXXt_rv2 were used. XXXt_rv2 binds in the region of the gene to be deleted but outside the deletion cassette.

The strain which carried both the deletions of the genes POX1, POX2, POX3, POX4, POX5 and POX6 and also DGA1 was called H222ΔPΔD.

The strain which carried both the deletions of the genes POX1, POX2, POX3, POX4, POX5 and POX6 and also PAH1 was called H222ΔPΔH.

The strain which carried both the deletions of the genes POX1, POX2, POX3, POX4, POX5 and POX6 and also SCT1 was called H222ΔPΔS.

The strain which carried both the deletions of the genes POX1, POX2, POX3, POX4, POX5 and POX6 and also FAO1 and DGA1 was called H222ΔPΔFΔD.

The strain which carried both the deletions of the genes POX1, POX2, POX3, POX4, POX5 and POX6 and also FAO1 and PAH1 was called H222ΔPΔFΔH.

The strain which carried both the deletions of the genes POX1, POX2, POX3, POX4, POX5 and POX6 and also FAO1 and SCT1 was called H222ΔPΔFΔS.

The strain which carried both the deletions of the genes POX1, POX2, POX3, POX4, POX5 and POX6 and also FADH, ADH1, ADH2, ADH3, ADH4, ADH5, ADH6, ADH7, FAO1 and DGA1 was called H222ΔPΔAΔFΔD.

The strain which carried both the deletions of the genes POX1, POX2, POX3, POX4, POX5 and POX6 and also FADH, ADH1, ADH2, ADH3, ADH4, ADH5, ADH6, ADH7, FAO1 and PAH1 was called H222ΔPΔAΔFΔH.

The strain which carried both the deletions of the genes POX1, POX2, POX3, POX4, POX5 and POX6 and also FADH, ADH1, ADH2, ADH3, ADH4, ADH5, ADH6, ADH7, FAO1 and SCT1 was called H222ΔPΔAΔFΔS.

TABLE 3

Primers for recovery and detection of DGA1-, PAH1- and SCT1-deletion cassettes

| Name | SEQ ID | Sequence (5'→3') | RS |
|---|---|---|---|
| pDGA1_fw | SEQ ID NO 74 | atataaagcttCCGTAA- | HindIII |
| pDGA1_rv | SEQ ID NO 75 | atataggatccAGGTCGAT- | BamHI |

TABLE 3-continued

Primers for recovery and detection of DGA1-, PAH1- and SCT1-deletion cassettes

| Name | SEQ ID | Sequence (5'→3') | RS |
|---|---|---|---|
| DGA1t_fw | SEQ ID NO 76 | atataggatccGGTTAGGCAAA- | BamHI |
| DGA1t_rv | SEQ ID NO 77 | atatagaattcGCCTGGAGCGAG- | EcoRI |
| DGA1t_rv2 | SEQ ID NO 78 | TCGCAAGGGCCATAGAGGTG | |
| pPAH1_fw | SEQ ID NO 79 | atataaagcttCCTT- | HindIII |
| pPAH1_rv | SEQ ID NO 80 | atataggatccGGTGTTACGCCACCAC- | BamHI |
| PAH1t_fw | SEQ ID NO 81 | atataggatccGGGACCTGCGATAC- | BamHI |
| PAH1t_rv | SEQ ID NO 82 | atatagaattcGCTTGCGCAGCCGGTG- | EcoRI |
| PAH1t_rv2 | SEQ ID NO 83 | GGCGTTGTGGAGCTATCACC | |
| pSCT1_fw | SEQ ID NO 84 | atataaagcttGCGTGCGGTGCGTGCG- | HindIII |
| pSCT1_rv | SEQ ID NO 85 | atataggatccCAGCACCAC- | BamHI |
| SCT1t_fw | SEQ ID NO 86 | atataggatccGTGCGCTTACATGTG- | BamHI |
| SCT1t_rv | SEQ ID NO 87 | atatagaattcCAGGCAGCTTCTT- | EcoRI |
| SCT1t_rv2 | SEQ ID NO 88 | GAGATAGGAGGTTCCCATAC | |

The strains Y. lipolytica H222ΔPΔFΔD, H222ΔPΔFΔH and H222ΔPΔFΔS as well as the initial strain Y. lipolytica H222ΔPΔF were cultivated in minimal medium with glucose and pentadecanoic acid (3% (v/v) glucose, 1% (w/v) pentadecanoic acid, 17.3 g $l^{-1}$ $KH_2PO_4$, 1.35 g $l^{-1}$ $K_2HPO_4 \times 3$ $H_2O$, 3 g $l^{-1}$ $(NH_4)_2SO_4$, 0.7 g $l^{-1}$ $MgSO_4 \times 7$ $H_2O$, 0.5 g $l^{-1}$ NaCl, 0.4 g $l^{-1}$ $Ca(NO_3)_2 \times 4$ $H_2O$, 0.5 mg $l^{-1}$ $H_3BO_3$, 0.04 mg $l^{-1}$ $CuSO_4 \times 5$ $H_2O$, 0.1 mg $l^{-1}$ KI, 0.4 mg $l^{-1}$ $MnSO_4 \times 4$ $H_2O$, 0.2 mg $l^{-1}$ $Na_2MoO_4 \times 2$ $H_2O$, 0.4 mg $l^{-1}$ $ZnSO_4 \times 7$ $H_2O$, 6 mg $l^{-1}$ $FeCl_3 \times 6$ $H_2O$, 0.3 mg $l^{-1}$ thiamine hydrochloride). Every 24 h the glucose concentration was adjusted to 3% (w/v) and after 3 days 1% (w/v) of pentadecanoic acid was after-fed. The quantities of ω-hydroxy fatty acid and pentadecanoic acid were determined after cultivation for 8 days by means of gas chromatography. The cells were examined under the microscope, where the lipid bodies were stained with Nile red and could thus be detected by fluorescence microscopy (FIG. 4).

Here it can be identified that the size of the lipid bodies was significantly reduced due to deletions of PAH1 and SCT1 under the said cultivation conditions. As already shown, this could not be determined for the already described deletion of DGA1 (Thevenieau F (2006) Institut National Agronomique Paris-Grignon, PhD thesis; Athenstaedt K (2011) Biochim Biophys Acta 1811: 587-596).

The availability of strains with reduced lipid bodies forms the basis for the development of strains for the efficient production of ω-hydroxy fatty acids and dicarboxylic acids since the esterification of the supplied substrates with glycerol and its incorporation into the lipid bodies reduces the conversion rate.

Example 6

Increased Expression of FAO1 in Yarrowia lipolytica H222ΔP

For construction of a vector for overexpression of FAO1 a part of the constitutive promoter of the translation elongation factor 1 alpha-gene (TEF1: YALI0C09141g) was obtained by means of PCR, where the primers pTef_SpeI_fw3 and pTef_FAOo_ol_rv were used. The plasmid pINTB_HMG1 (SEQ ID NO 5) was used as template here.

Furthermore, the FAO1-gene (YALI0B14014g) was amplified by means of PCR using the primers pTef_FAOo_ol_fw and FAO1o_SphI_rv (template: genomic DNA of Y. lipolytica H222).

By means of the primers pTef_FAOo_ol_rv and pTef_FAOo_ol_fw an overhang region was attached, with the aid of which both PCR fragments were linked by means of overlap PCR using the primers pTef_SpeI_fw3 and FAO1o_SphI_rv. The overlap fragment was then ligated into the vector pJET1.2/blunt (Fermentas; SEQ ID NO 1), cut out from this using the restriction enzymes SpeI and SphI and ultimately ligated into the backbone of the plasmid pINTB_HMG1 (SEQ ID NO 5) cut with SpeI and SphI, where the plasmid pINTB-FAO1 was formed.

Furthermore, an integration platform was obtained by means of PCT using the primers INT_AscI_fw KpnI and INT_AscI_rv_KpnI, cut with KpnI and ligated into the backbone of the vector pINTB-FAO1 obtained by restriction digestion with KpnI, where the plasmid pINTC-FAO1 was formed.

The plasmid pINTC-FAO1 was ultimately linearized with AscI and transformed into the desired Y. lipolytica recipient strain.

Successful integration of the FAO1 gene was confirmed by PCR, where the primers INT_AscI_fw_out and INT_AscI_rv_out were used which bind in the genomic DNA outside the integrated construct.

The strain which carried both the deletions of the genes POX1, POX2, POX3, POX4, POX5 and POX6 and also the additional copy of FAO1 under control of the TEF1-promoter was called H222ΔPoF and was used as initial strain for construction of further strains for the production of dicarboxylic acids.

TABLE 4

Primers for overexpression of FAO1

| Name | SEQ ID | Sequence (5'→3') | RS |
|---|---|---|---|
| pTef_SpeI_fw3 | SEQ ID NO 89 | CTACGCTTGTTCAGACTTTG | |
| pTef_FAOo1_rv | SEQ ID NO 90 | gtgtgcttgtcgtcagacatTTTGAA TGATTCTTATACTCAGAAGG | |
| pTef_FAOo1_fw | SEQ ID NO 91 | ccttctgagtataagaatcattcaaa ATGTCTGACGACAAGCACAC | |
| FAO1o_SphI_rv | SEQ ID NO 92 | gcatgcTTAGATTCGAGGTCGGAGAT | SphI |
| INT_AscI_fw_KpnI | SEQ ID NO 93 | ggtacCACGCACGGATAGTTTATCCA | KpnI |
| INT_AscI_rv_KpnI | SEQ ID NO 94 | ggtacCCAAAGTCAACTAATGTCAAG TAAAG | KpnI |
| INT_AscI_fw_out | SEQ ID NO 95 | CCTCCAACGTGACTTTC | |
| INT_AscI_rv_out | SEQ ID NO 96 | AGAGACCTCCCACAAAG | |

Example 7

Increased Expression of CPR1 in Yarrowia lipolytica H222ΔP and H222ΔPΔAΔF

For construction of a vector for overexpression of FAO1 a part of the constitutive promoter of the translation elongation factor 1 alpha-gene (TEF1: YALI0C09141g) was obtained by means of PCR, where the primers pTef_SpeI_fw3 and pTEF_CPR1_ol_fw were used. The plasmid pINTB_HMG1 (SEQ ID NO 5) was used as template here.

Furthermore, the CPR1-gene (YALI0D04422g) was amplified by means of PCR using the primers pTEF_CPR1_ol_fw and CPR1_SphI_rv (template: genomic DNA of Y. lipolytica H222).

By means of the primers pTEF_CPR1_ol_rv and pTEF_CPR1_ol_fw an overhang region was attached, with the aid of which both PCR fragments were linked by means of overlap PCR using the primers pTef_SpeI_fw3 and CPR1_SphI_rv. The overlap fragment was then ligated into the vector pJET1.2/blunt (Fermentas; SEQ ID NO 1), cut out from this using the restriction enzymes SpeI and SphI and ultimately ligated into the backbone of the plasmid pINT-B_HMG1 (SEQ ID NO 5) cut with SpeI and SphI, where the plasmid pINTB-CPR1 was formed.

The resulting plasmid was ultimately linearized with NotI and transformed into the desired Y. lipolytica recipient strain.

The successful integration of the CPR1-gene was confirmed by PCR, where the primers INTB_out_fw and INT-B_out_rv were used, which bind in the genomic DNA outside the integrated construct.

The strain which carried both the deletions of the genes POX1, POX2, POX3, POX4, POX5 and POX6 and also the additional copy of CPR1 under control of the TEF1-promoter was called H222ΔPoC and was used as initial strain for construction of further strains for the production of dicarboxylic acids.

The strain which carried both the deletions of the genes POX1, POX2, POX3, POX4, POX5, PPX6, FADH, ADH1, ADH2, ADH3, ADH4, ADH5, ADH6, ADH7, FAO1 and also the additional copy of CPR1 under control of the TEF1-promoter was called H222ΔPΔAΔFoC.

TABLE 5

Primers for overexpression of CPR1

| Name | SEQ ID | Sequence (5'→3') | RS |
|---|---|---|---|
| pTef_SpeI_fw3 | SEQ ID NO 89 | CTACGCTTGTTCAGACTTTG | |
| pTEF_CPR1_ol_rv | SEQ ID NO 97 | AGAGAGTCGAGTAGAGCCATTTT GAATGATTCTTATACTCAGAAGG | |
| pTEF_CPR1_ol_fw | SEQ ID NO 98 | CCTTCTGAGTATAAGAATCATTC AAAATGGCTCTACTCGACTCTCT | |
| CPR1_SphI_rv | SEQ ID NO 99 | atatagcatgcCTACCACACATC TTCCTGGTAGAC | SphI |
| INTB_out_fw | SEQ ID NO 100 | CTCAAGATACGGCATTGG | |
| INTB_out_rv | SEQ ID NO 101 | TCCTTGGCTAGACGAATG | |

Example 8

Comparative Cultivation of Different Production Strains in Fermenter

In order to check how far different genetic modifications affect the production of ω-hydroxy fatty acids and/or dicarboxylic acids, the strains *Yarrowia lipolytica* H222ΔP, H222ΔPΔA, H222ΔPΔF, H222ΔPΔAΔF, H222ΔPoF, H222ΔPoC, H222ΔPΔD, H222ΔPΔH, H222ΔPΔS, H222ΔPΔAΔFoC, H222ΔPΔAΔFΔD, H222ΔPΔAΔFΔH and H222ΔPΔAΔFΔS, whose construction was described in Examples 1, 2, 5, 6 and 7 were cultivated in the fermenter. The cultivation medium in this case was minimal medium with glucose (5% (w/v) glucose, 1 g l$^{-1}$ KH$_2$PO$_4$, 0.16 g l$^{-1}$ K$_2$HPO$_4$×3 H$_2$O, 3 g l$^{-1}$ (NH$_4$)$_2$SO$_4$, 0.7 g l$^{-1}$ MgSO$_4$×7 H$_2$O, 0.5 g l$^{-1}$ NaCl, 0.4 g l$^{-1}$ Ca(NO$_3$)$_2$×4 H$_2$O, 0.5 mg l$^{-1}$ H$_3$BO$_3$, 0.04 mg l$^{-1}$ CuSO$_4$×5 H$_2$O, 0.1 mg l$^{-1}$ KI, 0.4 mg l$^{-1}$ MnSO$_4$×4 H$_2$O, 0.2 mg l$^{-1}$ Na$_2$MoO$_4$×2 H$_2$O, 0.4 mg l$^{-1}$ ZnSO$_4$×7 H$_2$O, 6 mg l$^{-1}$ FeCl$_3$×6 H$_2$O, 0.3 mg l$^{-1}$ thiamine hydrochloride). Cultivation was carried out in the fermenter at 28° C. The oxygen saturation was set at 55%. The cells were inoculated with an OD$_{600}$ of 1 and incubated for 24 h at pH 5.5 (automated titration of HCl and NaOH). Then 15 g l$^{-1}$ DD was added and the pH was set to 8.0. Glucose was added every 24 h to adjust a final concentration of 5% (w/v).

Figure 5A:
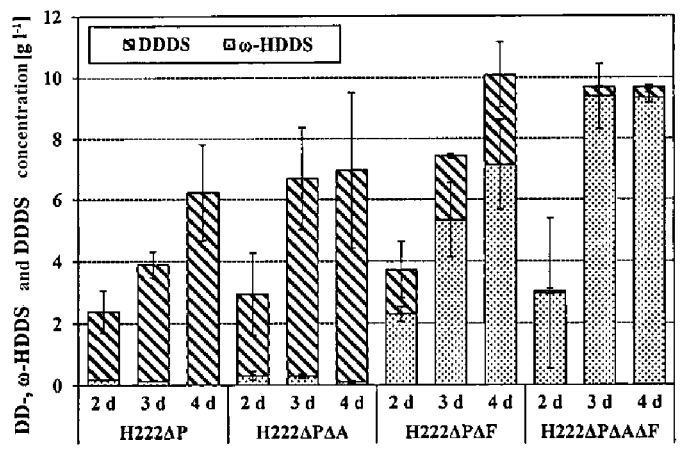

*Y. lipolytica* H222ΔP here formed relatively large quantities of dicarboxylic acids and can thus be used as initial strain for the construction of a corresponding production strain for dicarboxylic acids (FIG. 5A).

*Y. lipolytica* H222ΔPΔA and also H222ΔPΔF formed increased quantities of ω-hydroxy fatty acids and can thus be used as initial strains for the construction of corresponding production strains for ω-hydroxy fatty acids. Here *Y. lipolytica* H222ΔPΔF is to be preferred compared with H222ΔPΔA (FIG. 5A).

*Y. lipolytica* H222ΔPΔAΔF formed only small quantities of dicarboxylic acids and is thus the preferred initial strain for the construction of production strains for ω-hydroxy fatty acids (FIG. 5A).

Figure 5B:
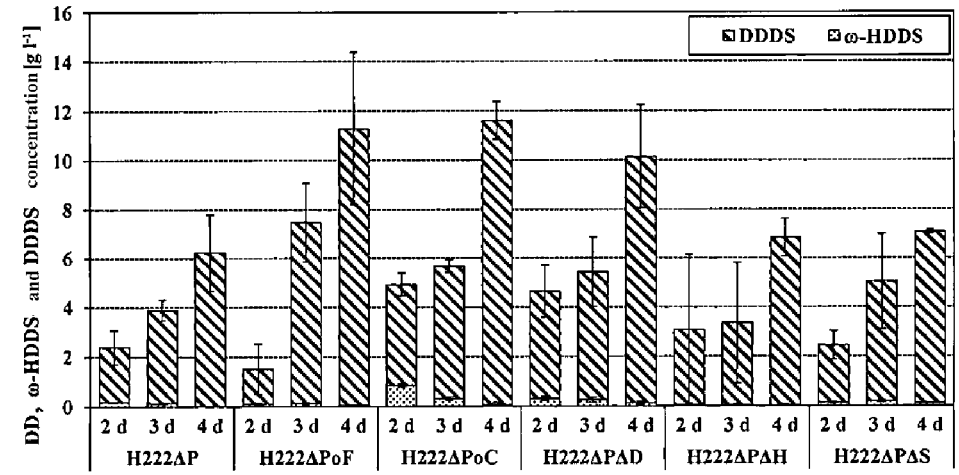
FIG. 5B—The deletion of DGA1 in the strain *Y. lipolytica* H222ΔP (resulting strain: *Y. lipolytica* H222ΔPΔD) resulted in an increased production of dicarboxylic acids whereas the deletions of PAH1 and SCT1 (resulting strains: *Y. lipolytica* H222ΔPΔH and H222ΔPΔS) did not significantly increase the production of dicarboxylic acids.

The overexpressions of FAO1 and CPR1 in the strain *Y. lipolytica* H222ΔP (resulting strains: *Y. lipolytica* H222ΔPoF and H222ΔPoC) in each case resulted in an increased production of dicarboxylic acids (FIG. 5B).

The deletion of DGA1 in the strain *Y. lipolytica* H222ΔP (resulting strain: *Y. lipolytica* H222ΔPΔD) resulted in an increased production of dicarboxylic acids whereas the deletions of PAH1 and SCT1 (resulting strains: *Y. lipolytica* H222ΔPΔH and H222ΔPΔS) did not significantly increase the production of dicarboxylic acids (FIG. 5B).

Figure 5C:
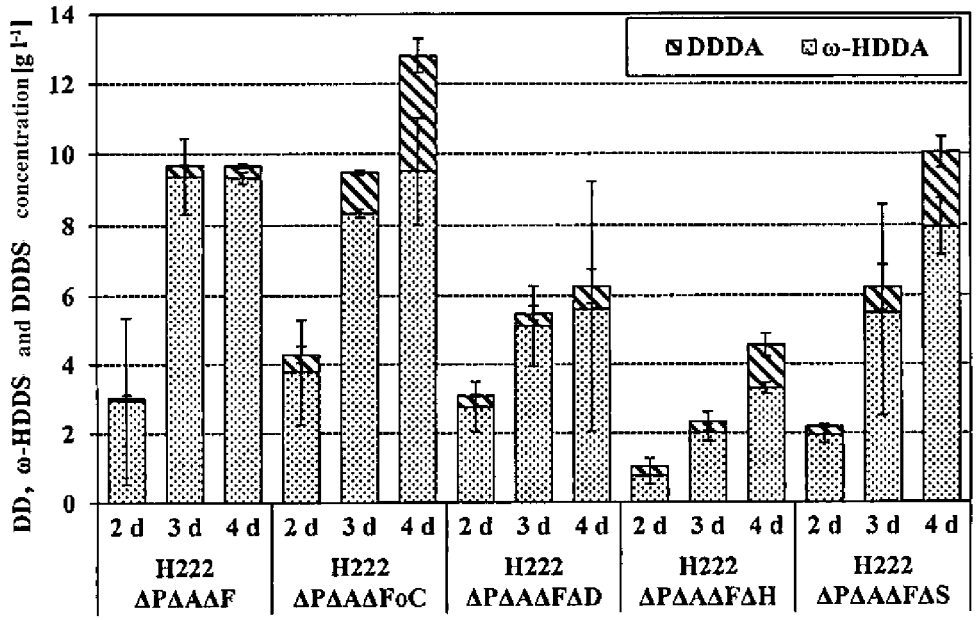
FIG. 5C—The overexpression of CPR1 in the strain *Y. lipolytica* H222ΔPΔAΔF (resulting strain: *Y. lipolytica* H222ΔPΔAΔFoC) resulted in an increased production of dicarboxylic acids but not of ω-hydroxy fatty acids.

The overexpression of CPR1 in the strain *Y. lipolytica* H222ΔPΔAΔF (resulting strain: *Y. lipolytica* H222ΔPΔAΔFoC) resulted in an increased production of dicarboxylic acids but not of ω-hydroxy fatty acids (FIG. 5C).

The deletions of DGA1, PAH1 and SCT1 in the strain *Y. lipolytica* H222ΔPΔAΔF (resulting strains: *Y. lipolytica* H222ΔPΔAΔFΔD, H222ΔPΔAΔFΔH and H222ΔPΔAΔFΔS) did not result in an increased production of ω-hydroxy fatty acids (FIG. 5B).

Example 9

Enzyme Test to Determine the (Fatty) Alcohol Dehydrogenase and Oxidase Activity The enzyme activities of the (fatty) alcohol dehydrogenases and oxidase were determined in cell lysates of the strains *Yarrowia lipolytica* H222ΔP, H222ΔPΔA, H222ΔPΔF, H222ΔPΔAΔF and H222ΔPoF. The cells were cultivated as described in Example 8 and harvested and macerated after three days.

The (fatty) alcohol dehydrogenase and oxidase activities were performed as described in Matatiele (2005) (Matatiele P R (2005) PhD thesis, University of the Free State, Republic of South Africa).

The (fatty) alcohol dehydrogenase assay (50 mM Tris-HCl pH 8.5, 1.3 mM dodecan-1-ol in DMSO, 2 mM NAD$^+$, 2 mM NAP$^+$, 1.5% (v/v) cell extract) was measured using a recording spectrophotometer at 30° C. and λ=340 nm and the enzyme activity was calculated with the aid of the determined increase in extinction (εNAD(P)H=6.3 mM$^{-1}$ cm$^{-1}$).

The (fatty) alcohol oxidase assay (50 mM glycine NaOH pH 9.0, 0.35 mM dodecan-1-ol in DMSO, 0.013% (w/v) peroxidase (150 U/mg), 0.044% (w/v) ABTS, 6 mM sodium azide, 1-5% (v/v) cell extract) was measured using a recording spectrophotometer at λ=405 nm and the enzyme activity was calculated with the aid of the determined increase in extinction ($\varepsilon_{ABTSox}$=18.4 mM$^{-1}$ cm$^{-1}$).

Figure 6A:
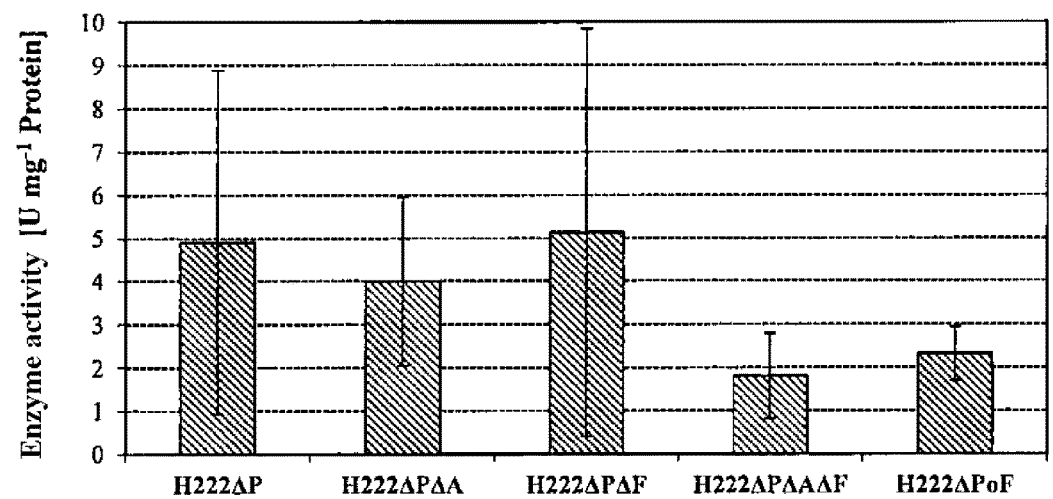
FIG. 6A—Surprisingly no clear difference of the (fatty) alcohol dehydrogenase was determined between the strains.

Surprisingly no clear difference of the (fatty) alcohol dehydrogenase was determined between the strains (FIG. 6A). This could be due to the remaining alcohol dehydrogenase activity. Furthermore, it is possible that the measured conversion of dodecan-1-ol is also catalyzed by cytochrome P450 and ultimately the activity of aldehyde dehydrogenases is determined.

Figure 6B:
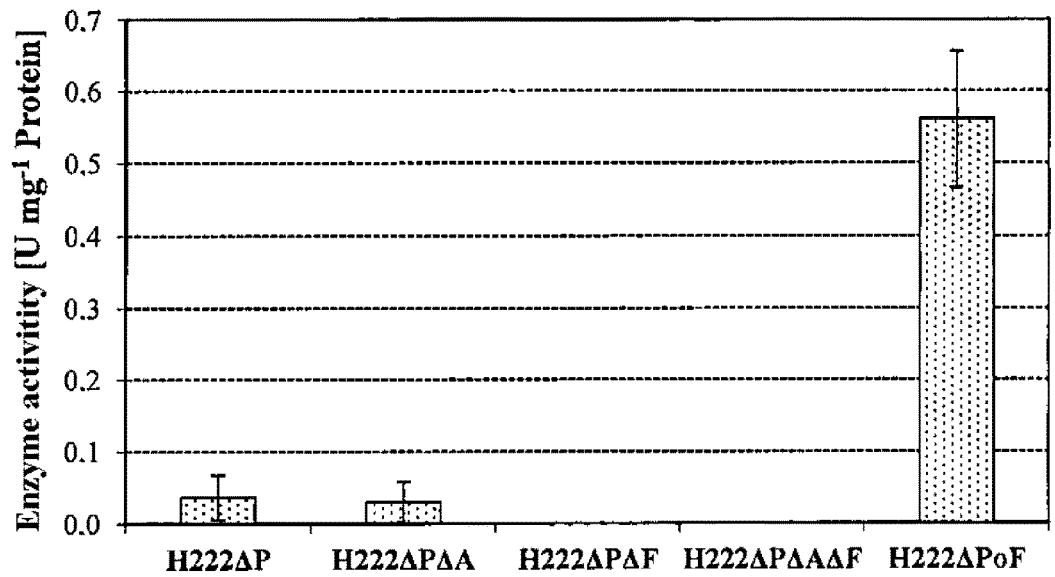
FIG. 6B—As was expected, the (fatty) alcohol oxidase activity could only be detected in the strains *Y. lipolytica* H222ΔP and H222ΔPΔA and not in the FAO1-deletion strains *Y. lipolytica* H222ΔPΔF and H222ΔPΔAΔF.

As was expected, the (fatty) alcohol oxidase activity could only be detected in the strains *Y. lipolytica* H222ΔP and H222ΔPΔA and not in the FAO1-deletion strains *Y. lipolytica* H222ΔPΔF and H222ΔPΔAΔF (FIG. 6B). The measured (fatty) alcohol oxidase activity was increased more than ten times by the overexpression of FAO1 (strain: *Y. lipolytica* H222ΔPoF).

Example 9

Cultivation of *Y. lipolytica* H222ΔPΔF in the Fermenter

In order to check whether the production strains are capable of producing larger quantities of dicarboxylic acids and/or ω-hydroxy fatty acids and accumulating in the culture medium, the strain *Y. lipolytica* H222ΔPΔF was cultivated for 7 d in the fermenter. The cultivation medium here was minimal medium with glucose and an increased quantity of mineral salts, trace elements and vitamins (5% (w/v) glucose, 2 g l$^{-1}$ KH$_2$PO$_4$, 0.32 g l$^{-1}$ K$_2$HPO$_4$×3 H$_2$O, 6 g l$^{-1}$ (NH$_4$)$_2$SO$_4$, 1.4 g l$^{-1}$ MgSO$_4$×7 H$_2$O, 1 g l$^{-1}$ NaCl, 0.8 g l$^{-1}$ Ca(NO$_3$)$_2$×4 H$_2$O, 1 mg l$^{-1}$ H$_3$BO$_3$, 0.08 mg l$^{-1}$ CuSO$_4$×5 H$_2$O, 0.2 mg l$^{-1}$ KI, 0.8 mg l$^{-1}$ MnSO$_4$×4 H$_2$O, 0.4 mg l$^{-1}$ Na$_2$MoO$_4$×2 H$_2$O, 0.8 mg l$^{-1}$ ZnSO$_4$×7 H$_2$O, 12 mg l$^{-1}$ FeCl$_3$×6 H$_2$O, 0.6 mg l$^{-1}$ thiamine hydrochloride). Cultivation was carried out in a fermenter at 28° C. The oxygen saturation was adjusted to 55%. The cells were inoculated with an OD$_{600}$ of 1 and incubated for 2 d at pH 5.5 (automated titration of HCl and NaOH). After 2 d the pH was adjusted to 8.0 and 15 g l$^{-1}$ of dodecane was added after 2 d and 3 d. Glucose was added every 24 h in order to adjust a final concentration of 5-10% (w/v).

After cultivation for 6 d (i.e. after 4 d in the production phase), *Y. lipolytica* H222ΔPΔF formed 29.5 g l$^{-1}$ of ω-hydroxydodecanoic acid and 3.5 g l$^{-1}$ of dodecanoic acid (FIG. 7).

What is claimed:

1. A genetically engineered *Yarrowia lipolytica* cell, comprising:
   a. a disrupted fatty alcohol oxidase encoding FAO1 YALI0B14014g gene; and
   b. at least one disrupted acyl-CoA oxidase encoding gene selected from the group consisting of: POX1, POX2, POX3, POX4, POX5, and POX6,
   wherein the engineered *Yarrowia lipolytica* cell has reduced fatty alcohol oxidase activity relative to a wild type *Yarrowia lipolytica* cell.

2. The engineered *Yarrowia lipolytica* cell according to claim 1, wherein the fatty alcohol oxidase encoding FAO1 YALI0B14014g gene is partially deleted.

3. The engineered *Yarrowia lipolytica* cell according to claim 1, wherein the fatty alcohol oxidase encoding FAO1 YALI0B14014g gene is completely deleted.

4. The engineered *Yarrowia lipolytica* cell according to claim 1, wherein at least one acyl-CoA oxidase encoding gene selected from the group consisting of: POX1, POX2, POX3, POX4, POX5, and POX6 is partially deleted.

5. The engineered *Yarrowia lipolytica* cell according to claim 1, wherein at least one acyl-CoA oxidase encoding gene selected from the group consisting of: POX1, POX2, POX3, POX4, POX5, and POX6 is completely deleted.

6. The engineered *Yarrowia lipolytica* cell according to claim 1, having reduced acyl-CoA oxidase activity relative to a wild type *Yarrowia lipolytica* cell.

7. The engineered *Yarrowia lipolytica* cell according to claim 1, comprising: at least one disrupted fatty alcohol dehydrogenase encoding gene selected from the group consisting of: FADH, ADH1, ADH2, ADH3, ADH4, ADH5, ADH6, and ADH7.

8. The engineered *Yarrowia lipolytica* cell according to claim 1, wherein at least one fatty alcohol dehydrogenase encoding gene selected from the group consisting of: FADH, ADH1, ADH2, ADH3, ADH4, ADH5, ADH6, and ADH7 is partially deleted.

9. The engineered *Yarrowia lipolytica* cell according to claim 1, wherein at least one fatty alcohol dehydrogenase encoding gene selected from the group consisting of: FADH, ADH1, ADH2, ADH3, ADH4, ADH5, ADH6, and ADH7 is completely deleted.

10. The engineered *Yarrowia lipolytica* cell according to claim 1, further comprising: at least one disrupted fatty aldehyde dehydrogenase encoding gene selected from the group consisting of FALDH1, FALDH2, FALDH3 and FALDH4.

11. The engineered *Yarrowia lipolytica* cell according to claim 1, wherein at least one fatty aldehyde dehydrogenase encoding gene selected from the group consisting of FALDH1, FALDH2, FALDH3 and FALDH4 is partially or completely deleted.

12. The engineered *Yarrowia lipolytica* cell according to claim 1, having reduced fatty alcohol dehydrogenase activity relative to a wild type *Yarrowia lipolytica* cell.

13. The engineered *Yarrowia lipolytica* cell according to claim 1, comprising: at least one of the following genes disrupted selected from the group consisting of: phosphatidic acid dephosphohydrolase (PAH1), phospholipid diacylglycerol acyltransferase (LRO1), diacylglycerol acyltransferase (DGA1), and glycerol-3-phosphate acyltransferase (SCT1).

14. The engineered *Yarrowia lipolytica* cell of claim 13, further comprising: a disrupted acyl-CoA oxidase encoding gene selected from the group consisting of: POX1, POX2, POX3, POX4, POX5, and POX6.

15. The engineered *Yarrowia lipolytica* cell of claim 13, further comprising: at least one disrupted fatty alcohol dehydrogenase encoding gene selected from the group consisting of: FADH, ADH1, ADH2, ADH3, ADH4, ADH5, ADH6, and ADH7.

16. The engineered *Yarrowia lipolytica* cell of claim 13, wherein the disruption of the genes reduces the size of the lipid bodies.

17. The engineered *Yarrowia lipolytica* cell according to claim 1, comprising: a disrupted peroxisome biogenesis factor 10 protein (PEX10).

18. The engineered *Yarrowia lipolytica* cell of claim 17, further comprising: a disrupted acyl-CoA oxidase encoding gene selected from the group consisting of: POX1, POX2, POX3, POX4, POX5, and POX6.

19. The engineered *Yarrowia lipolytica* cell of claim 17, further comprising: at least one disrupted fatty alcohol dehydrogenase encoding gene selected from the group consisting of: FADH, ADH1, ADH2, ADH3, ADH4, ADH5, ADH6, and ADH7.

20. A genetically engineered *Yarrowia lipolytica* cell, comprising: a disrupted fatty alcohol oxidase encoding FAO1 YALI0B14014g gene.

21. The engineered *Yarrowia lipolytica* cell of claim 20, further comprising a disrupted peroxisome biogenesis factor 10 protein (PEX10).

* * * * *